(12) United States Patent
Arnoldussen et al.

(10) Patent No.: US 10,151,761 B2
(45) Date of Patent: Dec. 11, 2018

(54) DIAGNOSTIC METHOD FOR DIAGNOSING DEPRESSION AND MONITORING THERAPY EFFECTIVENESS

(71) Applicants: Brainlabs B.V., Laag Soeren (NL); Rijksuniversiteit Groningen, Groningen (NL); Academisch Ziekenhuis Groningen, Groningen (NL)

(72) Inventors: Eduard Antonius Joannes Arnoldussen, Laag Soeren (NL); Hans Christiaan Klein, Groningen (NL)

(73) Assignees: BRAINLABS B.V. (NL); RIJKSUNIVERSITEIT GRONINGEN (NL); ACADEMISCH ZIEKENHUIS GRONINGEN (NL)

( * ) Notice: Subject to any disclaimer, the term of this patent is extended or adjusted under 35 U.S.C. 154(b) by 0 days.

(21) Appl. No.: 14/765,094

(22) PCT Filed: Jan. 31, 2014

(86) PCT No.: PCT/NL2014/050054
§ 371 (c)(1),
(2) Date: Jul. 31, 2015

(87) PCT Pub. No.: WO2014/120010
PCT Pub. Date: Aug. 7, 2014

(65) Prior Publication Data
US 2016/0003849 A1    Jan. 7, 2016

(30) Foreign Application Priority Data
Jan. 31, 2013   (NL) .................................... 2010214

(51) Int. Cl.
| | | |
|---|---|---|
| *G01N 33/53* | (2006.01) | |
| *G01N 33/566* | (2006.01) | |
| *G01N 33/68* | (2006.01) | |
| *A61B 5/145* | (2006.01) | |
| *A61B 5/16* | (2006.01) | |
| *C12Q 1/6883* | (2018.01) | |
| *A61B 5/15* | (2006.01) | |
| *A61B 5/00* | (2006.01) | |
| *A61B 10/00* | (2006.01) | |

(52) U.S. Cl.
CPC ..... *G01N 33/6893* (2013.01); *A61B 5/14507* (2013.01); *A61B 5/14546* (2013.01); *A61B 5/15* (2013.01); *A61B 5/16* (2013.01); *A61B 5/165* (2013.01); *A61B 5/4848* (2013.01); *A61B 5/7275* (2013.01); *A61B 5/7282* (2013.01); *A61B 10/007* (2013.01); *C12Q 1/6883* (2013.01); *G01N 33/6896* (2013.01); *A61B 5/4884* (2013.01); *C12Q 2600/106* (2013.01); *C12Q 2600/154* (2013.01); *C12Q 2600/158* (2013.01); *G01N 2800/304* (2013.01); *G01N 2800/52* (2013.01); *G01N 2800/60* (2013.01)

(58) Field of Classification Search
None
See application file for complete search history.

(56) References Cited

FOREIGN PATENT DOCUMENTS

| WO | 2009/111595 A2 | 9/2009 |
| WO | 2012/085557 A2 | 6/2012 |
| WO | 2013/009183 A1 | 1/2013 |

OTHER PUBLICATIONS

Donati, Rasenick: "Lipid rafts, G proteins and the etioliogy of an treatment for depression: prgress toward a depression biomarker",Future Medicine Ltd, vol. 3, No. 5, Jan. 1, 2008 (Jan. 1, 2008), pp. 511-514, XP002716521, ISSN: 1479-6708 the whole document.

Christian Friedrich Jehn et al: "Biomarkers of depression in cancer patients", Cancer. vol. 107, No. 11, Dec. 1, 2006 (Dec. 1, 2006). pp. 2723-2729, XP055088782, ISSN: 0008-543X, DOI: 10.1002/cncr. 22294 the whole document.

Norbert Muller et al: "Inflammatory Biomarkers and Depression", Neurotoxicity Research. vol. 19, No. 2, Feb. 1, 2011 (Feb. 1, 2011), pp. 308-318, XP055088762, ISSN: 1029-8428, DOI: 10.1007fs12640-010-9210-2 the whole document.

Heath D Schmidt et al: "Functional Biomarkers of Depression: Diagnosis, Treatment, and Pathophysiology" Neuropsychopharmacology. vol. 36, No. 12. Nov. 3, 2011 (Nov. 3, 2011). pp. 2375-2394, XP055088777, ISSN: 0893-133X. DOI: 10.1038/npp.2011.151 the whole document.

Barbara Schneider et al: "Biomarkers for major depression and its delineation from neurodegenerative disorders", Progress in Neurobiology. vol. 95, No. 4, Dec. 1, 2011 (Dec. 1, 2011). pp. 703-717, XP055088786, ISSN: 0301-0082, DOI: 10.1016fj.pneurobio.2011. 08.001 the whole document.

*Primary Examiner* — Olga N Chernyshev
(74) *Attorney, Agent, or Firm* — Banner & Witcoff, Ltd.

(57) ABSTRACT

The present invention relates to new biomarkers and new sets of biomarkers for diagnosing a mood disorder, preferably depression or monitoring the effectiveness of therapy for said mood disorder.

14 Claims, 29 Drawing Sheets

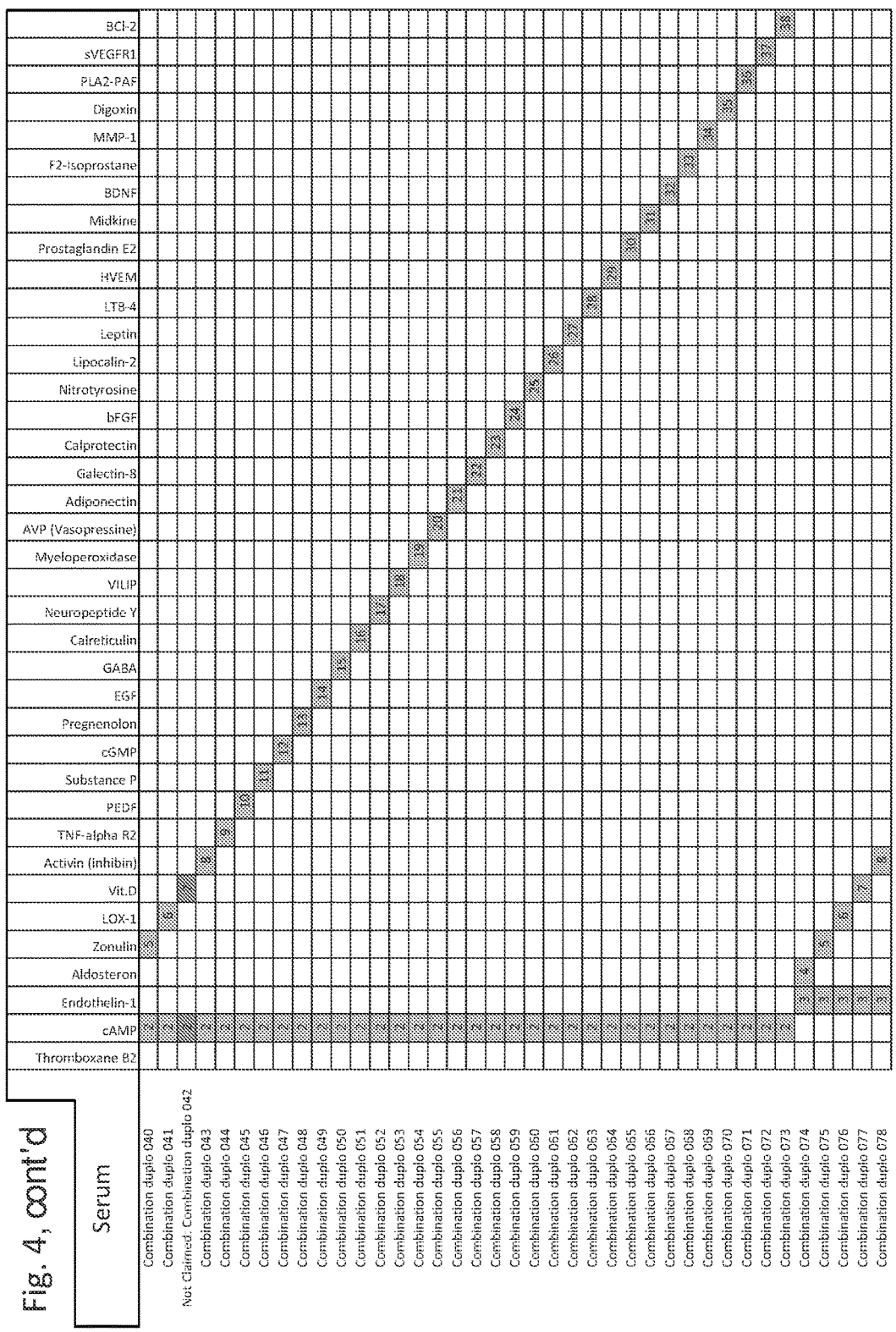
Fig. 4, cont'd

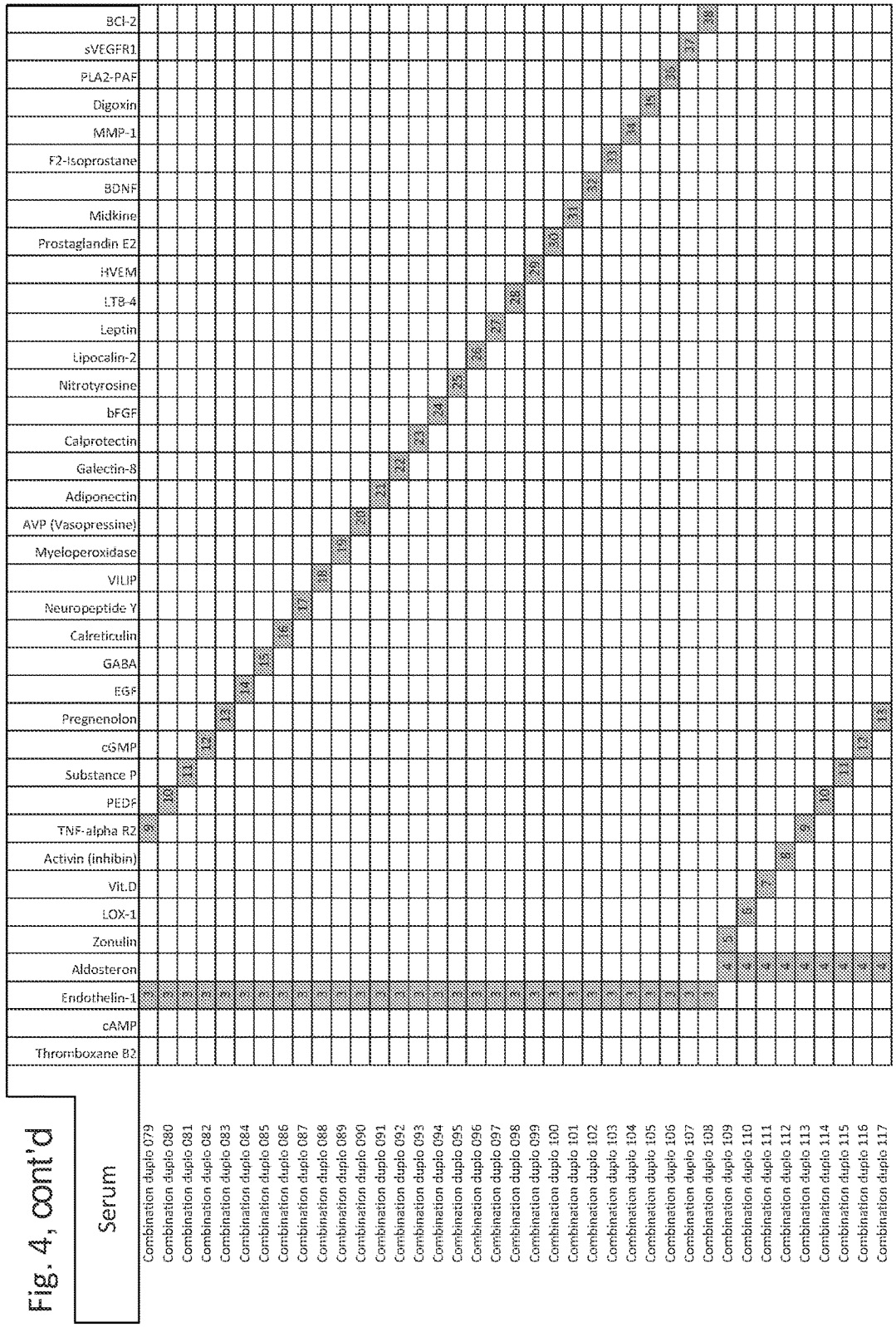
Fig. 4, cont'd

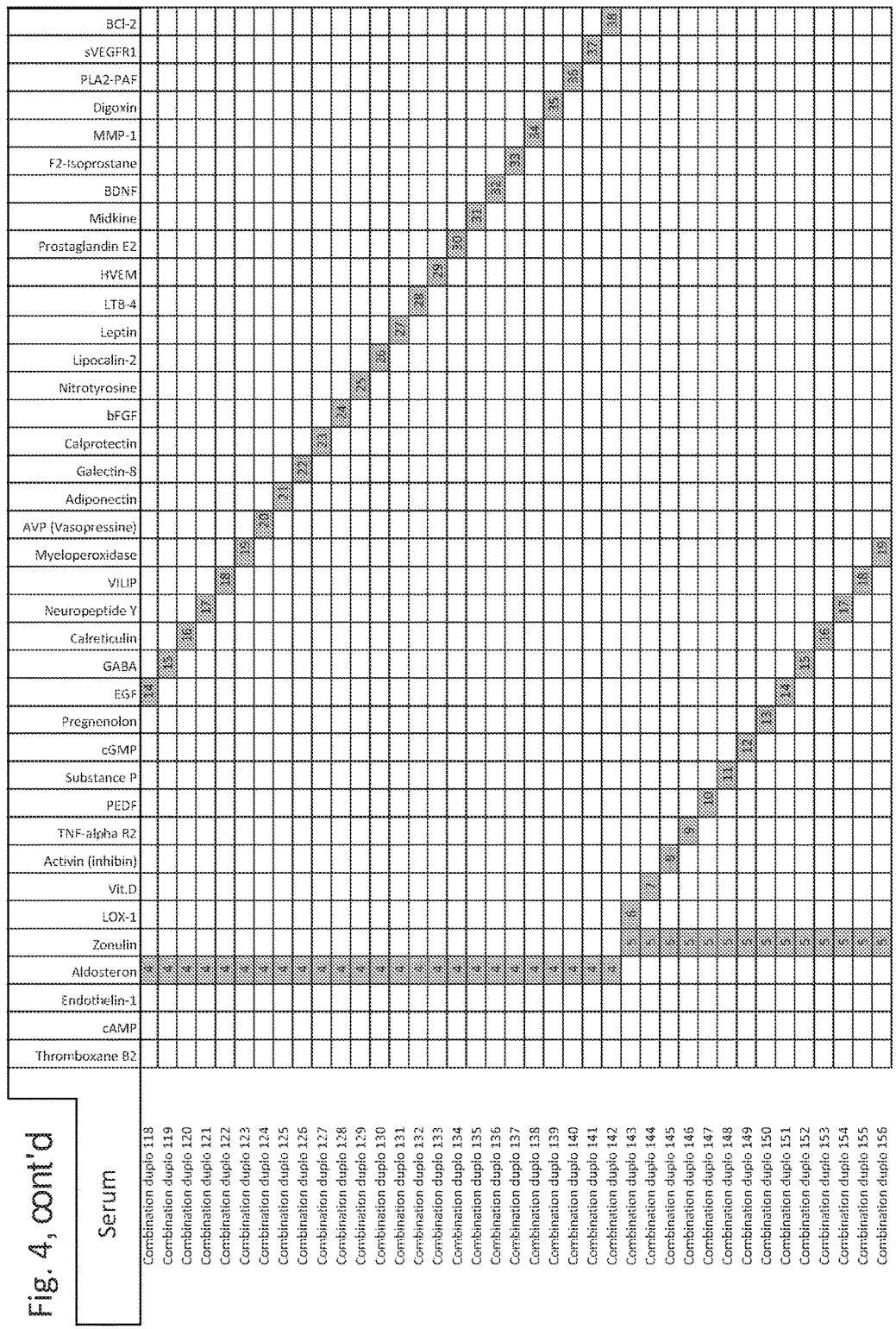
Fig. 4, cont'd

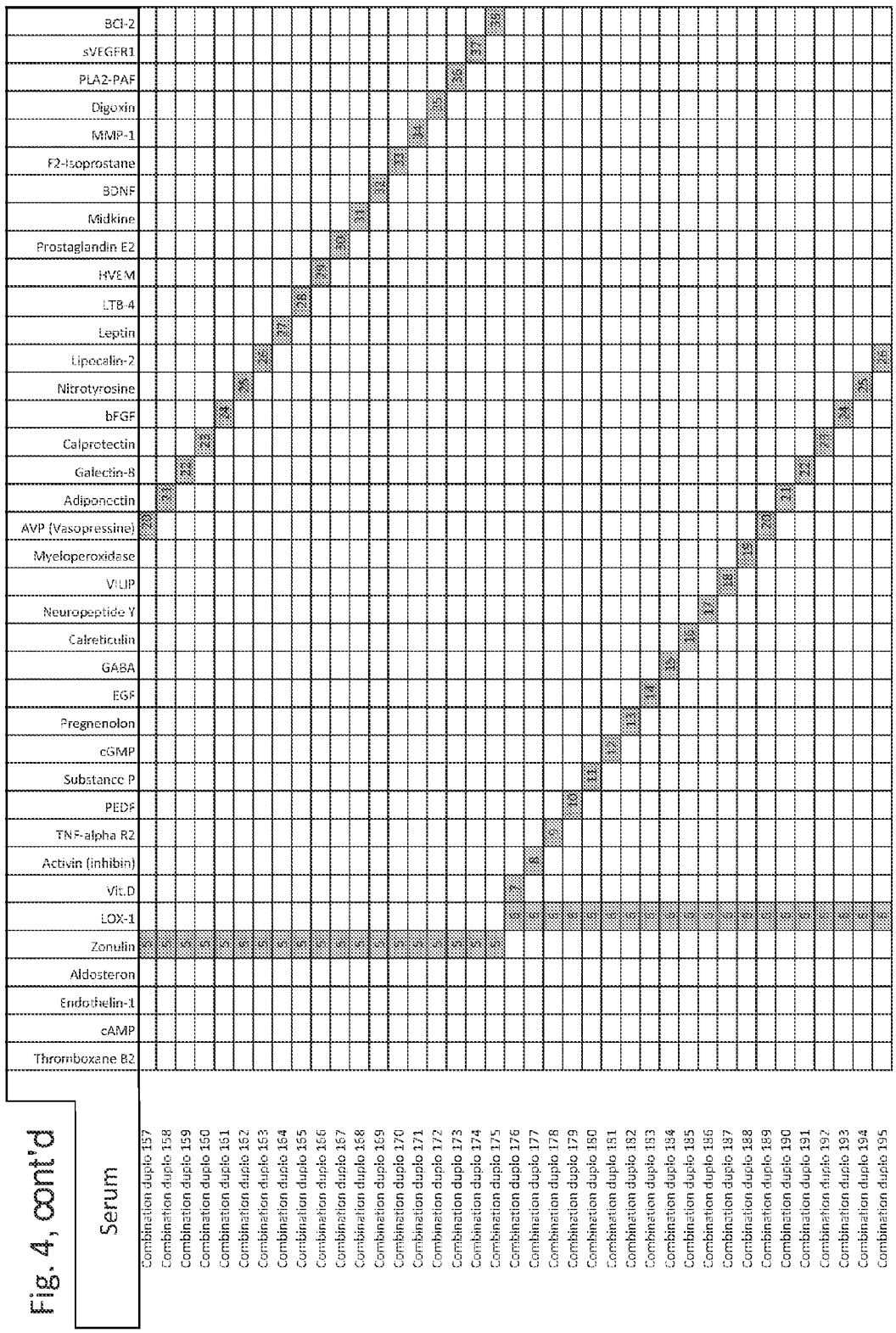

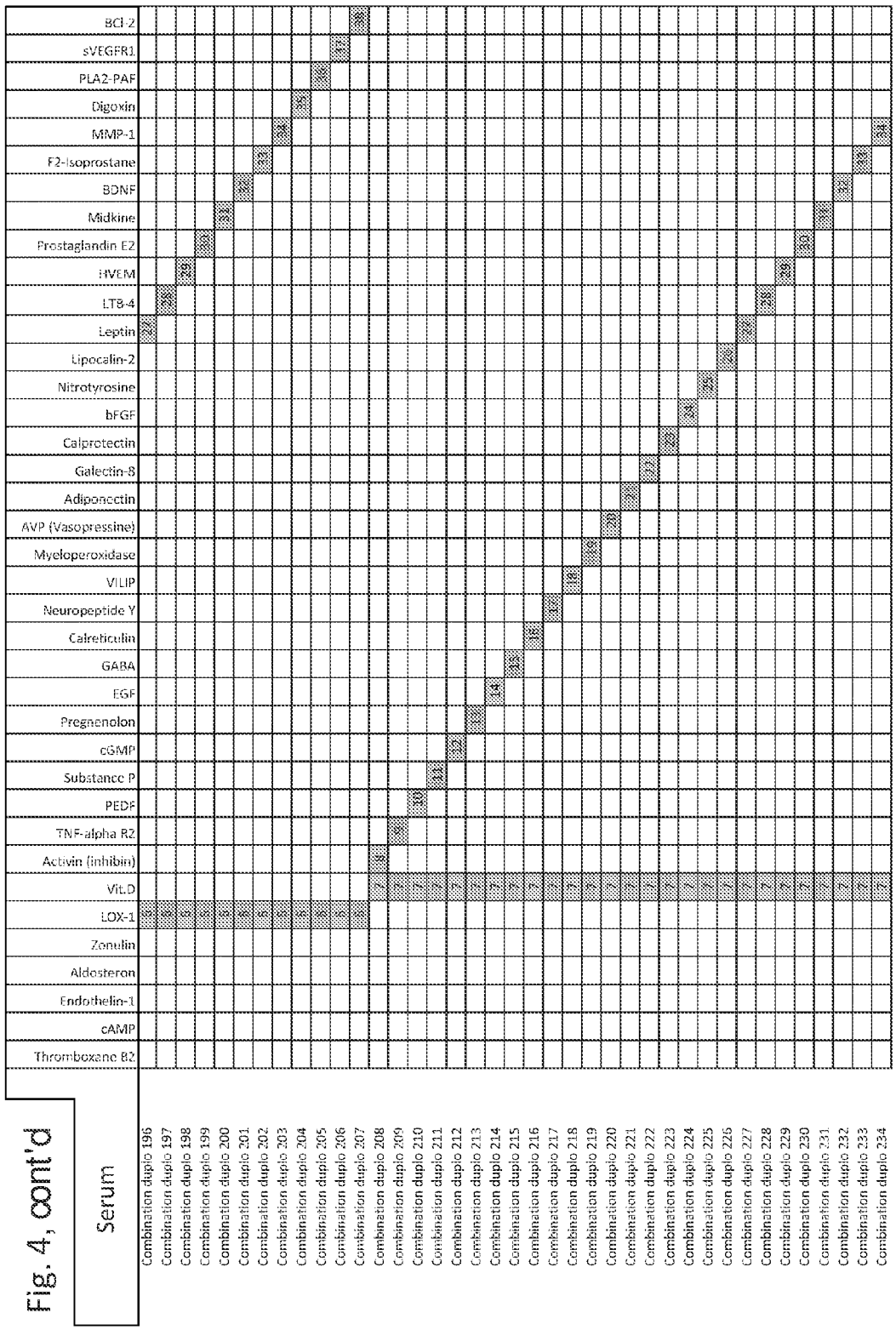
Fig. 4, cont'd

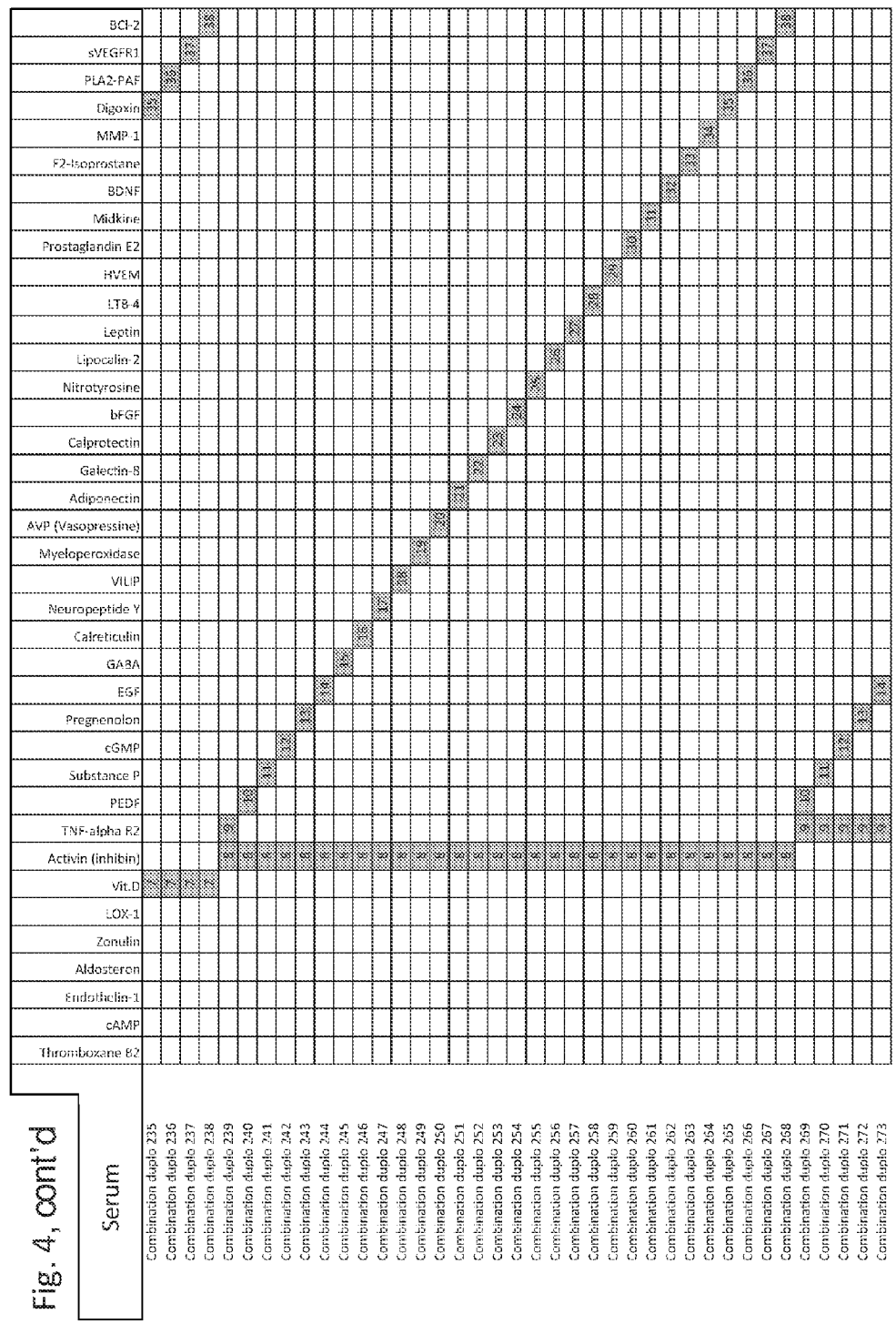
Fig. 4, cont'd fig. 4, cont'd

Fig. 4, cont'd

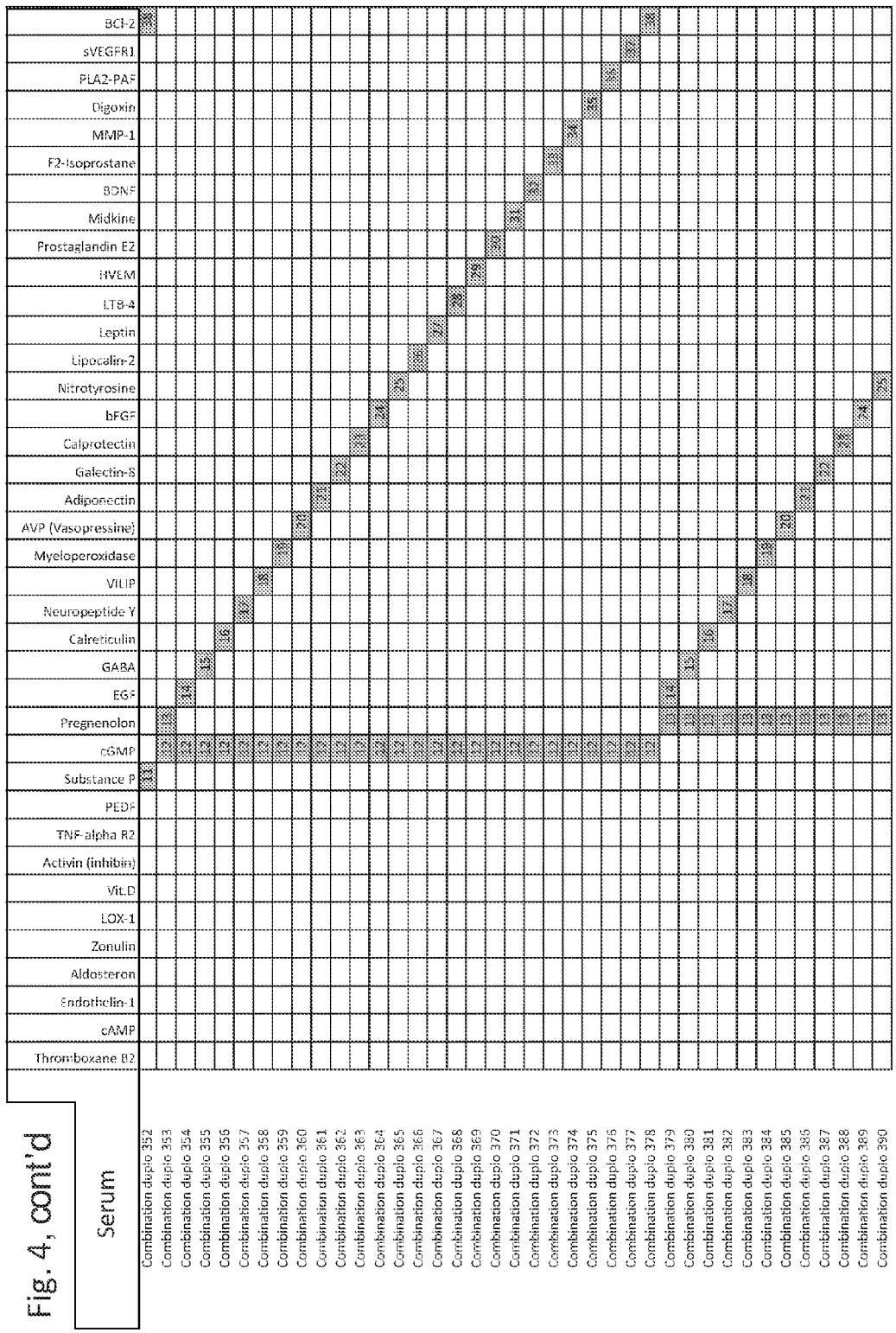
Fig. 4, cont'd

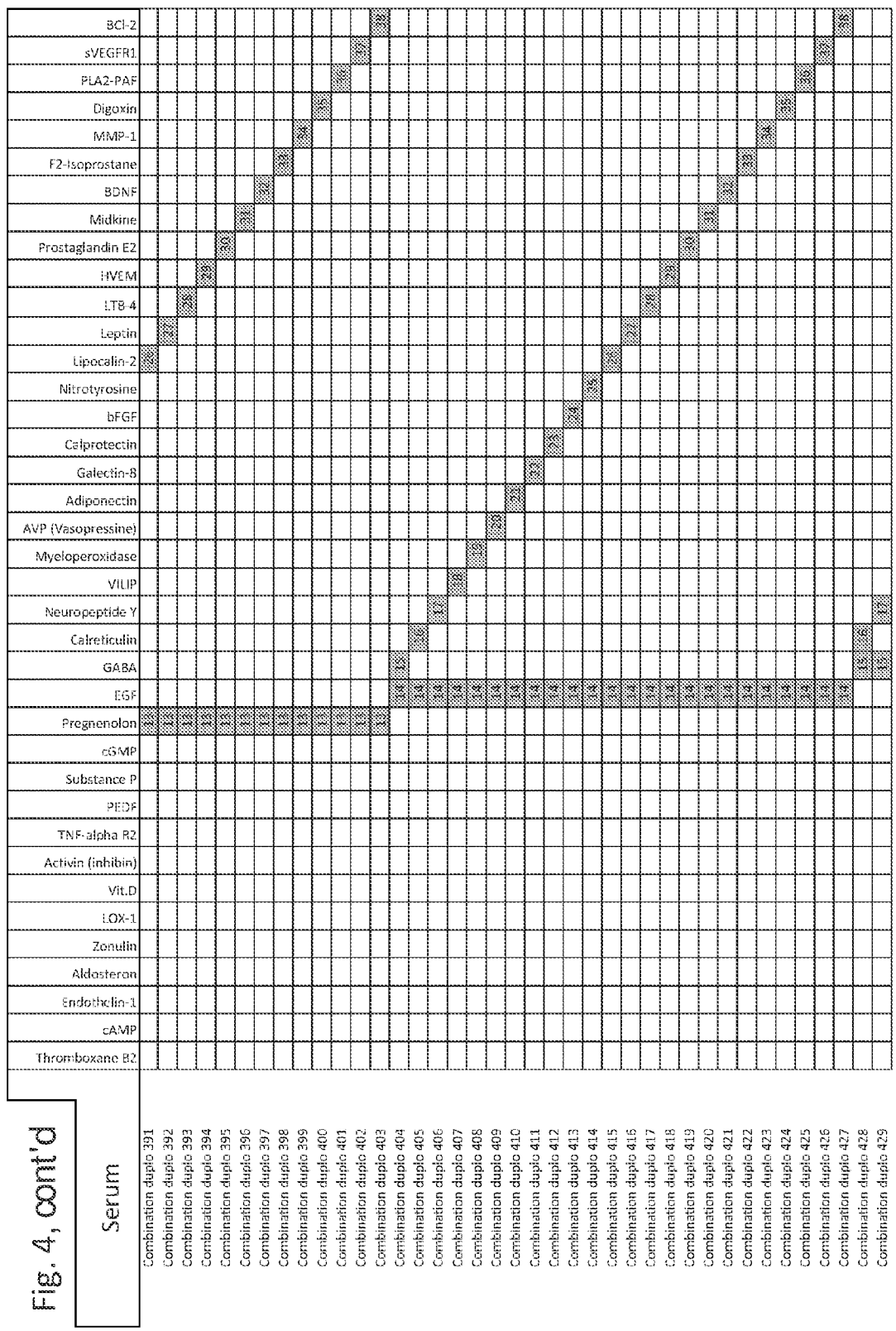
Fig. 4, cont'd

Fig. 4, cont'd

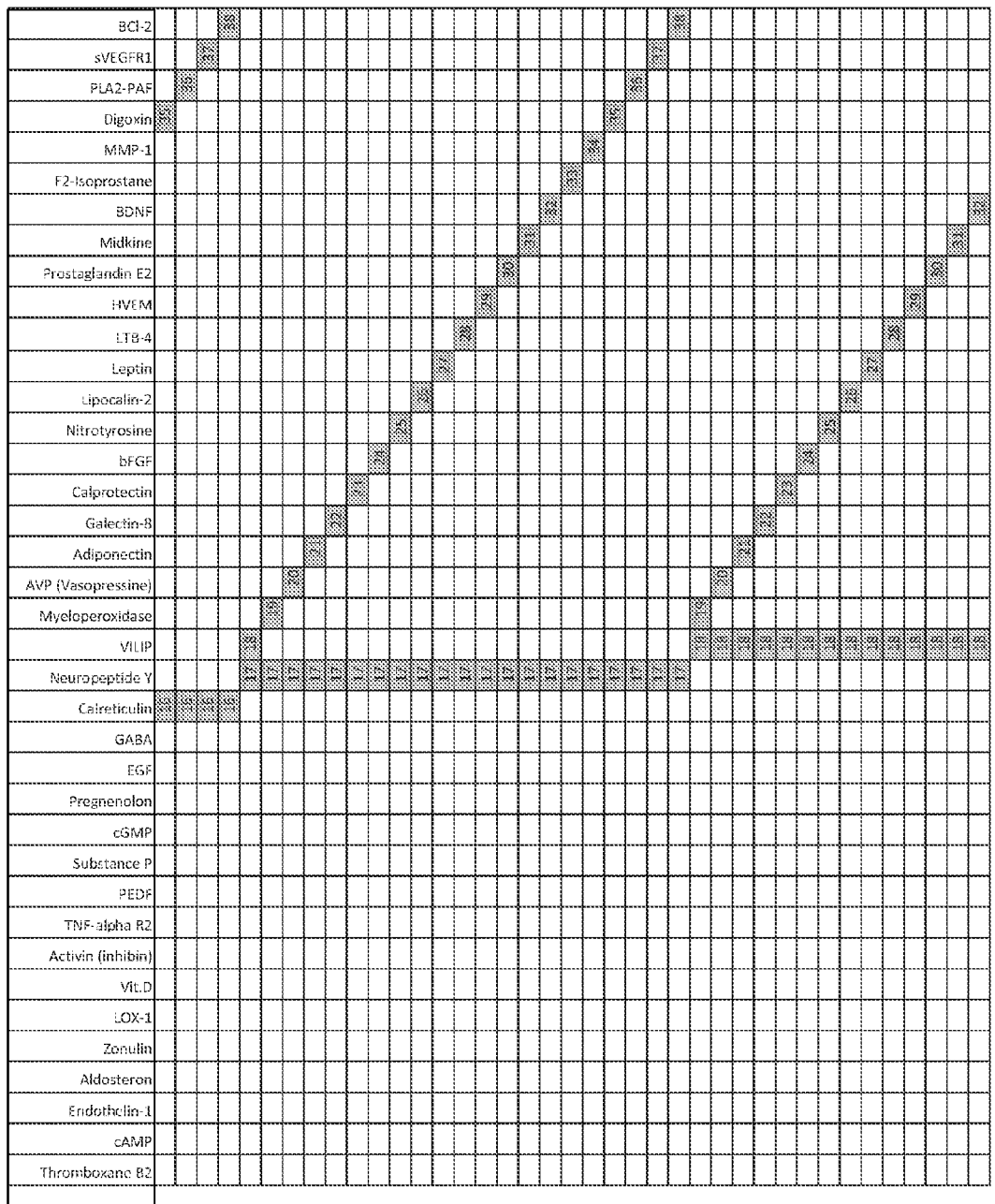
Fig. 4, cont'd

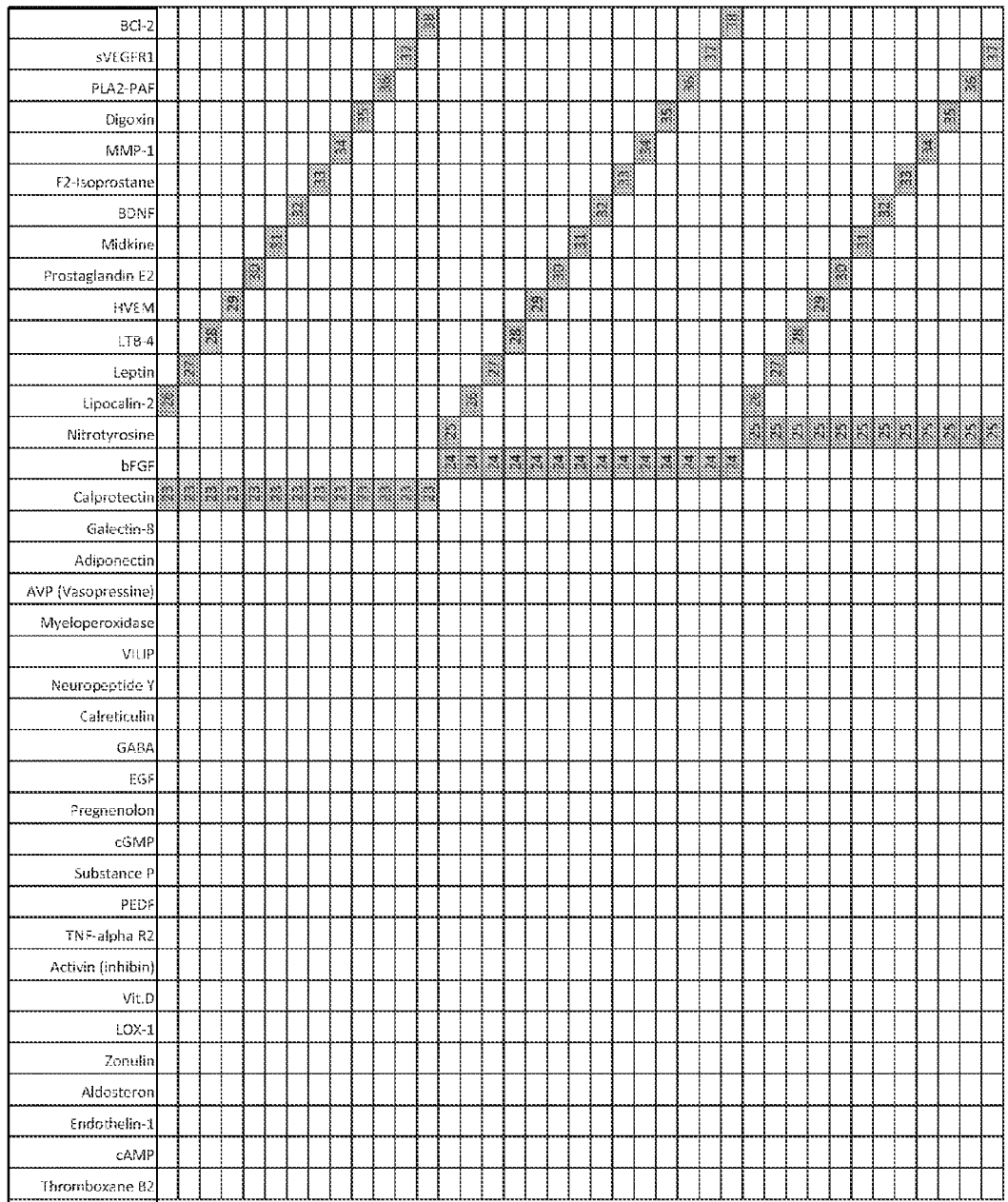
Fig. 4, cont'd

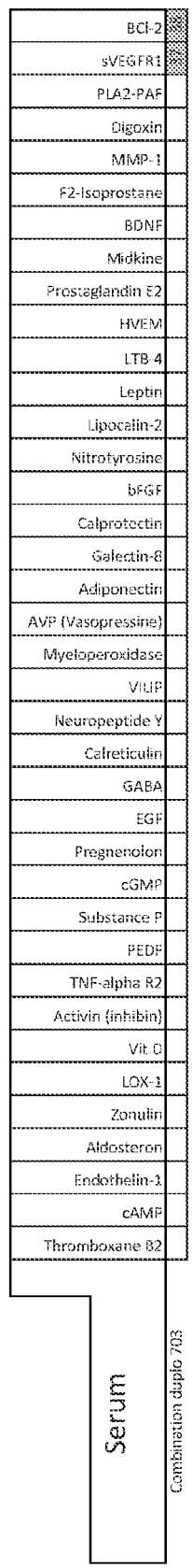
Fig. 4, cont'd

DIAGNOSTIC METHOD FOR DIAGNOSING DEPRESSION AND MONITORING THERAPY EFFECTIVENESS

RELATED APPLICATION DATA

This application is a National Stage Application under 35 U.S.C. 371 of co-pending PCT application number PCTNL2014050054 designating the United States and filed Jan. 31, 2014; which claims the benefit of NL application number 2010214 and filed Jan. 31, 2013 each of which are hereby incorporated by reference in their entireties.

FIELD OF THE INVENTION

The invention relates to the field of diagnostics, more specifically diagnosis of affective disorders, more specifically diagnosis of depression, by assaying for a set of psychiatric disease-markers. Further, the invention relates to a method for monitoring the effect of antidepressant therapy, being medication, psychotherapy or a combination of both.

BACKGROUND

Disorders of the mood are often called affective disorders, since affect is the external display of mood or emotion which is, however, felt internally. Mood disorders are defined as mixtures of symptoms packaged into syndromes. These syndromes are consensus statements from committees writing the nosologies of psychiatric disorders for the Diagnostic and Statistical Manual of Mental Disorders (DSM) of the American Psychiatric Association (Table 1).

Diagnosis both in clinical practice and in clinical research studies is based on these sets of specific signs and symptoms. These criteria have helped distinguish various mood disorders that may have different causes and that certainly require different clinical management. The most common and readily recognised mood disorder is major depression as a single episode or recurrent episodes. Dysthymia is a less severe but often longer-lasting form of depression, i.e. over two years in duration and often unremitting. Another type of mood disorder is bipolar disease, which is characterised by the occurrence of manic episodes besides depression.

There are no pathognomonic markers of depression, although this is an area of active research (Duffy A., 2000, Can. J. Psychiatr., 45:340-348).

TABLE 1

Diagnostic criteria for major depressive disorder*

| | |
|---|---|
| A. | The patient has depressed mood (e.g., sad or empty feeling) or loss of interest or pleasure most of the time for 2 or more weeks plus 4 or more of the following symptoms |
| | Sleep — Insomnia or hypersomnia nearly every day |
| | Interest — Markedly diminished interest or pleasure in nearly all activities most of the time |
| | Guilt — Excessive or inappropriate feelings of guilt or worthlessness most of the time |
| | Energy — Loss of energy or fatigue most of the time |
| | Concentration — Diminished ability to think or concentrate; indecisiveness most of the time |
| | Appetite — Increase or decrease in appetite |
| | Psychomotor — Observed psychomotor agitation/retardation |
| | Suicide — Recurrent thoughts of death/suicidal ideation |
| B. | The symptoms do not meet criteria for a mixed episode (major depressive episode and manic episode) |
| C. | The symptoms cause clinically significant distress or impairment in social, occupational, or other important areas of functioning |
| D. | The symptoms are not due to the direct physiological effects of a substance (e.g., a drug of abuse, a medication) or a general medical condition |
| E. | The symptoms are not better accounted for by bereavement |

*Adapted from the *Diagnostic and Statistical Manual of Mental Disorders*, 4th editon.'

Depressive disorders are associated with poor work productivity, as indicated by a 3-fold increase in the number of sick days in the month preceding the illness for workers with a depressive illness compared with coworkers who did not have such an illness (Parikh, S. V. et al., 1996, J. Affect. Disord. 38:57-65; Kessler, R. C. et al., 1999, Health Aff. 18:163-171).

Depressive illnesses also affect family members and caregivers (Denihan, A. et al., 1998, Int. J. Geriatr. Psychiatr. 13:691-694), and there is increasing evidence that children of women with depression have increased rates of problems in school and with behaviour, and have lower levels of social competence and self-esteem than their classmates with mothers who do not have depression (Goodman, S. H. and Gotlib, I. H., 1999, Psychol. Rev. 106:458-490). Depression is the leading cause of disability and premature death among people aged 18 to 44 years, and it is expected to be the second leading cause of disability for people of all ages by 2020 (Murray, C. J. and Lopez, A. D., 1997, The Lancet 349:1498-1504; Gredon, J. F., 2001, J. Clin. Psychiatr. 62:26-31).

Depressive illnesses have also been shown to be associated with increased rates of death and disability from cardiovascular disease (e.g. Pratt, L. A. et al., 1996, Circulation 94:3123-3129, Bush, D. E. et al., 2001, Am. J. Cardiol. 88:337-341). Among 1551 study subjects without a history of heart disease who were followed for 13 years, the odds ratio for acute myocardial infarction among the subjects who had a major depressive episode was 4.5 times higher than among those who did not have a depressive episode. Among consecutive patients admitted to hospital with an acute myocardial infarction who had their mood measured with a standard depression rating scale, even those with minimal symptoms of depression had evidence of higher subsequent risk of death following their infarction and over the next 4 months. This risk was independent of other major risk factors, including age, ventricular ejection fraction and the presence of diabetes mellitus.

Surprisingly, for such a common disease there is little agreement on the association between age and onset. This is due to the fact that research is hampered by the absence of an unambiguous and universally agreed on set of diagnostic criteria and the fact that many of the studies have included patients already in the medical care system. It is well known that many people who meet the diagnostic criteria for depression do not seek treatment.

Despite its high prevalence, only one-third of all patients with depression receive adequate treatment (Judd, L. L. et al., 1996, Am. J. Psychiatry 153:1411-1417). The following are 4 common clinical errors that lead to diagnostic or treatment failures associated with depressive disorders:

Insufficient questioning. Diagnostic failures occur when the patient is not asked questions that may elicit the symptoms of a mood disorder despite what should be a high index of suspicion based on its prevalence. The mnemonic "SIGECAPS" (sleep, interest, guilt, energy, concentration, appetite, psychomotor, suicide) (Table 1) may be a useful clinical adjunct (i.e., 4 or more SIGECAPS for major depression, 2 or 3 SIGECAPS for dysthymia).

Failure to consult a family member. Owing to the cognitive distortions associated with the disease, it is not unusual for patients to minimize or exaggerate their symptoms. Thus, in patients who are relatively new to one's practice, it is risky at best to make (or exclude) a diagnosis of depression without collateral information from a relative, such as a spouse or parent.

Acceptance of a diagnosis of a mood disorder despite lack of diagnostic criteria (e.g., starting treatment for depression when only a "depressed mood" is present without the concomitant mental and physical symptoms [i.e., SIGECAPS]).

Exclusion of a diagnosis or failure to start treatment for depression despite the associated symptom complex (e.g., "Of course you're depressed. Who wouldn't be depressed if these events were occurring in their life?" In other words, "explaining" the diagnosis rather than considering treatment options).

These clinical errors, coupled with the stigma associated with psychiatric conditions (Sirey, J. A. et al., 2001, Psychiatr. Serv. 52:1615-1620), result in the underdiagnosis of major mood disorders.

Another major hypothesis in the field of psychotherapy at present, is that recognition and treatment of both unipolar and bipolar depressions, causing all symptoms to remit for long periods of time, might prevent progression of the disease to more difficult states, emphasising that early recognition of mood disorder subtype is of great importance.

Taken all these data together, it is clear that there exists a major need for a reliable diagnosis of depression, or, alternatively, an assay that can confirm a diagnosis on basis of the SIGECAPS criteria.

SUMMARY OF THE INVENTION

As is discussed above many factors appear to play a role or contribute to the development of mood disorders, especially depression and more particularly major depression disorder (MDD). The invention now resides in the choice of a panel of biomarkers for the diagnosis and monitoring of depression, where this panel comprises biomarkers that are complementary as regards to the (putative) role they are playing in the ontogenesis of depression, thereby reflecting the above mentioned different hypotheses of depression.

In the panel of the invention markers reflecting the following groups may be included:

markers reflecting the mineral homeostasis hypothesis: PTH, AVP and its receptors (V1a, V1b), cAMP, digoxin, TRPM7, TRPM6, RACK-1, 17 beta estrathol, REA, telomerase, substance P and its receptor NK1, EGF and its receptors ERBB1-4, aldosteron and its receptor (MRC) and all substances which are known to influence the excretion of aldosteron like angiotensin I and II and their receptors (AT1, AT2), ACTH and its receptor (MC2), potassium and rennin.

markers reflecting endothelin dysfunction and oxidative stress chosen from: oxLDL and its receptor LOX-1, F2-isoprostane, nitrotyrosine, endothelin-1 and its receptors (Eta,ETb), elastin/desmosine.

markers reflecting tight junction & leaky gut hypothesis: zonulin proteins and zonula occludens toxin_(zot); LIGHT and_lymphotoxin ß receptor (LTβR)

markers reflecting pro-inflammatory hypothesis chosen from: all phospholipase A2 enzymes, PAF/PLAF; and all downstream components of arachidonic acid as well as dihomo-gamma-linolenic acid pathway like but not limited to PGA2, PGE2 an its receptors, Tromboxane B2 and its receptor TP, Prostacyclin, PGF2 and PGD2; downstream 5-HPETE and other HPETEs derivatives like but not limited to 5-HETE, LTB4 and its receptors (BLT1, BLT2 ect), LTC4, LTD4 LTE4; cysteinyl leukotriene receptor type 1, lipoxin (LXA4, LXB4), lipoxin $A_4$ receptor, PGE1, PGA1, $PGH_{1-15}OH$ triene.

markers reflecting the immune-inflammation hypothesis chosen from: lipocalin-2, TNF alpha, TNF beta, TNF alpha receptor type 1+2, HVEM, calprotectin, il-6 and its receptor, il-1 and its receptor, myeloperoxidase, galectin-8 and neopterin.

markers reflecting the neurogenesis hypothesis chosen from BDNF and its receptors TrkB and LNGFR, midkine and its receptor RPTPζ, bFGF and its receptor HVEM and PEDF.

markers reflecting a (change in) energy state: leptin and its receptor (LEP-R), adiponectin and its receptors (ADIPOR1, ADIPOR2 and CDH13)

other markers chosen from: vitamin D and its receptor (VDR), cortisol and its receptor (GCR), annexin-1, pregnenolone and its receptor (GCR), Activin/inhibin and their receptors, GABA, VILIP-1, Neuropeptide Y, MMP-1, BCL-2, Calreticulin, cGMP and compounds from the NO-cGMP pathway including all agents which are known to influence the excretion of cGMP like atrial natriuretic peptide, brain natriuretic peptide and c-type natriuretic peptide; vasoactive intestinal peptide and calcitonin gene-related peptide, nitric oxide synthase (endothelial NOS, eNOS, neuronal NOS, nNOS) and l-arginine;

According to the invention a set of markers that can be used in an assay to diagnose an affective disorder, preferably MDD, bipolar depression or anxiety may be a set of two markers chosen from the above groups, which set may be supplemented by any marker from the above-mentioned groups. For testing in urine, preferably the set of two markers is chosen from a group of 32 markers, comprising activin, cAMP, aldosteron, digoxin, lipocalin, neopterin, LTB4, TNF alpha receptor 2, HVEM, PGE2, thromboxane B2, LOX-1, nitrotyrosine, F2-isoprostane, midkine, IGF, endothelin-1, c-GMP, GABA, vitamin D, cortisol, pregnenolone, substance P, EGF, calprotectin, leptin, myeloperoxidase, neuropeptide Y, CCK, sVEGFR1, AVP and adiponectin. For testing in serum, preferably, the set of two markers is chosen from a group of 38 markers comprising Activin, cAMP, aldosteron, lipocalin, TNF alpha receptor 2, HVEM, galectin-8, PGE2, thromboxane B2, LOX-1, nitrotyrosine, F2-isoprostane, BDNF, PEDF, midkine, endothelin-1, c-GMP, GABA, vitamin D, pregnenolone, substance P, EGF, zonulin, calprotectin, VILIP, leptin, AVP (vasopressine), neuropeptide Y, MMP-1, bFGF, digoxin, BCL-2, calreticulin, myeloperoxidase, LTB4, PLAF, sVEGFR1 and adiponectin Accordingly, the invention comprises a method for the diagnosis of a mood disorder comprising:

taking a body fluid sample of a subject;

measuring the content of one of more of the above-mentioned biomarkers in said sample; and compare the concentration that is measured with the concentration of the one or more biomarkers in a control subject; and diagnose for the mood disorder if the concentration is deviant from the concentration in control healthy subjects.

Preferably the mood disorder is chosen from depression, schizophrenia, psychosis and anxiety, more preferably the mood disorder is depression, chosen from dysthymia, endogenous depression, reactive depression, minor depression, major depression, psychotic depression, neurotic depression, unipolar depression and bipolar depression, most preferably major depression.

Further, the invention comprises a method to determine the influence of antidepressant therapy, being medication, psychotherapy, or a combination of both, in a subject comprising:

taking a body fluid sample of a subject and measuring the content of one or more biomarkers as disclosed herein;

repeating step a) with regular intervals during said treatment; and registering any difference in the concentration of the one or more measured biomarkers in the body fluid.

Also the invention comprises a method to monitor the progress of a mood disorder in a subject comprising performing a method according to the invention. Further, the invention also relates to the use of a panel of biomarkers in the diagnosis and monitoring of progression of a mood disorder, especially depression, and more particularly MDD.

DESCRIPTION OF THE FIGURES

FIG. 5. List of markers and proposed marker sets that can be used on urine samples.

DETAILED DESCRIPTION

Figure 1:
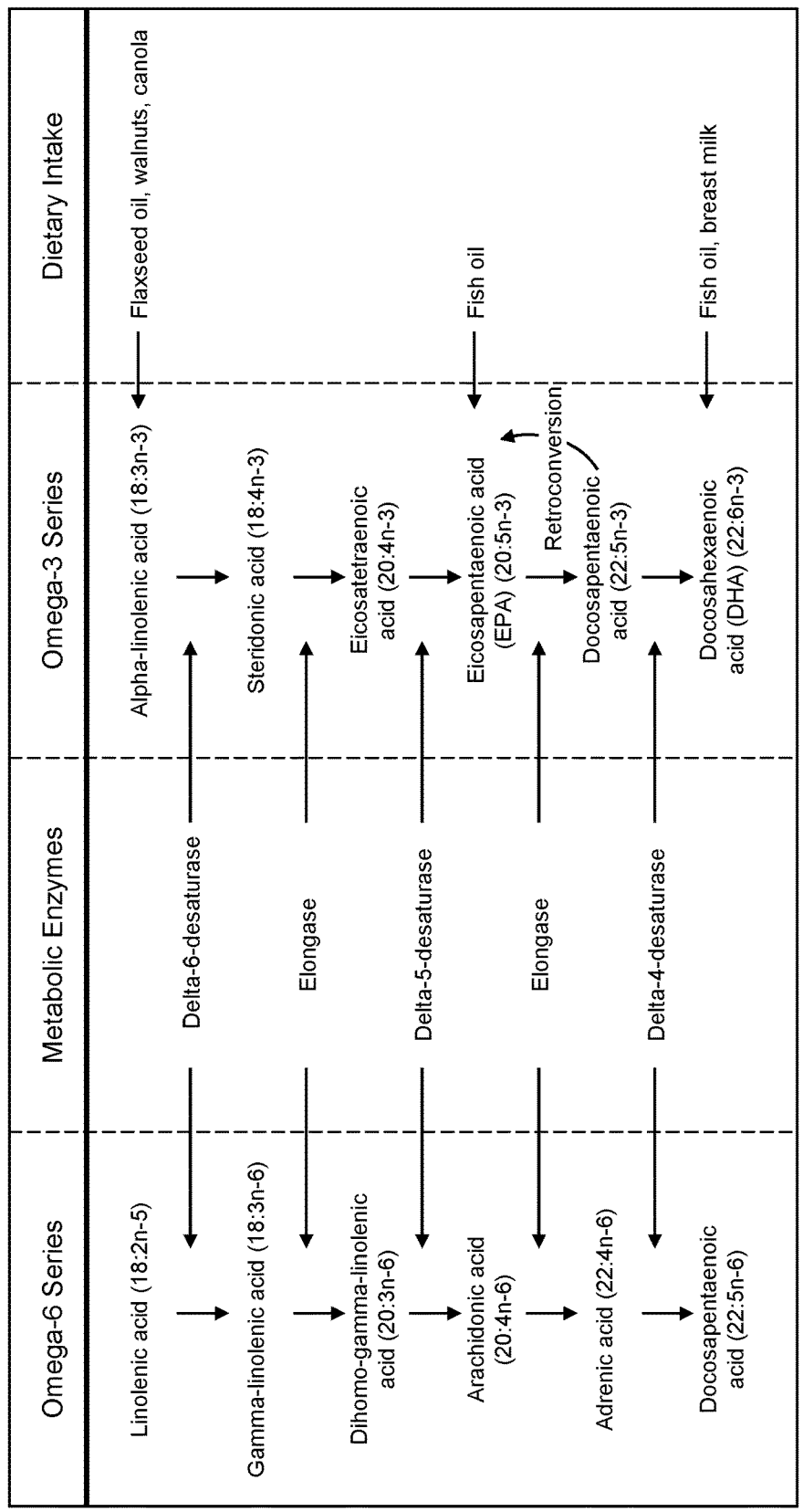
FIG. 1: Omega-6 & Omega-3 pathway

Major depressive disorder (MDD) is considered to be a heterogeneous and multifactorial disease. This suggests that the pathology underlying MDD can be rather divergent, which is in line with the considerable number of different MDD hypotheses that have been put forward. A few of these hypotheses are as follows.

Monoamine Hypothesis

Dysfunctions of monoaminergic systems (serotonin, norepinephrine and dopamine) may have a causal relation with MDD (Ruhe et al., 2007; Nutt et al., 2008). According to the monoamine theory, MDD is caused by an impaired monoaminergic neurotransmission, resulting in decreased extracellular norepinephrine (NE) and/or serotonin (5-HT) levels (Schildkraut, 1965; Doris et al., 1999). Diminished concentrations of serotonin and its metabolites have been demonstrated in cerebrospinal fluid (Åsberg et al., 1984) and in post mortem brain tissue of depressed patients (Cheethman et al., 1989).

There are also reports of altered platelet 5-HT transporter function (Nemeroff et al., 1994) and of altered 5-HT$_2$ receptor function in both the brain (Arango et al., 1992) and platelets (Bakish et al., 1997). Studies investigating NE and 5-HT metabolites in cerebrospinal fluid, blood or urine of patients with MDD and post-mortem studies seem to support the monoamine hypothesis of MDD (Belmaker and Agam, 2008; Pryor and Sulser, 1991). Associations of MDD with functional polymorphisms in the gene that codes for the enzyme monoamine oxidase A (MAO-A), which degrades monoamines in the brain (Wild and Benzel, 1994 Wild and Benzel, 1994) have also been reported (Chen and Ridd, 1999; Fan et al., 2010). In the past two decades, however, investigations have revealed several limitations of the monoamine hypothesis (Hirschfeld et al, 2000), and thus far research has failed to find convincing evidence for a primary dysfunction of one specific monoamine system in patients with MDD (Delgado et al, 2000). Arguably, monoamine systems are not dysfunctional per se but they may be challenged under certain conditions that require an increased availability of the neurotransmitter, e.g. during inflammation and chronic stress.

Mineral Homeostasis Hypothesis

Minerals are released into the blood when needed, the ability to maintain internal equilibrium of bone matrix density on the one hand and blood calcium and phosphate ion levels on the other hand by adjusting the complex negative feedback processes regulating mineral absorption from the digestive tract, mineral deposition/dissolution in the skeletal system, and mineral excretion by the kidneys; the endocrine control of mineral homeostasis is achieved by the antagonistic interplay of parathyroid hormone (PTH) from the parathyroid glands which tends to increase blood calcium levels by stimulating osteoclasts and (thyro)calcitonin from the thyroid gland which tends to decrease blood calcium levels by inhibiting osteoclasts. An association of depression status and severity with decreased serum 25(OH)D levels and increased serum PTH levels has been shown (Hoogendijk, 2008). Serum PTH levels are closely associated with urinary cAMP concentrations (Lukert, 1976).

Acute stress leads to an increase of catecholamines and cortisol which causes an increased exchange of magnesium ions for calcium ions at the intracellular level.

Studies in cultured cells have shown that intracellular calcium is can be controlled by receptors for many neurotransmitters and other neuro-active substances, such as glutamate, ATP, epinephrine, norepinephrine, GABA, acetyl choline, histamine, substance P, bradykinin, endothelin, serotonin, oxytocin, arginine-vasopressin, neuropeptide-Y, complement fragments, platelet activating factor, prostanoids, angiotensin II, thrombin and possibly also by endogenous ligands for opioid and benzodiazepine receptors (Verkhratsky et al., 1998). In the majority of eukaryotic cells, hormones or agents that increase cellular cAMP elicit a significant extrusion of $Mg^{2+}$ into the extracellular space or circulation (vorman and gunther, 1987; Romani and scarpa, 1990a; Romani and scarpa, 1990b). In all cellular models, $Mg^{2+}$ extrusion is a fast process that reaches the maximum within 8 minutes from the application of the stimulus. Surprisingly we demonstrated that mood disorder are correlated with increased concentrations of cAMP in blood and urine.

Magnesium ions enter and exit the cell via channels or channel like mechanisms.

TRPM7 (Nadler et al., 2001) and TRPM6 (Schlingmann et al., 2002) were the first channels identified as being able to transport $Mg^{2+}$ into mammalian cells.

TRPM7 plays a major functional role in neuronal function and survival under hypoxia or ischemic reperfusion conditions has increased. Owing to its ability to transport either $Ca^{2+}$ or $Mg^{2+}$, TRPM7 exhibits an ambivalent role based upon the permeating cation. Following activation by reactive oxygen/nitrogen species and prolonged oxygen and glucose deprivation, TRPM7 favours $Ca^{2+}$ fluxes that result in toxic event for neurons (Aarts et al. 2003). In contrast, $Mg^{2+}$ permeation of the channel enhances anti-apoptotic and cell survival mechanisms, preventing the anoxic death of neurons (Clark et al. 2006). The essential role of TRPM7 in detecting extracellular divalent Cations is supported by a recent study by Wei et al., (2007), which indicates that activation of the channel by low extracellular divalent cations is lethal to the cell. At the same time, Jiang et al., (2008) have reported that occlusion of the middle cerebral artery for 1 hour enhances TRPM7 expression in ipsilateral hippocampus, with deleterious consequences for the neurons. The increased expression of TRPM7 and its consequences are largely counteracted by pre-treatment with nerve growth factor via activation of TrkA pathway (Jiang et al., 2008). More recently, application of 5-lipoxygenase inhibitors can block TRPM7 current without affecting protein expression and cell membrane concentration, de facto preventing cell death (Chen et al., 2010).

TRPM6

The unique localization of TRPM6 channels in the colon and the renal distal convolute tubule, two epithelia otherwise highly impermeable to salt reabsorption, highlights the specific role of this channel in controlling intestinal $Mg^{2+}$ absorption and renal Mg2+ resorption, and consequently contributing to whole-body Mg2+ homeostasis. It confines an $Mg^{2+}$-permeable channel, the activity of which is strongly regulated by the intracellular $Mg^{2+}$ concentration ($[Mg^{2+}]_i$). Expression of TRPM6 is regulated by dietary $Mg^{2+}$, whereas TRPM7 is unaffected, supporting the idea of an important role of TRPM6 in transepithelial $Mg^{2+}$ transport. Estrogens (17B-estradiol) are known to upregulate TRPM6 mRNA in both colon and kidney.

Estrogen also acts via a rapid pathway on $Mg^{2+}$ homeostasis in addition to its transcriptional effect (Cao et al., 2009) which might explain the higher incidence of mood disorders in females. Furthermore the activity of TRPM6 channels is modulated by cellular signaling molecules like RACK-1 (Cao et al., 2008), repressor of estrogen receptor activity (REA) and EGF which is known to be an autocrine/paracrine magnesiotropic hormone (Groenestege et al. 2007).

$Ca^{2+}$/$Mg^{2+}$ balance is regulated by many hormones and stimuli, but this mechanism will not likely play a major role under acute stress conditions wherein cellular mechanisms are still capable to maintain proper electrolyte balance and thus Mg-ATP integrity. During chronic stress, however, intracellular magnesium might become critically low, thus compromising the capability to stabilize ATP, while the temporal decrease of calcium levels and increase of magnesium in the circulation will stimulate the parathyroid gland, through activation of calcium sensitive receptors, to increase the production of PTH. The increased levels of PTH stimulate both the back-resorption of calcium ions by the kidneys but also the resorption by osteoclasts in bone tissue of calcium and phosphate ions into the circulation. The lack of intracellular ATP (energy) in combination with calcium overload might threaten proper cell function, both centrally and peripherally. The latter is supported by the strong association of MDD with osteoporosis. This further fuels the inflow of calcium ions into cells which in combination with $HCO_3^-$ ions (likely through a $Cl^-$/$HCO_3^-$ exchange mechanism at the cellular level) will ultimately lead to calcification and thus apoptosis of both peripheral and CNS cells.

As witnessed in MMD by the mood stabilizing efficacy of lithium ions, changes of electrolyte balance (through IP3 in case of $Li^+$) has major effects on brain function. Studies in patients with MDD have shown increased $Ca^{2+}$/$Mg^{2+}$ ratios in cerebrospinal fluid (CSF) (Levine et al., 1999). Moreover, postmortem studies of depressed patients have shown a reduced $Mg^{2+}$ concentration in brain tissue (Nowak et al., 2010). Previously it was shown that the baseline level of cAMP in plasma and cerebrospinal fluid (Belmaker et al 1980; Post et al 1982; Maj et al 1984), was not altered in various mood states.

Phosphor nuclear magnetic resonance spectroscopy (NMR) has demonstrated a reduced $Mg^{2+}$ concentration in depressed patients, refractory to SSRI treatment (Iosifescu et al., 2005). In hippocampal synaptosomes, activation of protein kinase C (PKC) abolishes the blockade of NMDA dependent ion channels by $Mg^{2+}$ without changing the membrane potential (Pittaluga et al., 2000). Accordingly, intracellular administration of a PKC agonist potentiated NMDA receptor function in cultured hippocampal neurons (Xiong et al., 1998). This could lead to a feed-forward cycle; an NMDA dependent $Ca^{2+}$ current may increase PKC activity leading to further release of the $Mg^{2+}$ block of the NMDA dependent ion current. $Mg^{2+}$ also has a direct influence on PKC function. The catalytic subunit of PKC requires $Mg^{2+}$ as a cofactor (Hannun and Bell, 1990), and deactivation of PKC by adenosine triphosphate (ATP) depends on the presence of $Mg^{2+}$ (Wolf et al., 1985). Besides influencing glutamate neurotransmission through NMDA receptors, $Mg^{2+}$ depletion also affects hippocampal excitability via non-NMDA receptor mediated $Ca^{2+}$ currents, which can be suppressed by the $Ca^{2+}$ channel blocker verapamil (Pohl et al., 1992; Walden et al., 1992). Under normal conditions NMDA receptors admit only the amount of $Ca^{2-}$ necessary for neuronal function, but with improper function caused by insufficient $Mg^{2+}$, for instance, the influx of $Ca^{2+}$ will increase beyond manageable levels leading to the generation of toxic reactive oxygen species (ROS) and toxic amounts of nitric oxide (NO) radicals (Blaylock, 1999; Mark, 2001; Carafoli, 2005). Mg deficiency is known to correlate with an increase of substance P and osteoporosis (Rude R K, 2009). We demonstrated that mood disorders are correlated with increased concentrations of substance P in blood and surprisingly as well as in urine. Estrogens, (REA), EGF and RACK-1 can be used as biomarkers for mood disorders.

Further, magnesium deficiency is known to correlate with ageing, which means that telomerase may act as a marker for molecule for such a magnesium deficiency.

Other minerals are regulated in analogous fashion by endocrine negative feedback systems, e.g., sodium and potassium ion levels are regulated by the adrenocortical steroid hormone aldosterone.

Aldosterone, a steroid hormone secreted by the adrenal cortex, is the principle mineralocorticoid controlling sodium and potassium balance (Rogerson, 2000; Agarwal, 1999). The primary role of aldosterone is to promote unidirectional salt reabsorption across a variety of epithelial tissues, the salivary gland, intestine, sweat glands, and the kidney. Aldosterone is synthesized from cholesterol in the zona glomerulos of the adrenal cortex. Secretion of aldosterone is complicated, being affected by both hormones and electrolytes. However, the renin-angiotensin system (RAS) is the primary regulator of aldosterone secretion (Lumbers, 1999) Angiotensin II and potassium stimulate secretion of aldosterone by increasing the rate of synthesis of the hormone. The angiotensin converting enzyme (ACE) has been repeatedly discussed as susceptibility factor for major depression (MD) and the bi-directional relation between MD and cardiovascular disorders (Zill, 2012). Minor regulators include adrenocorticotropic hormone (ACTH) from the pituitary, atrial natriuretic peptide from the heart, and local adrenal secretion of dopamine. We demonstrated that mood disorders are correlated with increased concentrations of aldosteron and digoxin in blood as well as urine.

Oxidative Stress & Endothelin Dysfunction Hypothesis

Major depression has been shown to be accompanied by increased oxidative stress and lipid peroxidation. Plasma peroxides and serum oxidized LDL (oxLDL) antibodies are known to be correlated to major depression. (Maes, 2010). Atherosclerosis and depression are also known to be associated (Jones, 2003; Wiiteman, 2004; Hamer, 2010).

The endothelial injury, activation, and dysfunction caused by oxidized LDL (oxLDL) in the pathogenesis of atherosclerosis are exerted via lectin-like oxidized low-density lipoprotein receptor-1 (LOX-1) activation. LOX-1, initially identified as the major receptor for oxLDL in endothelial cells, can also be expressed in macrophages and smooth muscle cells (SMCs). The stage for atherosclerosis is set once endothelial dysfunction occurs. LOX-1 may play a role in initiating and potentiating this crucial first step.

Under conditions of hypercholesterolemia, hypertension, and diabetes, disease states that promote vascular injury, LOX-1 is highly expressed in blood vessels.

Induction of LOX-1 expression is mediated by angiotensin II and endothelin-1, both antagonists of NO. With elevated levels of LOX-1 on the endothelium, increased amounts of oxLDL can be endocytosed, an activity that further enhances LOX-1 expression. OxLDL through LOX-1 also increases the expression of angiotensin converting enzyme and reduces the intracellular concentration of NO. In addition to being the main receptor for oxLDL, LOX-1 has the ability to bind damaged or apoptotic cells, activated platelets, advanced glycation end products, and pathogenic organisms. Once bound, these ligands can be endocytosed or phagocytosed into the cell. Under physiological conditions, LOX-1 may play a role in host defense or serve to scavenge cellular debris. However, in pathological states, LOX-1 may be involved in binding proatherogenic materials, such as oxLDL, that activate the endothelium. With its ability to bind products that induce inflammation and endothelial activation, it is not surprising that elevated LOX-1 expression is observed in both initial and advanced atherosclerotic lesions. The stage for atherosclerosis is set once endothelial dysfunction occurs. Under conditions of hypercholesterolemia, hypertension, and diabetes which are all known to be associated with mood disorders, disease states that promote vascular injury, LOX-1 is highly expressed in blood vessels. Induction of LOX-1 expression is mediated by angiotensin II and endothelin-1, both antagonists of NO. With elevated levels of LOX-1 on the endothelium, increased amounts of oxLDL can be endocytosed, an activity that further enhances LOX-1 expression. OxLDL through LOX-1 also increases the expression of angiotensin converting enzyme and reduces the intracellular concentration of NO. Thus, LOX-1 activity amplifies the extent of endothelial dysfunction. However, oxLDL uptake by LOX-1 also mediates endothelial cell apoptosis, potentially via nuclear factor (NF)_B activation. This may result in direct vascular denudation and injury that may trigger or enhance an existing inflammatory reaction (Szmitko, 2003).

We demonstrated that mood disorders are correlated with increased concentrations of endothelin-1, F2-isoprostane, LOX-1 and nitro-tyrosine concentrations in blood as well as urine.

Tight Junction Hypothesis

Intestinal mucosal dysfunction characterized by an increased translocation of gram-negative bacteria (leaky gut) has suggested to play a role in the inflammatory pathophysiology of depression. It is suggested that the increased LPS translocation may mount an immune response and thus inflammatory response system activation in some patients with MDD and may induce specific "sickness behaviour" symptoms (Maes, 2008; Painsipp, 2011). T cell-derived LIGHT is known to activate epithelial LTβR to disrupt barrier function (Brad T. et al. 2007). Furthermore it was found that individuals with recent-onset psychosis and with multi-episode schizophrenia who have increased antibodies to gliadin may share some immunologic features of celiac disease, but their immune response to gliadin differs from that of celiac disease (Dickerson, 2010). Gliadin binds to CXCR3 and leads to MyD88-dependent zonulin release and increased intestinal permeability (Lammers, 2008). We demonstrated for the first time that the zonulin serum concentration is associated with mood disorders.

Zonulin

Intercellular tight junctions are dynamic structures involved in vectorial transport of water and electrolytes across the cell membranes of the intestinal epithelium and brain blood barrier. Zonula occludens toxin derived from *Vibrio cholerae* interacts with a specific intestinal epithelial surface receptor, with subsequent activation of a complex intracellular cascade of events that regulate tight junction permeability. Zonulin likely plays a pivotal role in tight junction regulation during developmental, physiological, and pathological processes, including tissue morphogenesis, movement of fluid, macromolecules and leukocytes between the intestinal lumen and the interstitium, and inflammatory/autoimmune disorders (Fasano, 2001; Wang, 2000).

Pro-Inflammatory Hypothesis

In the last 150 years, rapid expansion in Western populations has been associated with a change in diet, with omega-3 polyunsaturated fatty acids from fish, wild game, and plants being replaced by saturated fats from domestic animals and omega-6 polyunsaturated fatty acids from common vegetable oils (corn, safflower, and soybean) and other sources. These changes have resulted in a large increase in the ratio of omega-6 to omega-3 fatty acids in the general diet from 1:1 to more than 10:1 (4, 5). This has resulted in a high proportion of the common omega-6 fatty acid arachidonic acid, rather than EPA, in the cell membranes of most tissues. As depicted in FIG. 1 an increase in arachidonic acid also affects the production of EPA and DHA, owing to competition for metabolizing enzymes. The AA/EPA ratio can be used as a biomarker for mood disorders.

Antidepressant Efficacy of Omega-3 Fatty Acids (EPA) has been well documented for both major depression and bipolar depression (Pao-Yen Lin, 2007). The two omega-3 fatty acids, EPA and DHA, compete with arachidonic acid (AA) for incorporation into membrane phospholipids. Phospholipases A2 are enzymes that catalytically hydrolyzes the bond releasing arachidonic acid and lysophospholipids. Phospholipases A2 include several protein families with common enzymatic activity. Two most notable families are CA2+ dependent secreted and cytosolic phospholipases A2. Other families include $Ca^{2+}$ independent PLA2 (iPLA2) and lipoprotein-associated PLA2s (lp-PLA2), also known as platelet activating factor acetylhydrolase (PAF-AH). Increased PLA2 activity and PLA2-generated mediators are known to play a central role in acute inflammatory responses in the brain but also in oxidative stress associated with neurological disorders (Faraooqui, 2006). Phospholipase A2 and COX-2 genes also increase the risk of IFN-alpha induced depression by regulating polyunsaturated fatty acid level (Su K P, Huang S Y, 2010). EPA is important in balancing the immune function and physical health by reducing phospholipase A2, Platelet acitivating factor (PAF), arachidonic acid (AA level on cell membrane) prostaglandin E2 (PGE2) and LTB4 synthesis. (Joel M. Kremer, 1996). We also demonstrated the correlation of PLA2 and mood disorders.

Figure 2:
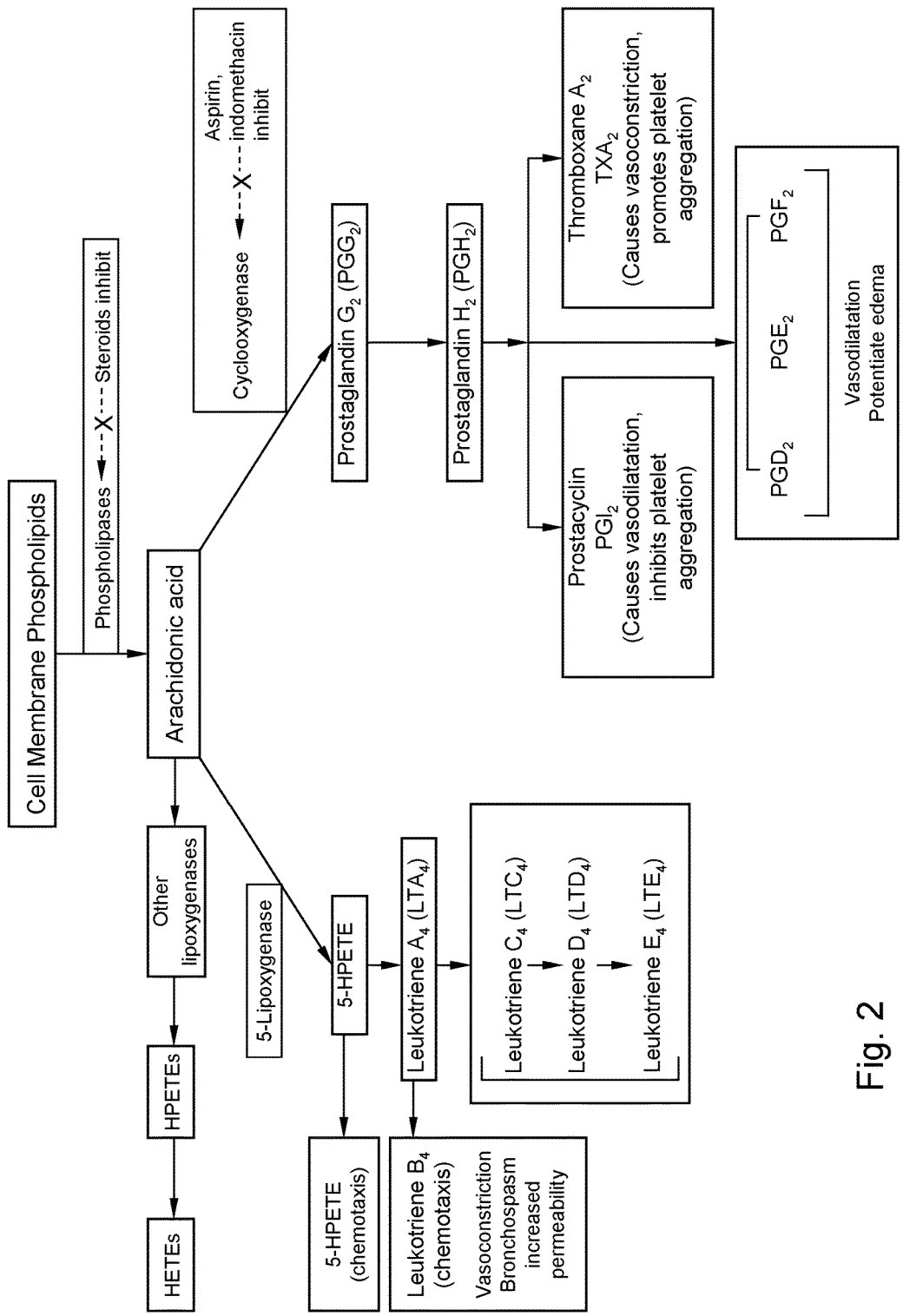
FIG. 2: Metabolites of cell-membrane phospholipids

The cellular calcium overload explained in the section "mineral homeostasis" activates the PLA2 enzymes to release the arachidonic acid (AA) from the cell membranes. Hence increased amounts of AA are converted via cyclooxygenase and 5-lopoxygenase into eicosanoid metabolites. The most important ones are depicted in FIG. 2.

This results in an increase of amongst others prostaglandins, thromboxanes and leukotrienes. These proinflammatory eicosanoids have all been linked to depression (Linnoila et al., 1983; Calabrese et al., 1986; Ohishi et al., 1998; Nishino et al., 1989; Song et al., 1998). We also demonstrated that mood disorders are correlated with increased PGE2, LTB4, and thromboxane B2 concentrations in blood as well as urine.

EPA competes with arachidonic acid for the cyclo-oxygenase enzyme system as is indicated in FIG. 1, inhibiting the production of proinflammatory eicosanoids derived from arachidonic acid (e.g. prostaglandins, leukotrienes and thromboxanes) which have been linked to depression.

DHA and EPA also inhibit the release of proinflammatory cytokines, such as interleukin-1 beta, interleukin-2, interleukin-6, interferon-gamma, and tumor necrosis factor alpha (Guixiang, 2007), which depend on eicosanoid release, and are also associated with depression. Further, omega-3 fatty acids affect brain-derived neurotrophic factor, which encourages synaptic plasticity, provides neuroprotection, enhances neurotransmission, and has antidepressant effects (Ikemoto, 2000)

Figure 3:
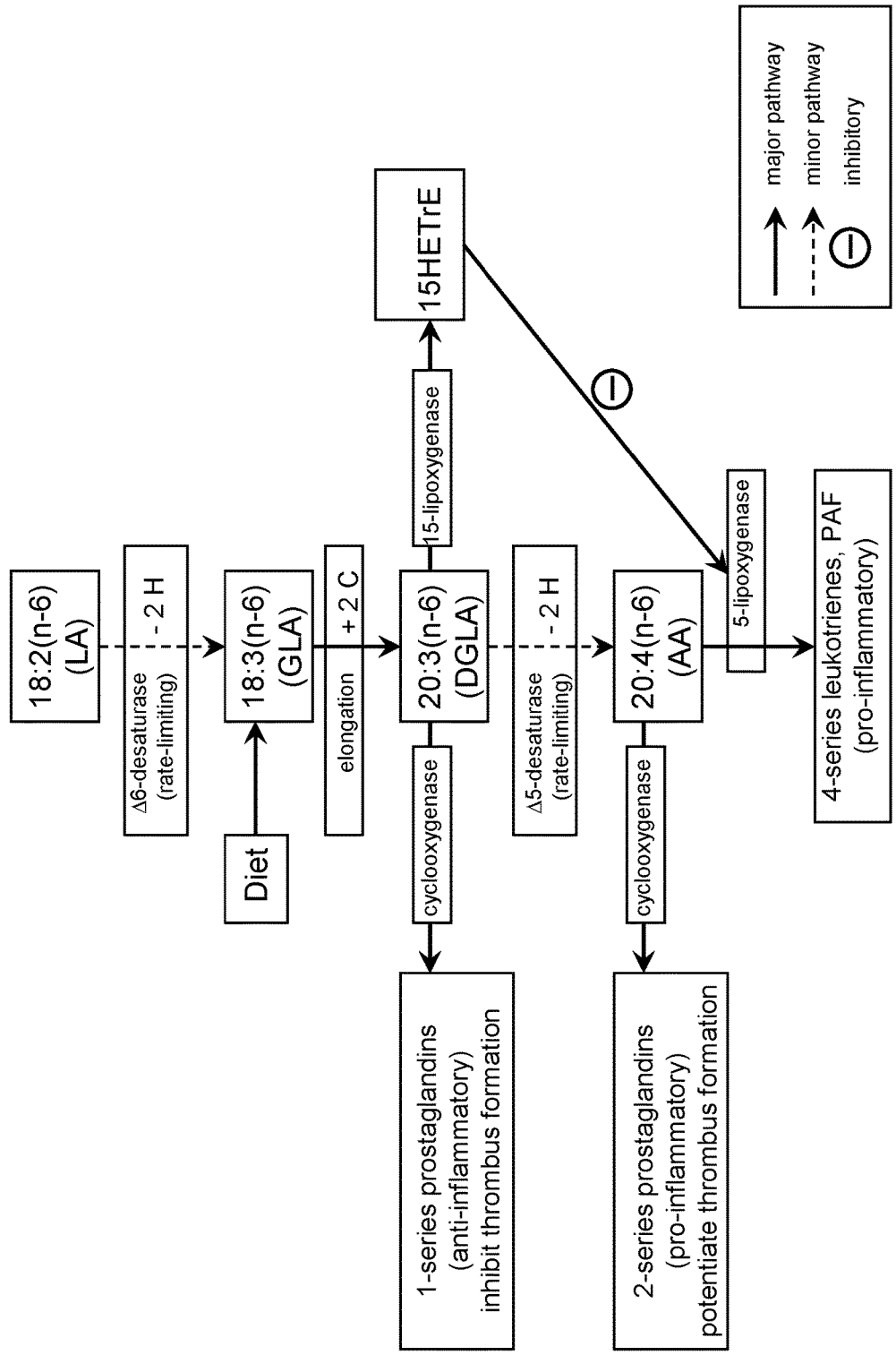
FIG. 3: GLA, DGLA and AA pathway
FIG. 4. List of markers and proposed marker sets that can be used on serum samples.

AA, DGLA and all cyclooxygenase & 5-lipoxygenase based metabolites thereof can be used as biomarkers for anti-inflammatory & pro-inflammatory disease states. The corresponding pathway is depicted in FIG. 3.

DGLA and it's metabolites being:
  Series-1 thromboxanes (thromboxanes with 1 double-bond), via the COX-1 and COX-2 pathways.
  Series-1 prostanoids, via the COX-1 and COX-2 pathways. (Yang-li, 1998)
  15-hydroxyl derivative that blocks the transformation of arachidonic acid to leukotrienes (Belch, 2006)

The effects of DGLA and its metabolites are anti-inflammatory. This is in marked contrast with the analogous metabolites of arachidonic acid (AA), which are the series-2 thromboxanes and prostanoids and the series-4 leukotrienes. In addition to yielding anti-inflammatory eicosanoids, DGLA competes with AA for COX and lipoxygenase, inhibiting the production of AA's eicosanoids.

An other metabolite is lipoxin. Lipoxins are a series of anti-inflammatory mediators. Lipoxins are short lived endogenously produced nonclassic eicosanoids whose appearance in inflammation signals the resolution of inflammation.

They are abbreviated as LX, an acronym for lipoxygenase (LO) interaction products. At present two lipoxins have been identified; lipoxin $A_4$ ($LXA_4$) and lipoxin $B_4$ ($LXB_4$). Lipoxins, as well as certain peptides, are high affinity ligands for the lipoxin $A_4$ receptor ($LXA4R$), which was first identified based on sequence homology as the formyl peptide receptor like receptor (FPRL1). Lipoxin signaling through the LXA4R inhibits chemotaxis, transmigration, superoxide generation and NF-κB activation. Similarly to the leukotrienes, $LXA_4$ will form the cysteinyl-lipoxins $LXC_4$, $LXD_4$ and $LXE_4$. At subnanomolar concentrations, $LXA_4$ and $LXB_4$ inhibit leukotriene-stimulated interactions of human neutrophils and endothelial cells.

Immune-Inflammation Hypothesis

Over the last two decades, new developments in psychiatric research have led to the hypothesis that inflammatory processes and neural-immune interactions are involved in the pathogenesis of major depression and that these might underlie some of the frequently observed serotonergic and adrenocortical correlates of MDD. This monocyte-T-lymphocyte or cytokine hypothesis of depression (Maes 1993, 1995a, 1995b, 1999; Schiepers et al., 2005) implies that pro-inflammatory cytokines, such as interleukin (IL)-1, tumor necrosis factor (TNF)-α and interferon (IFN)-γ, which act as neuromodulators, represent key factors in the (central) mediation of the behavioral, neuroendocrine and neurochemical features of depressive disorders (Schiepers et al., 2005).

The central action of cytokines may also account for the HPA-axis hyperactivity frequently observed in depressive disorders, because pro-inflammatory cytokines may cause HPA-axis hyperactivity by disturbing the negative feedback inhibition of circulating corticosteroids on the HPA axis (van West and Maes, 1999; Leonard, 2001; Schiepers et al., 2005; Maes et al., 2008; Maes, 2010). Another link might be via TNF-α and cortisol, both influencing the phosphorylation of transcription factor cAMP response element binding protein (CREB) in T-lymphocytes (Koch et al., 2009). Cytokines also influence monoaminergic neurotransmission, i.e. serotonin, norepinephrine and dopamine (Linthorst et al., 1995, Merali et al., 1997, Pauli et al., 1998 and Song et al., 1999, 2000; Lacosta et al., 2000).

They might also reduce tryptophan (TRP) availability through activation of the TRP-metabolizing enzyme indoleamine-2,3-dioxygenase (IDO). Thus, increased stimulation of IDO by cytokines might lead to depletion of serum TRP, which results in a significant reduction of 5-HT synthesis (Heyes et al., 1992; Stone and Darlington, 20021 Full Text via Cross Ref View Record in Scopus Cited By in Scopus (177) Stone and Darlington, 2002), thus compromising 5-HT neurotransmission. Activation of IDO by cytokines might also lead to increased production of neurotoxic kynurenines and isoquinolines. Characteristics of immune activation in MDD include increased serum levels of markers for immune cell activation (e.g. g. neopterin, PGE2 and soluble IL-2 receptors), higher serum concentrations of C-Reactive Protein (CRP) as well as increased release of pro-inflammatory cytokines, such as IL-1, IL-2 and IL-6 by activated macrophages and IFN-γ by activated T cells (Maes et al., 1995a,b; Maes, 1999; Irwin, 1999; Nunes et al., 2002).

In line with the immune-inflammation hypothesis of depression, the increase in plasma concentrations of the pro-inflammatory cytokines IL-1 and IL-6 observed in patients suffering from depression has been reported to correlate with the severity of MDD and with measures of HPA axis hyperactivity (Maes, 1995, 1999).

Neurogenesis and Neuroplasticity Hypothesis

Over the past decade, an increasing body of evidence has implicated neurotrophic factors in the pathogenesis of depression (Tanis et al., 2007)). FIG. 1 outlines some of the mechanisms underlying this hypothesis (Duman, R. S. et al., 1997, Arch. Gen. Psychiatry 54:597-608; Manji, H. K. et al., 2000, Mol. Psychiatry 5:578-593).

Stress, an important precipitant of depression, has been repeatedly shown to reduce neurogenesis and the expression of neurotrophic factor genes in the brain (Duman, 2004; Nibuya et al., 1995). Conversely, many antidepressant treatments stimulate neurogenesis and neurotrophic factor gene expression (Nibuya et al., 1995; Malberg et al., 2000). We are now aware that "long-term" (i.e., 30 days) antidepressant treatment results in sustained activation of cyclic adenosine 3-5-monophosphate (cAMP) in specific brain regions. Protein kinase A, which is stimulated by cAMP, phosphorylates the cAMP regulatory element binding protein (CREB). This protein then regulates and activates specific target genes, including the gene that codes for brain-derived neurotrophic factor (BDNF), a neuroprotective factor that stimulates hippocampal nerve growth.

Furthermore, depressed patients show increased cellular atrophy in limbic and cortical areas of the brain, consistent with decreased neurotrophic activity (Duman and Monteggia, 2006). MRI scans of patients with depression have revealed a number of abnormalities in brain structures compared with healthy controls. Despite some inconsistencies, meta-analyses have shown clear evidence for smaller hippocampal volumes and an increased number of hyperintensive lesions (Videbech et al, 1997, 2004). Furthermore, a series of brain-imaging studies consistently showed reduced neuronal activity in the dorsolateral prefrontal cortex that co-varied with the severity of the depression (i.e., the more severe the depression, the larger the prefrontal deficits) (Drevets, W. C., 1998, Ann. Rev. Med. 49:341-361). Thus, an updated hypothesis on the development of a depressive disorder might posit that stress-induced vulnerability in genetically susceptible people may induce a cascade of intracellular neuronal mechanisms that increase or decrease specific neurotrophic factors necessary for the survival and function of specific brain neurons. Besides, antidepressants, electroconvulsive therapy (Vaidya V. A. et al., 1999, Neuroscience 89:157-166) and depression-focused psychotherapy (Thase, M. E., 2001, Arch. Gen. Psychiatry 58:651-652) positively influence neuronal growth and regional brain metabolism.

A small fraction of neuronal stem cells of neuronal stem cells in the subventricular zone is capable of division and lifelong renewal and move to the hippocampus which is particularly involved in memory consolidation (REFs). A large body of evidence indicates that synaptic plasticity and renewal of neurons (neurogenesis) are both impaired in depression and that there is a connection with memory disturbances (REFs). It is also evident that effective antidepressant treatments have stimulatory effects on neuroplasticity, neurogenesis and cognition.

Among the neurotrophins, brain-derived neurotrophic factor (BDNF) has been most extensively studied in relation to depression. BDNF, a member of the "neurotrophic" family, was shown to promote survival of a subpopulation of dorsal root ganglion neurons, and was subsequently purified from pig brain (Barde, Y. A. et al., 1982, EMBO J. 1:549-533). The results of several meta-analyses on BDNF confirm significant correlations between serum BDNF levels and depressive state as well as successful antidepressant therapy (Sen et al., 2008; Bocchio-Chiavetto et al., 2010; Brunoni et al., 2008). Recent studies clearly demonstrate that serum levels of BDNF are significantly decreased in patients with MDD and that antidepressant treatments are capable of reversing this effect, indicating that serum BDNF is a potential biomarker of MDD and successful treatment (Bocchio-Chiavetto et al., 2010; Schmidt and Duman 2010; Dell'osso et al., 2010; Tadić et al., 2010).

It is important to note however that BDNF levels in serum are influenced by various determinants, such as age, sex, smoking status, urbanicity, etc. (Bus, B. et al., 2011, Psychoneuroendocrinol. 36:228-239).

Other neurotrophic factors that are involved in MDD belong to the group of HVEM, PEDF and midkine.

HVEM

Neurons are surrounded by immune cells of dendritic origin. Dendritic cells are present in all tissues in the body and have a supportive and protective role. Dendritic cells in the brain specialize into microglia cells. Microglia cells are present in the brain in approximately the same numbers as neurons. The protective functions of microglia are broad (against neuronal overstimulation, toxins, infectious agents) and also include the guidance of proper formation of connections between neurons. Microglia are essential for neurogenesis and neuroplasticity and can not be underestimated as player in MDD. The HVEM receptor in dendritic cells is part of the TNF superfamily of receptor (Tumor Necrosis Factor-Receptors) (De Trez & Ware, 2008). TNF-R are stimulated after stress, after immune activation and can elicit pro or anti neuroplasticity effects.

HVEM stimulation can be decisive in the "choice" of the cell between protective and detrimental responses. It is highly interesting that the TNF-R's blocking drug Etanercept ameliorates depressive symptoms (Uguz, Akman, Kucuksarac, & Tufekci, 2009).

PEDF

Adult stem cells are characterized by self-renewal and multilineage differentiation, and these properties seem to be regulated by signals from adjacent differentiated cell types and by extracellular matrix molecules, which collectively define the stem cell "niche." Self-renewal is essential for the lifelong persistence of stem cells, but its regulation is poorly understood. In the mammalian brain, neurogenesis persists in two germinal areas, the subventricular zone (SVZ) and the hippocampus, where continuous postnatal neuronal production seems to be supported by neural stem cells (NSCs). Pigment epithelium-derived factor (PEDF) is secreted by components of the murine SVZ and promotes self-renewal of adult NSCs in vitro. In addition, intraventricular PEDF infusion activated slowly dividing stem cells, whereas a blockade of endogenous PEDF decreased their cycling. This demonstrates that PEDF is a niche-derived regulator of adult NSCs and provide evidence for it's role in NSC maintenance (Katlin B. Massirer, 2010; Carmen-Ramírez-Castillejo, 2012)

Midkine

Midkine (MK) is a heparin-binding cytokine, and promotes growth, survival, migration and other activities of target cells. MK is strongly expressed during embryogenesis especially at the midgestation period, but is expressed only at restricted sites in adults. MK expression is induced upon tissue injury such as ischemic brain damage. MK is involved in inflammatory diseases by enhancing migration of leukocytes, inducing chemokine production and suppressing regulatory T cells. An aptamer to MK suppresses experimental autoimmune encephalitis (Muramatsu, 2001; Reiff, 2011).

In the current invention it has appeared that markers which relate to the various theories as indicated above may be used for the diagnosis of MDD, but also related diseases such as bipolar depression and anxiety disorders. In general, it is believed that the markers and marker sets of the present invention can be advantageously used for diagnosis of affective disorders.

As will be recognized by the skilled person, many of the above-mentioned markers have not yet been associated with affective disorders and especially depression. Therefore, especially the use of the markers HVEM, midkine, cGMP, cortisol, pregnenolone, and calprotectin for diagnosis of affective disorders in the urine, more preferably in the first morning urine of humans that are suspected of having an affective disorder is intended. Moreover, these compounds can also be used as markers for monitoring the progression of the disease or the progression of curing of the disease. In a similar way for blood samples zonulin, cAMP, HVEM, pregnonolone, midkine and calprotectin can be used as individual markers for the detection of affective disorders or for the monitoring of the progression of the disease or therapy effect thereon.

However, preferably a panel of two or more markers either measured in serum or in urine, or maybe both, is used to perform a reliable diagnosis of an affective disorder, preferably depression.

Such panels have recently been described in WO 2009/111595 and WO 2010/097631. In WO 2009/111595 the use of a panel of biomarkers comprising BDNF, IL-7, IL-10, IL-13, IL-15, IL-18, FABP, A1AT, B2M, factor VII, EGF, A2M, GST, RANTES, TIMP-1, PAI-1thyroxine and cortisol, or various subsets of this panel, has been described. Another panel disclosed in this application consists of ACTH, BDNF, cortisol, dopamine, IL-1, IL-13, IL-18, norepinephrine, TSH, AVP and CRH, and additional neuropeptide Y and platelet associated serotonin, or subsets thereof.

In WO 2010/097631 a panel with overlapping biomarkers is presented, consisting of IL-17, IgA, cortisol, 1 apolipoprotein A, IL-6, complement 3, Factor VII, SAP, B2M, ICAM-1, IL-1, TNF-alpha, MIF, angiotensinogen, NrCAM, CD40, CA125, HCC4, eotaxin 3, VEGF, haptoglobin, IL-1 alpha, apolipoprotein H and TIMP-1, and additionally one or more of AFP, Glutathione S-transferase alpha, eotaxin, toxoplasma, IGF-BP2, BDNF, SOD and IL-15.

However, in none of these applications, evidence is given whether the indicated panels indeed are able to give a reliable diagnosis of depression.

Thus, there still remains need for further markers for diagnosis of mood disorders, such as depression.

In this application the term 'biomarker' is used for a distinctive biological or biologically derived indicator of a process, event or condition. Biomarkers can be used in methods of diagnosis, e.g. clinical screening, and prognosis assessment and in monitoring the results of therapy. They also can be used for identifying patients that are most likely to respond to a certain treatment, for drug screening and for development in medicine. Biomarkers and their uses are therefore valuable for identification of new drug treatments and for discovery of new targets for drug treatment. Further they are valuable for exploring dosage regimes and drug combinations.

For the purpose of clarity and a concise description biomarkers are described herein as part of the same or separate embodiments, however, it will be appreciated that the scope of the invention may include embodiments having combinations of all or some of the biomarkers described.

It should be clear to the skilled person that mood disorders that have a complicated and yet not (completely) understood ontogenesis are hard to diagnose. Current diagnosis is based, as has been discussed in the introduction, on behavioral and psychological grounds. In the literature there is evidence that many factors are involved and play a role in mood disorders. Yet, the focus for developing a diagnosis based on biomarkers has thus far focused on single assays.

In this respect, the current invention adds more markers to the existing panels of markers that have been disclosed in the prior art. The present inventors have found that several compounds may be used as a marker for (helping in) diagnosing affective disorders, preferably depression. It has appeared, as is shown in the experimental section, that these individual markers already are able of discriminating between healthy and affected persons, although there is an overlap between the values of the two groups.

These individual markers are Lox-1, HVEM, midkine, pregnenolone, and calprotectin in serum or in urine. When only considering measurements in urine, the markers cortisol and substance P, and cGMP may be added to the list. In a similar way for blood samples zonulin and cAMP can additionally be used as individual marker for the detection of affective disorders or for the monitoring of the progression of the disease or therapy effect thereon.

To make diagnosis more reliable, it is preferred to add more than one marker into the assay. As has been discussed in the introduction, there are several hypotheses on the cause and development of mood disorders, especially depression. The idea behind the invention is to select markers that represent different of these hypotheses, to get a panel of complementary markers.

Figure 4:
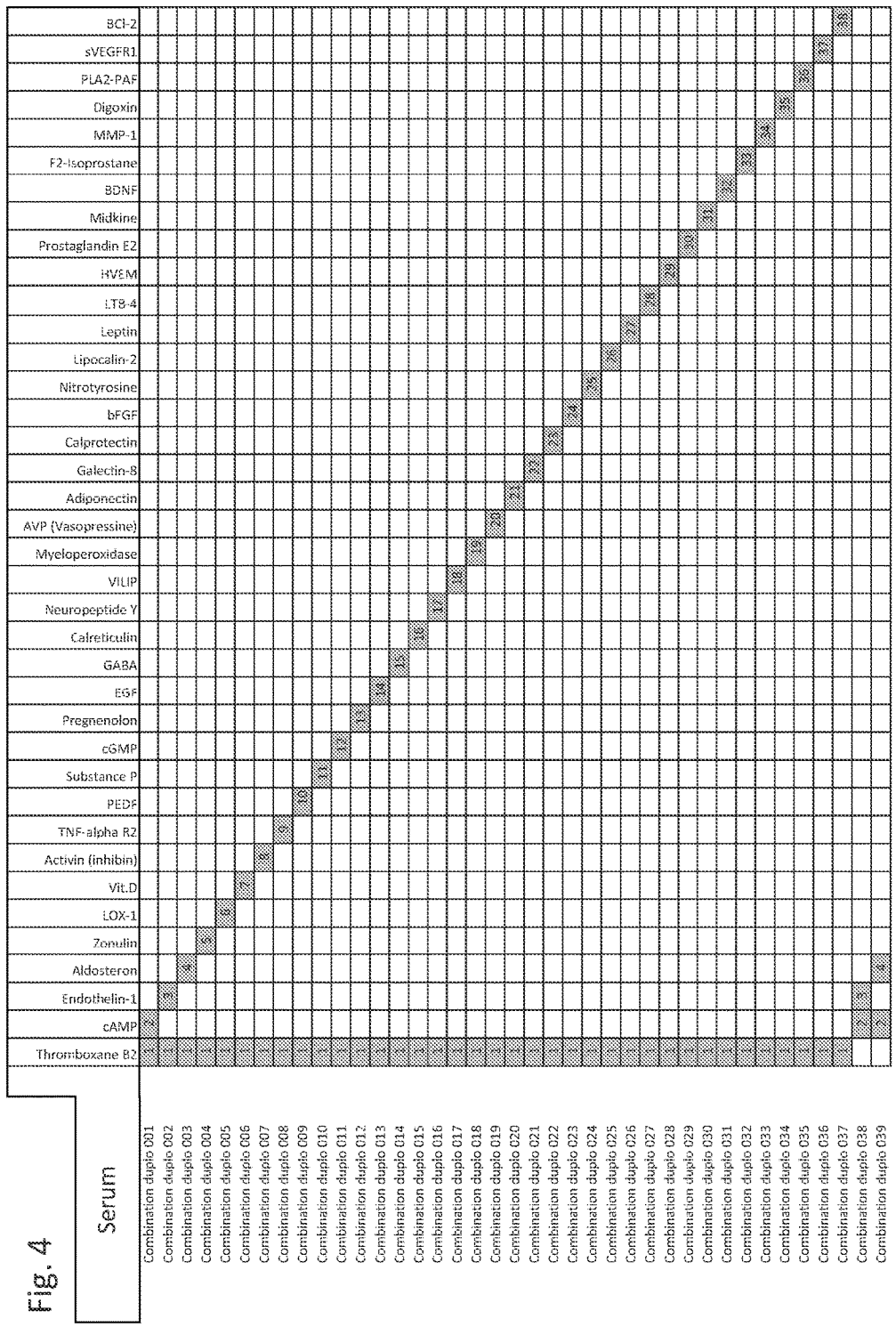
Figure 5:
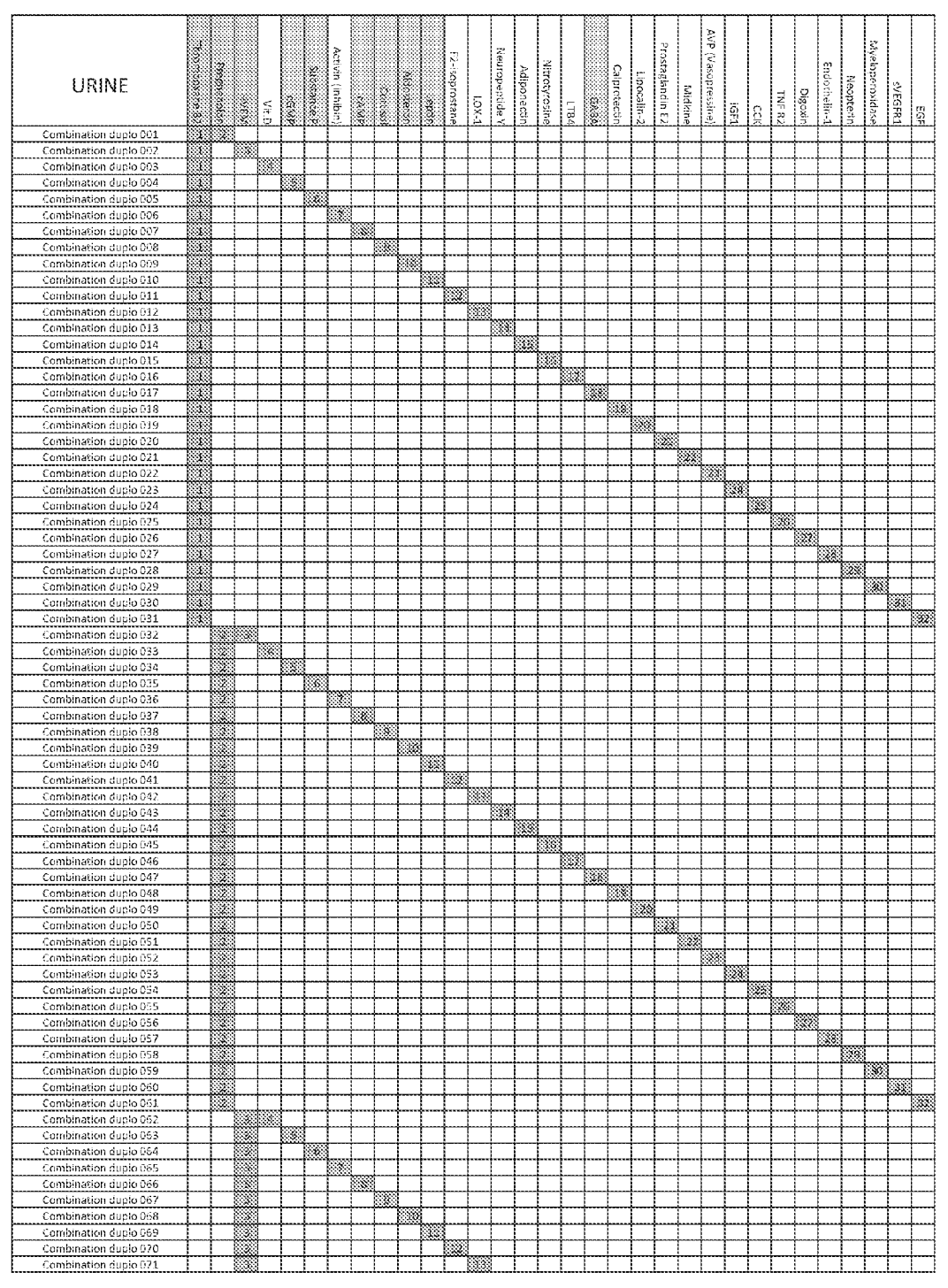
Figure 5:
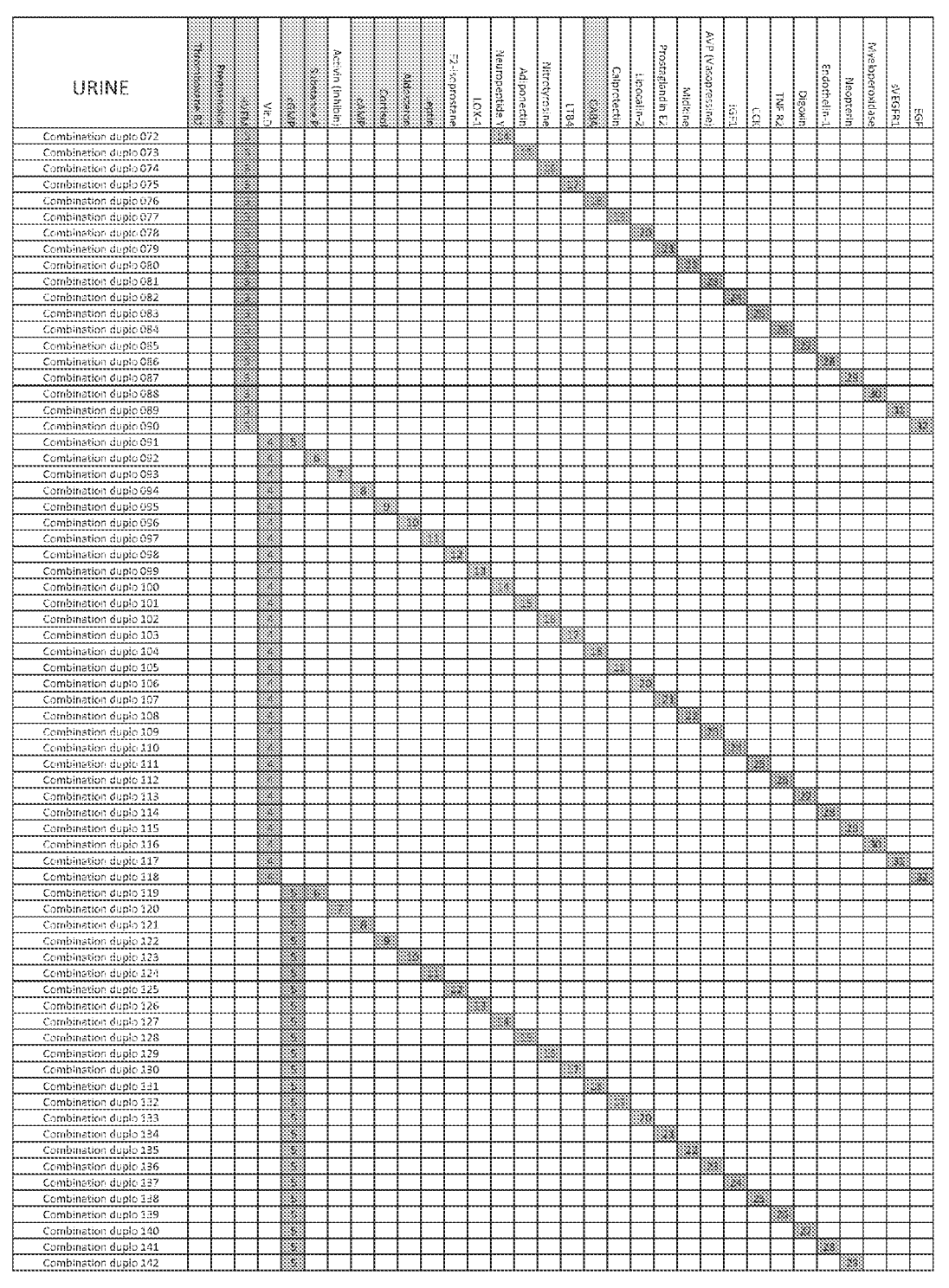
Figure 5:
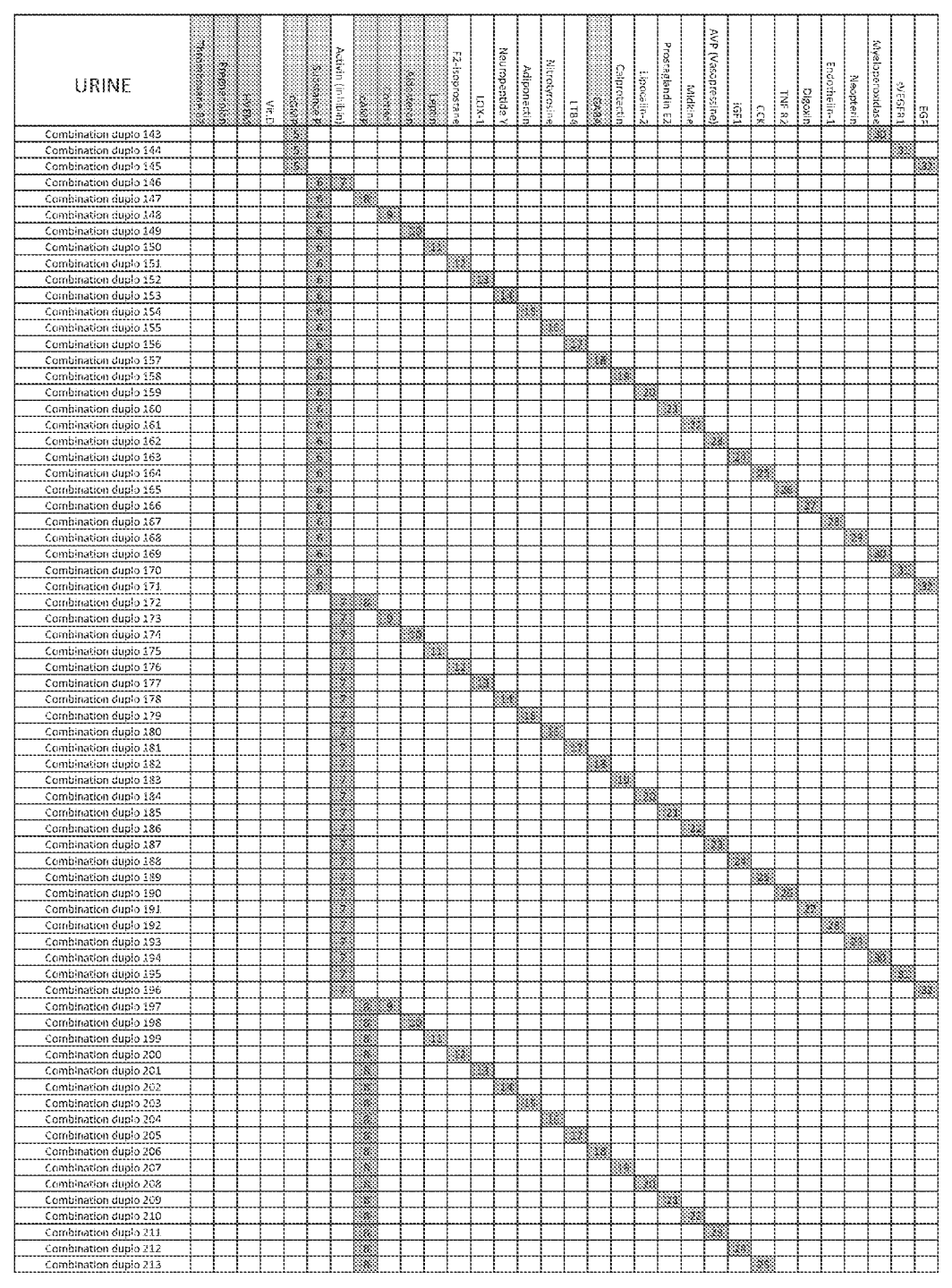
Figure 5:
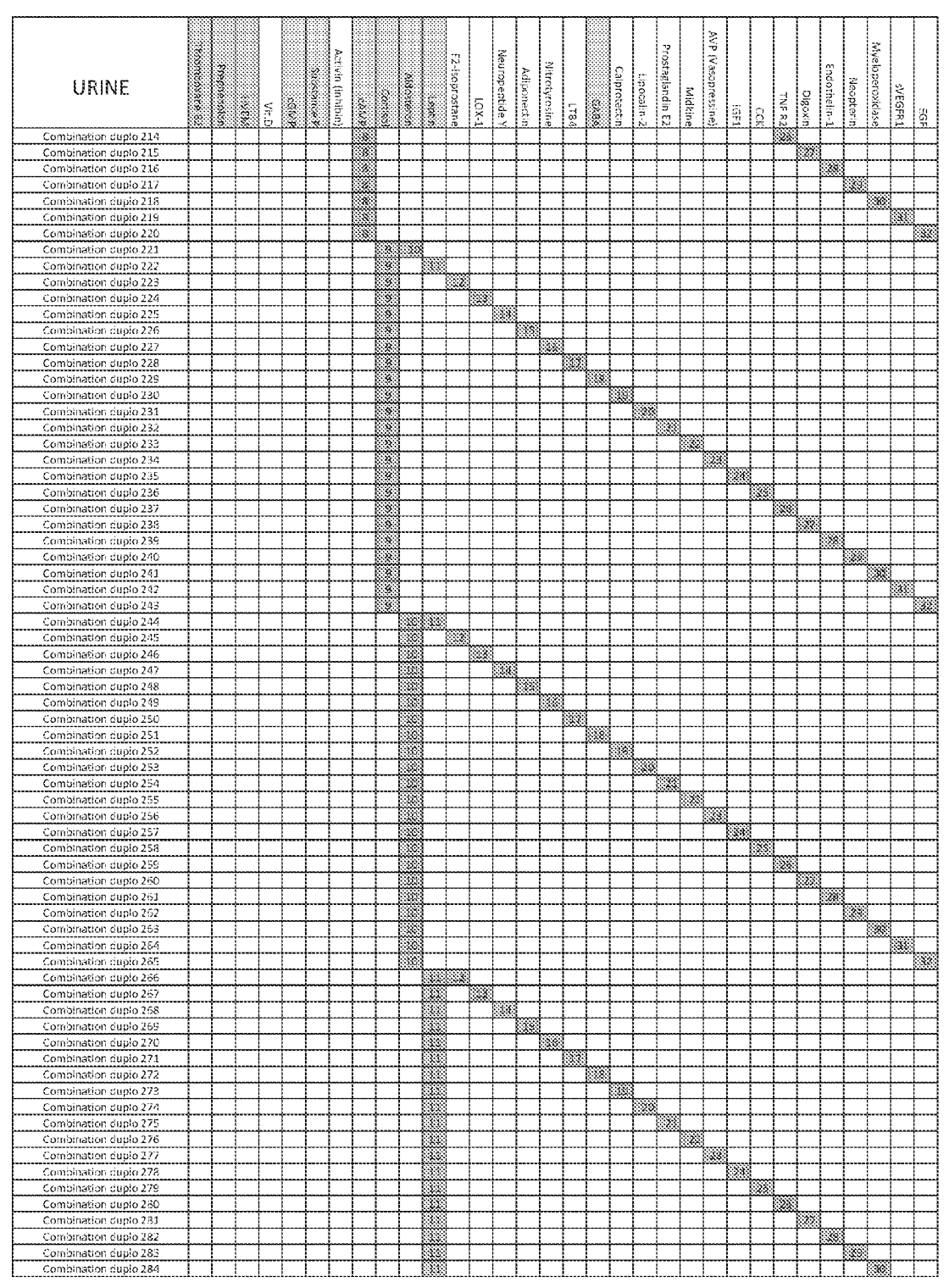
Figure 5:
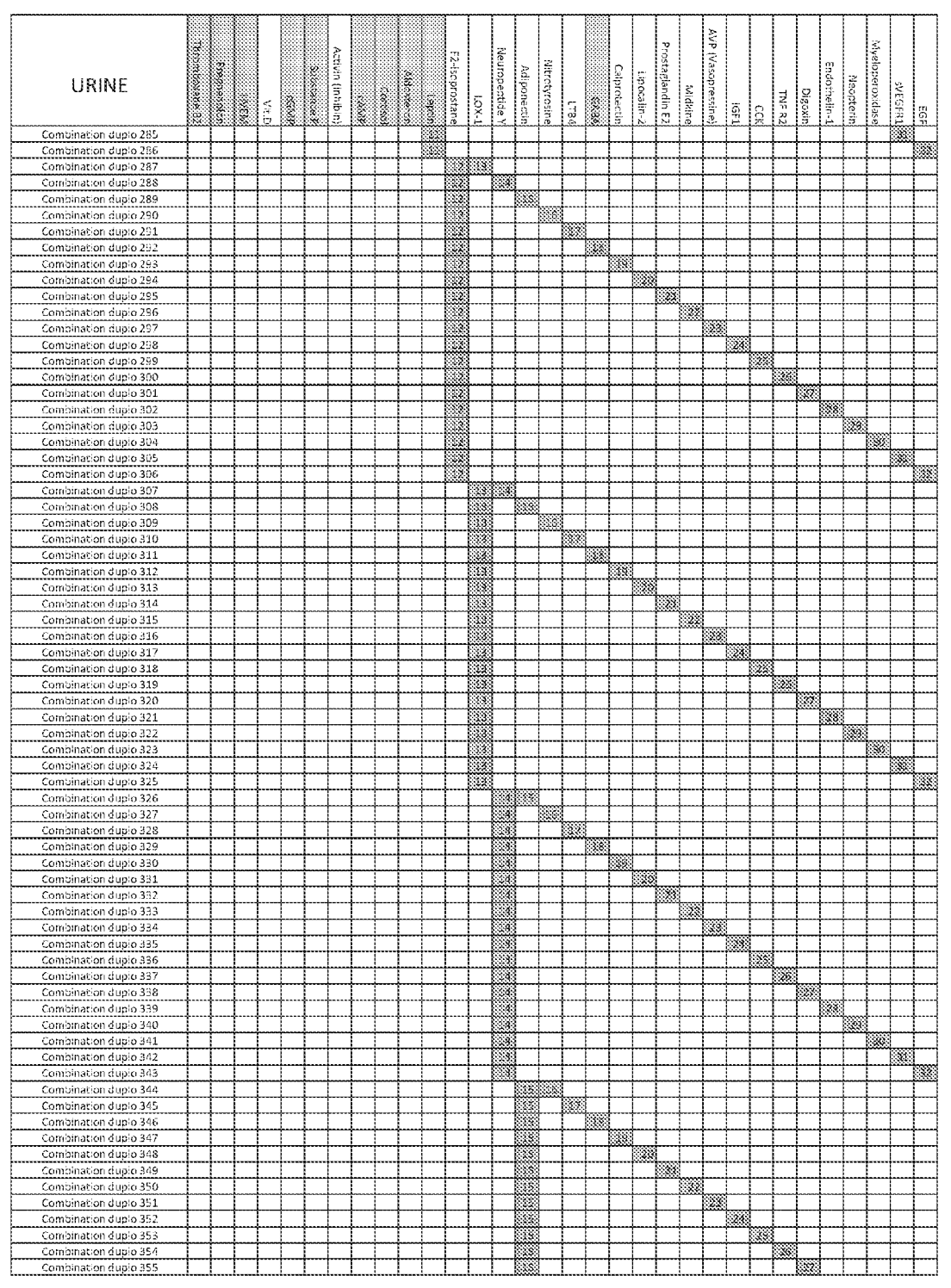
Figure 5:
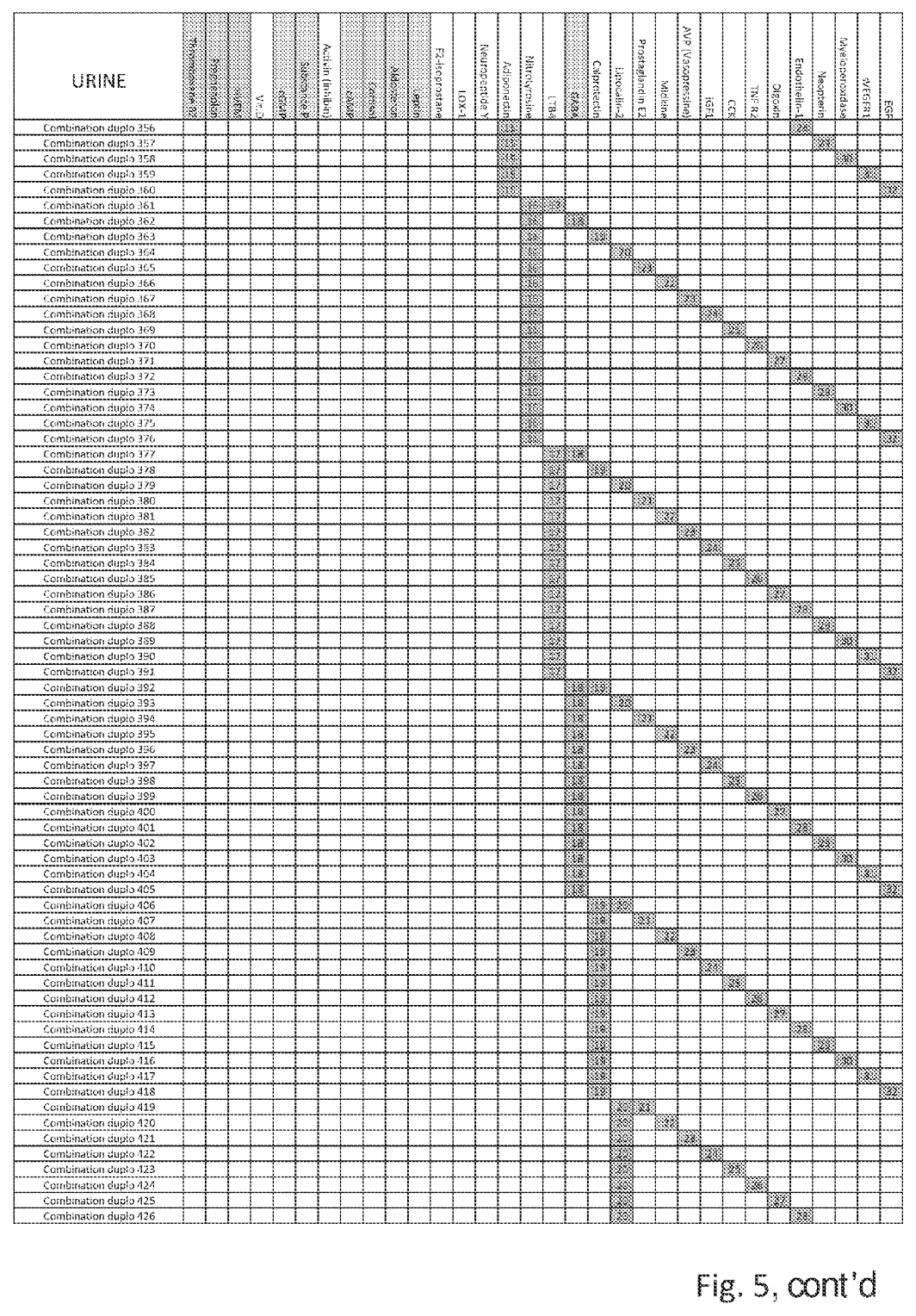
Figure 5:
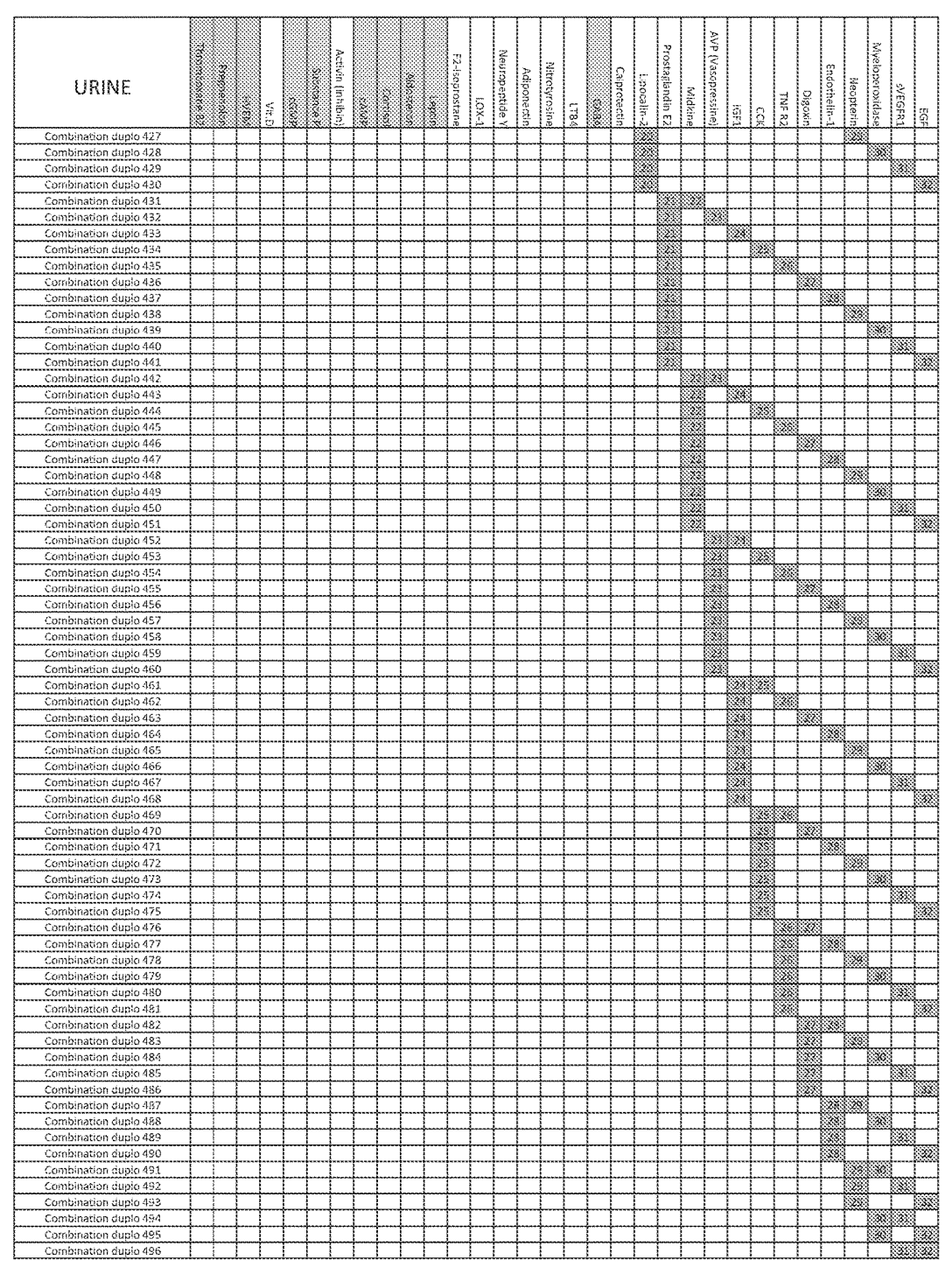

In FIGS. 4 and 5 for respectively serum samples and urine samples it is indicated which groups (sets of markers) are deemed to be applicable for the diagnosis of affective disorders, especially depression, in total for serum with 38 markers and for urine with 32 markers. As can be seen each time a set containing only 2 markers is indicated. As such, the present invention covers the use of a set of at least two markers as chosen from the group of sets indicated in the FIGS. 4 and 5 for diagnosis of affective disorders, especially depression. However, such a set may optionally be complemented with any number of the other markers listed in the Figure. Accordingly, a set of markers may comprise 2 markers as indicated by the combinations mentioned in FIGS. 4 and 5, but may also comprise 3 markers, where the third marker is chosen from any of the markers listed in FIGS. 4 and 5. Alternatively, it may comprise 4 markers, 5 markers, 6 markers and up to 28 markers selected from the markers mentioned in FIGS. 4 and 5.

Further, a set of markers which are applicable for the current invention may consist of a combination of the above mentioned "serum" markers and "urine" markers.

Detection and/or quantification of these biomarkers may be performed using an immunological method, involving an antibody, or fragment thereof, capable of specific binding to the biomarker. Suitable immunological methods include sandwich immunoassays, such as sandwich ELISA, in which the detection of the biomarkers is performed using two antibodies which recognize different epitopes on the biomarker; radioimmunoassay (RIA), direct, indirect or competitive enzyme linked immunosorbant assays (ELISA), enzyme immunoassays (EIA), fluorescence immunoassays (FIA), chemiluminescent immunoassays, western blotting, immunoprecipitation and any particle based immunoassay (e.g. using gold, silver or latex particles, magnetic particles, or Q-dots). Immunological methods may for example be performed on a microtitre plate or on test strips. It is also possible to perform the analysis with concurrent lab-on-a-chip techniques. These immunoassays are commercially available. In the exemplary part of the present application it has been indicated for each biomarker measured in the present application from which vendor the assay that is the basis of the present invention has been used.

However, the invention is not limited to immunoassays. Analysis of the biomarkers in the sample of the patient may be carried out with chemical analytical methods (like mass spectrometry, MALDI-TOF, micro-Raman spectrometry), with magnetic radio imaging, flow cytometric analyses and all other quantitative analysis systems that are suitable for detecting proteins in fluids. The assays may also be performed on nucleic acids that encode for the (protein) markers or for enzymes that are in the biosynthesis pathways of non-protein markers. Such assays are preferably RT-PCR assays in which mRNA is measured from the sample. In such a case, the sample may be any cell material derived from the body. Also receptor-based assays, using a receptor that is normally present in a biological system for the mentioned biomarker, as analytical tool may be used. Of course also RT-PCR assays for the receptor encoding nucleic acid, are usable. Apart from RT-PCR also hybridization techniques (northern blotting, microarray hybridization etc.) and sequencing techniques can be used to determine DNA expression of said (protein) markers and/or their receptors.

Recently, scientists have focused on epigenetic variation, and specifically changes in DNA methylation as a promising class of biomarker that may apply to a range of disorders (Petronis, 2010; Portela&Esteller, 2010). Methylation refers to the addition of methyl ($CH_3$) groups to the cytosine of CpGs in their promoter regions, and in most normal cells these CpG "islands" are unmethylated. Methylation of CpG islands in promoter regions can dramatically alter gene expression. For many years research focused heavily on the role of DNA methylation in cancer, but scientists have increasingly focused on the role of DNA methylation in psychiatric disorders (Tsankova et al., 2007; Bredy et al., 2010). In fact, the mechanisms of action for some existing psychiatric medications may involve epigenetic alterations (e.g. valproic acid). Epigenetic changes have been linked to changes in gene regulation in neurons and downstream processes such as memory and cognition. The overall conclusion is that epigenetic changes may play an important role in terms of long-term neurological changes (or "molecular and cellular memory"). Thus, DNA methylation can serve as important biomarker of treatment target.

The assays that are useful in the present invention are preferably quantitative assays, in which the concentration of biomarker in the sample can be determined. This can—in principle—be achieved with all of the above mentioned detection methods. While interpreting the results of such an assay, various determinants such as sex, age, smoking status, urbanicity, food and alcohol intake should be taken into account.

For all of these markers commercial immunoassays are available. These markers can all be assayed in body fluids, but it is also possible that for some biomarkers one type of body fluid is preferred. Thus if two or more markers are tested, it can be the case that one marker is tested in the blood and the other marker is tested in the urine and a third is tested on nucleic acids derived from cell material. While interpreting the results of such an assay, various determinants such as sex, age, smoking status, urbanicity, food and alcohol intake should be taken into account.

Preferably, a panel of markers will be provided in an assay for the diagnosis of a mood disorder, preferably depression, in a patient, wherein this panel comprises markers reflecting the following groups:

markers reflecting the mineral homeostasis hypothesis: PTH, AVP and its receptors (V1a, V1b), cAMP, TRPM7 digoxin, TRPM6, RACK-1, estradiol, REA, substance P and its receptor NK1, EGF and its receptors ERBB1-4, aldosteron and its receptor (MRC) and all substances which are known to influence the excretion of aldosteron like angiotensin I and II and their receptors (AT1, AT2), ACTH and its receptor (MC2), potassium and rennin.

markers reflecting endothelin dysfunction and oxidative stress chosen from: oxLDL and its receptor LOX-1, nitrotyrosine, F2-isoprostane, endothelin-1 and its receptors (Eta,ETb), elastin/desmosine.

markers reflecting tight junction & leaky gut hypothesis: zonulin proteins and zonula occludens toxin_(zot); LIGHT and_lymphotoxin ß receptor (LTßR)

markers reflecting pro-inflammatory hypothesis chosen from: all phospholipase A2 enzymes, PAF/PLAF; and all downstream components of arachidonic acid as well as dihomo-gamma-linolenic acid pathway like but not limited to PGA2, PGE2 and its receptors, Tromboxane B2 and its receptor TP, Prostacyclin, PGF2 and PGD2; downstream 5-HPETE and other HPETEs derivatives like but not limited to 5-HETE, LTB4 and its receptors (BLT1, BLT2 ect), LTC4, LTD4 LTE4; cysteinyl leukotriene receptor type 1, lipoxin (LXA4, LXB4), lipoxin $A_4$ receptor, PGE1, PGA1, PGH1-15OH triene;

markers reflecting the immune-inflammation hypothesis chosen from:

lipocalin-2, TNF alpha, TNF beta, TNF alpha receptor type 1+2, HVEM, calprotectin, il-6 and its receptor, il-1 and its receptor, myeloperoxidase, galectin-8 and neopterin.

markers reflecting the neurogenesis hypothesis chosen from BDNF and its receptors TrkB and LNGFR, midkine and its receptor RPTPξ, bFGF and its receptor HVEM and PEDF.

markers reflecting a (change in) energy state: leptin and its receptor (LEP-R), adiponectin and its receptors (ADIPOR1, ADIPOR2 and CDH13)

other markers chosen from: vitamin D and its receptor (VDR), cortisol and its receptor (GCR), annexin-1, pregnenolone and its receptor (GCR), GABA, VILIP-1, Neuropeptide Y, MMP-1, BCL-2, Calreticulin, activin/inhibin cGMP and compounds from the NO-cGMP pathway including all agents which are known to influence the excretion of cGMP like atrial natriuretic peptide, brain natriuretic peptide and c-type natriuretic peptide; vasoactive intestinal peptide and calcitonin gene-related peptide, nitric oxide synthase (endothelial NOS, eNOS, neuronal NOS, nNOS) and l-arginine;

According to the invention a set of markers that can be used in an assay to diagnose an affective disorder, preferably MDD, bipolar depression or anxiety may be a set of two markers chosen from the above groups, which group may be supplemented by any marker from the above-mentioned groups. For testing in urine, preferably, the set of two markers is chosen from a group of 32 markers, comprising activin, cAMP, aldosteron, digoxin, lipocalin, neopterin, LTB4, TNF alpha receptor 2, HVEM, PGE2, thromboxane B2, LOX-1, nitrotyrosine, F2-isoprostane, midkine, IGF, endothelin-1, c-GMP, GABA, vitamin D, cortisol, pregnenolone, substance P, EGF, calprotectin, leptin, myeloperoxidase, neuropeptide Y, CCK, sVEGFR1, AVP and adiponectin. For testing in serum, preferably, the set of two markers is chosen from a group of 38 markers comprising activin, cAMP, aldosteron, lipocalin, TNF alpha receptor 2, HVEM, PGE2, thromboxane B2, LOX-1, nitrotyrosine, F2-isoprostane, BDNF, PEDF, midkine, endothelin-1, c-GMP, GABA, vitamin D, pregnenolone, substance P, EGF, zonulin, calprotectin, VILIP, leptin, AVP (vasopressine), Neuropeptide Y, MMP-1, bFGF, digoxin, BCL-2, calreticulin, myeloperoxidase, LTB4, PLAF, sVEGFR1 and adiponectin.

Next to the above given overview of hypotheses for the ontogenesis of depression and compounds that play a role in there, for some of these markers the relevance with respect to involvement and possibly diagnosis of depression has been presented in the literature. A large, but far from complete list of the relevant literature is appended hereinafter.

Further, the rationale for using lipocalin-2 as marker can be derived from co-pending application NL 2007112.

As indicated above, the markers can be used to affirm a diagnosis based on psychological and behavioral criteria. For each of the markers it can be indicated whether or not the level measured is indicative of the presence of a mood disorder, such as depression. Information to that respect can be found in the cited literature and the practical application of this knowledge is demonstrated in the experimental part of the present application Obviously, the more markers are used in the panel, and consequently, the more markers that are tested with a level that would suspect disease, the more reliable the diagnosis of depression can be made.

Of course, if all or nearly all markers of the set that has been used respond positive for depression, the diagnosis should be considered definitive. Alternatively, a diagnostic score can be calculated as is exemplified on pages 8 and 9 of WO 2009/111595.

On basis of the initial results with the markers, as presented in the experimental section below, it has been established that a preferred embodiment of a panel of markers for serum/plasma assays which may be used for a diagnosis of a mood disorder, preferably depression, with a high confidentiality, comprises the markers TNF-R2, cortisol, thromboxane, endothelin, leptin and vitamin D. In order to further increase the confidentiality of the diagnosis, this set may be extended with the group of biomarkers consisting of calprotectin, cAM, zonulin and substance P. For a still further increase of the confidentiality the assay may be further extended with the markers BDNF, midkine, nitrotyrosine, LTB4, neuropeptide Y, telomerase and aldosterone.

Similarly, for testing in urine only a set of markers which provides a reliable diagnosis consists of cGMP, cortisol, calprotectin, thromboxane, aldosterone, HVEM and substance P. A further improvement in the confidentiality of the diagnosis can be achieved to further include the biomarkers leptin, LTB4, isoprostane and midkine. An even further increase of the correctness of the diagnosis can be achieved by further including the biomarkers cAMP, endothelin, TNF-R2 and neuropeptide Y.

When mixing both serum/plasma biomarkers and urine biomarkers, the minimal set of markers that is able to provide with a reliable diagnosis (significance p<0.00001) consists of the biomarkers TNF-R2 (s), cortisol (s), thromboxane (s), leptin (s), endothelin (s), cGMP (u), cortisol (u), aldosterone (u), thromboxane (u), HVEM (u) and substance P (u), in which the suffix (s) or (u) indicates whether this marker should be measured in serum/plasma (s) or in urine (u). In order to increase the precision of the diagnosis, this set of biomarkers may be extended with the group of Vitamin D (s), cAMP (s), zonulin (s), substance P (s) and calprotectin (u). A further increase in precision may be gained by further combining the above mentioned marker sets with a further set of markers, comprising calprotectin (s), leptin (u), LTB4 (u), isoprostane (u) and midkine (u).

The above-mentioned groups are also listed in Table 4 below.

While interpreting the results of such an assay, various determinants such as sex, age, smoking status, urbanicity, food and alcohol intake should be taken into account. It can also be deduced from the cited literature (e.g. Bus et al., 2010) that the presence of a marker is related to a factor such as sex, where in males a higher concentration is found than in females, or to a factor such as age, where in elderly persons a higher level of a marker is found than in younger persons. The measured values should of course be interpreted in the light of these correlations, which are known to the skilled person, as is demonstrated from the cited literature herein.

Preferably, the assay, when performed on urine, more preferably on the first morning urine sample, also includes a simultaneous assay for creatinine. Creatinine is one of the byproducts of protein metabolism. Under normal conditions it is present in the blood and is excreted as a final metabolite in the urine. Urine creatinine levels are routinely used as part of kidney function diagnosis. In particular, altered creatinine levels in urine are indicative of kidney diseases such as acute or chronic nephritis, nephrosis, and the like. Because normative values for creatinine excretion have been established, urine creatinine levels are also useful for correction of assays for other compounds, as they document the adequacy of the urine collection for such assays. In particular, the creatinine correction can be used to correct for urine dilution, thus giving a possibility to standardize measured concentrations irrespective of the water content of the urine and/or the time of the day when the urine was produced. Further, changes in renal function which influence rates of excretion, can be corrected by measurement of creatinine in urine. Any values given in the experimental part for assays done on urine have been corrected by measurement of creatinine.

The biomarkers of the present invention or such a replacement molecule are recognised by 'biosensors', which may comprise a ligand or ligands capable of specific binding to the biomarker. Such biosensors are useful in detecting and/or quantifying the biomarker, preferably in quantifying.

Especially useful biosensors are antibodies. The term 'antibody' as used herein may comprise polyclonal, monoclonal, bispecific, humanised or chimeric antibodies, single chain antibodies, Fab fragments and F(ab')2 fragments, fragments produced by a Fab expression library, anti-idiotypic antibodies and epitope-binding fragments. The term 'antibody' also refers to immunoglobulin and T-cell receptor molecules, i.e. molecules that contain an antigen-binding site that specifically binds an antigen. The immunoglobulin molecules can be of any class (e.g. IgA, IgD, IgE, IgG and IgM) or subclasses thereof. If the biomarker is a nucleic acid, a specific probe can be used as 'biosensor'. Preferably in such a case, the target DNA is first amplified in a PCR reaction with suitable primer sequences.

The identification of the biomarkers that are specific for a mood disorder, especially depression and more particularly major depressive disorder is key to integration of diagnostic procedures and therapeutic regimes. Appropriate diagnostic tools such as biosensors can be developed in methods and uses of the invention; and detection and quantification of the biomarker can be performed using a biosensor in a microanalytical system, a microengineered system, a microseparation system, an immunochromatography system or other suitable analytical devices (such as Raman or mass spectrography and the like). The biosensor may be incorporated in an immunological method for detection of the biomarker(s), or via electrical, thermal, magnetic, optical (e.g. hologram) or acoustic technologies. Using these techniques, it is possible to detect the target biomarker(s) at the anticipated concentrations found in biological samples. Thus, according to a further aspect of the invention there is provided an apparatus for diagnosing or monitoring a mood disorder, especially depression and more particularly major depressive disorder which comprises one or more biosensors in a microanalytical, microengineered, microseparation and/or immunochromatography system configured to detect and/or quantify any of the biomarkers defined herein.

The biomarker(s) of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitized to react specifically with the biomarker. On exposure, the biomarker reacts with the polymer leading to an alteration in the image displayed by the hologram.

The test result read-out can be a change in the optical brightness, image, color and/or position of the image. For qualitative and semi-quantitative applications, a sensor hologram can be read by eye, thus removing the need for detection equipment. A simple color sensor can be used to read the signal when quantitative measurements are required. Opacity or color of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, methods for detection of one or more biomarkers according to the invention combine biomolecular recognition with appropriate means to convert detection of the presence or quantity of the biomarker in the sample into a signal.

Biosensors to detect one or more biomarkers can also be detected by acoustic, plasmon resonance, holographic and microengineered sensors. Imprinted recognition elements, thin film transistor technology, magnetic acoustic resonator devices and other novel acousto-electrical systems may be employed for detection of the one or more biomarkers of the invention.

Methods involving detection and/or quantification of one or more biomarkers of the invention can be performed on bench-top instruments, or can be incorporated onto disposable, diagnostic or monitoring platforms that can be used in a non-laboratory environment, e.g. in the physician's office or at the patient's bedside. Suitable platforms for performing methods of the invention include "credit" cards with optical or acoustic readers. The sensor systems can be configured to allow the data collected to be electronically transmitted to the physician for interpretation and thus can form the basis for remote diagnosis.

Methods of the invention can be performed in array format, e.g. on a chip, or as a multi well array. This enables testing for several biomarkers or for only one biomarker in multiple subjects or samples simultaneously. Methods can be adapted into platforms for single tests, or multiple identical or multiple non-identical tests, the last especially in the case if urine-based markers are combined with serum-based markers, and can be performed in high throughput format. Methods of the invention may comprise performing one or more additional, different tests to confirm or exclude diagnosis, and/or to further characterize a condition.

A kit for diagnosing or monitoring a mood disorder, especially depression and more particularly major depressive disorder, or predisposition thereto is provided. Suitably a kit according to the invention may contain one or more components selected from the group: a biosensor specific for the biomarker or a molecule upstream or downstream in the biological pathway for that biomarker, where the biomarker is one of the biomarkers provided herein; one or more controls; one or more reagents and one or more consumables; optionally together with instructions for use of the kit in accordance with any of the methods defined herein.

The identification of biomarkers for mood disorders, especially depression and more particularly major depressive disorder permits integration of diagnostic procedures and therapeutic regimes. Currently effectiveness of drug treatment or psychotherapy is difficult to test, and it has thus far not been possible to perform rapid assessment of therapy response. Traditionally, many anti-depressant therapies require treatment lasting weeks to months for a given therapeutic approach. Detection of a biomarker of the invention can be used to screen subjects prior to their participation in clinical trials. The biomarkers provide the means to indicate therapeutic response, failure to respond, unfavourable side-effect profile, and degree of medication compliance. The biomarkers may be used to stop treatment in non-responders at a very early stage. They can also be used to fine-tune dosage, minimize the number of prescribed medications, and to reduce the delay in attaining effective therapy. Thus by monitoring a biomarker of the invention, patient care can be tailored precisely to match the needs determined by the disorder and the pharmacogenomic profile of the patient. The biomarker can thus be used to titrate the optimal dose and to identify a positive therapeutic response.

Biomarker-based tests, such as provided by the present invention, provide a first line assessment of 'new' patients, and provide objective measures for accurate and rapid diagnosis, in a time frame and with precision, not achievable using the current subjective measures. Furthermore, diagnostic biomarker tests, such as provided by the present invention, are useful to identify family members or patients at high risk of developing major depressive disorder. This permits initiation of appropriate therapy, or preventive measures, e.g. managing risk factors. These approaches are recognized to improve outcome and may prevent overt onset of the disorder.

Biomarker monitoring methods, biosensors and kits are also vital as patient monitoring tools. If pharmacological treatment is assessed to be inadequate, then therapy can be reinstated or increased; a change in therapy can be given if appropriate. As the biomarkers are sensitive to the state of the disorder, they provide an indication of the impact of drug therapy.

Diagnostic kits for the diagnosis and monitoring of a mood disorder, preferably depression, most preferably major depressive disorder, are described herein. A method of diagnosis or monitoring the biomarkers may comprise quantifying the biomarker in a sample from the patient and comparing the level of the biomarker present in said sample with one or more controls. For monitoring, the control may be a test sample of the same patient at an earlier point in time.

Preferably, the diagnosis for the presence of a mood disorder in a patient according to the present invention is used to confirm a suspicion of a mood disorder, such as depression. This means that preferably the patient is already suspected of having a mood disorder at the moment that de the assay for one or more of the biomarkers is performed. In this respect, the invention can be considered as a method for enhancing the diagnosis of depression.

One of the main advantages of the present invention is that it provides an easy and reliable way to monitor progress of the disease and/or effectiveness of a therapy. To this end, the values for one or more of the above identified biomarkers for a subject are determined at a certain moment (null-value) and after an amount of time this procedure is repeated. Over the time, several repeat measurements can be performed. In the mean time therapy can e.g. be started or changed. Change(s) in the levels of biomarker will then indicate the effectiveness of the therapy or the progress of the disease.

Suitably, the time elapsed between taking samples from a subject undergoing monitoring will be several days, a week, two weeks, a month, several months or longer. Samples may be taken prior to and/or during and/or following antidepressant therapy. Samples can be taken at intervals over the remaining life, or a part thereof, of a patient.

Thus, in this way, in a non-invasive and easy manner, the progress of the disease can be monitored.

EXAMPLES

Example 1

Ten patients with DSM IV diagnosed major depression having a Hamilton score of 18 or more, one person with DSM IV diagnosed anxiety disorder having a Hamilton score of 18 or more and 1 person with DSM IV diagnosed bipolar depression having a Hamilton score of 18 or more were matched with respect to age, gender and ethnic origin with 12 healthy persons.

From all these persons blood and urine was collected through venapunction in 9 mL tubes. These were centrifuged for 10 minutes at 3000×g. Aliquots were divided over 25 tubes; these were held at 4° C. and stored at −80° C. until use. Urine samples were taken from morning midstream urine, which were directly stored at 4° C. The same day these samples were centrifuged for 10 minutes at 3000×g and aliquoted over 20 tubes. These were stored at −80° C. until further use.

These samples were tested with commercially available assays for the following biomarkers. The assays were obtained from the following vendors and the assays were performed according to the instructions of the vendor, unless otherwise indicated hereinafter.

R&D systems Europe Ltd. (Abingdon, United Kingdom) for Cortisol, LTB4, Thromboxane, Endothelin-1, Substance P, PGE2, c-AMP, and c-GMP;

Ray Biotech Inc (Norcross, Ga., USA) for Activin, Lox-1, Leptin, EGF, Lipocalin, adiponectin, TNFalphareceptor 2 and HVEM, Biovendor GmbH (Heidelberg, Germany) for PEDF, VILIP-1;

Sanbio BV (Hycult biotech, Uden, The Netherlands) for Calprotectin;

Northwest Life Science Specialties, LLC (Vancouver, Wash., USA) for Isoprostane-2, and nitrotyrosine;

Immundiagnostik GmbH (Bensheim, Germany) for Zonulin;

LDN GmbH (Nordhorn, Germany) for GABA;

IBL-Hamburg GmbH (Hamburg, Germany) for Neopterin;

Cellmid Limited (Perth, Australia) for Midkine;

Cusabio (Wuhan, China) for Galectin-8;

Immunology Consultants Lab., Inc. (Portland, Oreg., USA) for myeloperoxidase; Diasource (Leuven, Belgium) for Pregnenolone, vitamin D;

Peninsula Laboratories, LLC (San Carlos, Calif., USA) for NPY and Arg-vasopressin, Monobind Inc (Lake Forest, Calif., USA) for digoxin, Promega Benelux BV (Leiden, The Netherlands) for BDNF; and NovaTeinBio (Cambridge, Mass., USA) for Beclin.

The testing was performed with ELISA technology. All procedures were performed according to the manufacturer's instructions making use of an ELISA plate washer PW40 (Sanofi Pasteur). Read-outs of the Microtiterplate were digitally saved and further used for the data reduction. All data analysis has been done by making use of standard curves of OD values obtained by the Microtiterplate reader (Multiscan EF type 35, ThermoScientific) against concentrations as provided by the individual manufacturers of the kits. Individual measured patient sample values were obtained by interpolation of the sample OD value and the OD values of the standard curve obtained in each run.

The results of the individual markers in the individual samples are presented in Table 2 for the serum samples and in Table 3 for the urine samples. The urine samples were corrected for creatinin.

The data from the patients and control persons were collected and for every parameter two values were determined, if possible. To obtain the two values for every parameter a Receiver Operating Characteristic (ROC) was determined using the statistical program Medcalc (version 11.4.0.0, http://www.medcalc.org). A first value was determined which would discriminate between the two groups being the criterion for the Cut-off for having the disease, set at >95% of the calculated Positive Predictive Value (+PV). Any sample value measured exceeding this first discriminative value (Cut-off-Dis, for diseased) is considered discriminative for the diseased state. The second value was the reciprocal situation: being the criterion for the Cut-off for not having the disease, set at >95% of the calculated Negative Predictive Value (−PV). Any sample value measured exceeding this second discriminative value (Cut-off-Excl., excluding the diseased state) is considered discriminative for the healthy state. Any value found in between the Cut-off-Dis and Cut-off-Excl is considered non-discriminative. The parameters where the measurements enabled the determination of one or both of these cut-off values were regarded as being sufficient discriminatory to be used as a marker for the present invention.

On basis of results of the Cut-off-Dis and Cut-off-Excl. for each parameter the results were further analyzed by assigning the samples being Positive, Negative and indeterminate. A positive sample was assigned the value +1, a Negative sample the value '−1', and the indeterminate the value '0'. Next, a set of markers was constructed. Per sample, in each set parameters, the sum of all Pos, Neg and indeterminate results (expressed in +1, −1, 0) was determined, which resultant values were then tested for sensitivity and specificity by ROC analysis: optimal cut-off results obtained with each set of markers were used to assign patients being diseased or to exclude controls from being diseased from the resultant +PV and −PV for each set of markers.

Three sets of data were analysed separately to make choices for combinations of biomarkers in each set. The sets were based on the body-fluid in which the biomarkers are detected: serum/plasma, urine, or the combination serum/plasma and urine. In all three sets, based on increasing contribution, a reduction in the numbers of biomarkers can be reached, starting with the 4th order (i.e. all markers) down to the 3rd, the 2nd and ultimately to the 1st order. Significance of a contribution of biomarkers in the respective order is based on the position of the Area under the Curve (AUC) of the measured combination in the phenotype randomisation histogram of the AUC as defined for ROC analysis. Significance is any position within the right 0% to 5% region. The significances shown in Table 4 are given upon phenotype randomisation against the total number of biomarkers included in the $4^{th}$-$1^{st}$ order biomarkers. The AUC varies from 0.500 to 1.000. The higher the value of the AUC, the better its sensitivity and specificity. The AUC is therefore chosen to evaluate the performance of each combination of biomarkers and to make choices for optimization purposes.

Within each 'order' three or four analyses are done, based on different inclusion criteria at 90% and 95% respectively. The more stringent the inclusion criterion, the less the number of biomarkers that are included fulfill the inclusion criteria ('participating biomarkers'). Upon increasing the stringency starting in the 4th order, the amount of participating biomarkers decreases, allowing to make an optimisation choice. Those biomarkers under a certain condition that are found not to participate under higher stringencies are excluded in the next lower order, stepwise.

Description of the Choices.

1. Urine Plus Serum/Plasma.

Testing significance at stringency to include 7.5% for the 90% and 95% conditions, shows a phenotype randomisation significance of p=0.04. Under this condition, all 40 biomarkers are included making each biomarker a potential candidate irrespective the body fluid in which it is tested (randomisation run characteristics: $AUC_{-real}$=0.855, $AUC_{-random}$=0.801+/−0.032, number of runs=3025, fraction left of 0.855=95.7%, active biomarkers 40/40, Software Randomisation check version 1.05, see table).

$4^{th}$ order: all 40 tested biomarkers appeared to be included.

$3^{rd}$ order: excluded 19 biomarkers at inclusion condition 20%/12.5%, remaining 21 biomarkers.

$2^{nd}$ order: excluded 3 biomarkers at inclusion condition 25%/12.5%, remaining 16 biomarkers.

$1^{st}$ order: excluded 5 biomarkers at inclusion condition 25%/15%, remaining 11 biomarkers.

Condition of maximum performance, $AUC_{max}$=0.879, reached with 21 biomarkers: 10 serum biomarkers plus 11 urine biomarkers. Condition of optimal performance, $AUC_{min}$=0.858, reached with 11 biomarkers: combination of 5 biomarkers in serum and 6 biomarkers in urine.

2. Urine.

A stringency to include 10% at 90% and 95%, obtains a significance of p=0.046. Under this condition, all 19 biomarkers are included making each urine biomarker tested a potential candidate. Randomisation run characteristics: $AUC_{-real}$=0.781, $AUC_{-random}$=0.721+/−0.037, number of runs=3538, fraction left of 0.721=95.4%, active biomarkers 19/19, Software Randomisation check version 1.05, data not shown in table.

$4^{th}$ order: all 19 biomarkers appeared to be included.

$3^{rd}$ order excluded 4 biomarkers at inclusion condition 14%/10%: remaining 15 biomarkers.

$2^{nd}$ order excluded 4 biomarkers at inclusion condition 20%/12.5%: remaining 11 biomarkers.

$1^{st}$ order excluded 4 biomarkers at inclusion condition 25%/15%: remaining 7 biomarkers.

Condition of maximum performance, $AUC_{max}$=0.825, reached with 11 biomarkers. Condition of optimum performance, $AUC_{opt}$=0.823, reached with 11 biomarkers.

3. Serum/Plasma.

A stringency to include 7.5% at 90% and 95% shows a significance of p=0.030. Under this condition, all 21 biomarkers are included making each serum/plasma biomarker tested a potential candidate. Randomisation run characteristics: $AUC_{-real}$=0.793, $AUC_{-random}$=0.727+/−0.036, number of runs=3154, fraction left of 0.721=97.0%, active biomarkers 21/21, Software Randomisation check version 1.05, data not shown in table.

$4^{th}$ order: 21 biomarkers included.

$3^{rd}$ order excluded 4 biomarkers at inclusion condition 15%/7.5%, remaining 17 biomarkers.

$2^{nd}$ order excluded 7 biomarkers at inclusion condition 20%/12.5%, remaining 10 biomarkers.

$1^{st}$ order excluded 4 biomarkers at inclusion condition 25%/14%, remaining 6 biomarkers.

Condition of maximum performance, $AUC_{max}$=0.793, reached with 21 biomarkers. Condition of optimum performance, $AUC_{opt}$=0.775, reached with 10 biomarkers.

TABLE 2

| inclusion number | Clin. Score hamilton D17 | Serum Nr. 1 4106-Thromboxane | Serum Nr. 2 4701-cAMP | Serum Nr. 3 4007-Endothelin | Serum Nr. 4 4902-Aldosteron | Serum Nr. 5 4901-Zonulin | Serum Nr. 6 0401-Lox-1 | Serum Nr. 7 0302-Vitamin D |
|---|---|---|---|---|---|---|---|---|
| 2 | 2 | 11.9 | 16 | 0.60 | 52 | 2.85 | 82 | 26.2 |
| 25 | 2 | 17.0 | 8 | 1.08 | 53 | 1.72 | 98 | 19.0 |
| 28 | 2 | 20.0 | 13 | 0.86 | 52 | 2.67 | 77 | 17.8 |
| 39 | 2 | 2.5 | 7 | 1.40 | 37 | 3.14 | 26 | 17.4 |
| 42 | 2 | 11.5 | 15 | 0.86 | 47 | 2.58 | 22 | 7.7 |
| 85 | 2 | 11.7 | 8 | 1.01 | 79 | 3.75 | 81 | 8.9 |
| 112 | 2 | 20.0 | 15 | 1.05 | 61 | 3.68 | 76 | 24.5 |
| 151 | 2 | 1.51 | 16 | 0.46 | 46 | 2.93 | 1 | 37.1 |
| 232 | 2 | 11.9 | 12 | 0.71 | 73 | 3.51 | 110 | 31.5 |
| 246 | 2 | 17.1 | 12 | 1.03 | 54 | 2.79 | 57 | 22.6 |
| 240 | 3 | 20.0 | 7 | 1.08 | 49 | 3.25 | 38 | 18.7 |
| 228 | 6 | 10.5 | 12 | 0.68 | 46 | 2.24 | 81 | 28.6 |
| 34 | 20 | 0.7 | 19 | 1.51 | 56 | 3.62 | 90 | 28.3 |
| 36 | 21 | 7.2 | 28 | 0.63 | 87 | 3.82 | 194 | 14.5 |
| 41 | 22 | 2.5 | 15 | 0.38 | 140 | 3.19 | 81 | 42.1 |
| 209 | 25 | 5.0 | 19 | 0.53 | 49 | 3.89 | 52 | 44.7 |
| 47 | 27 | 2.5 | 13 | 1.65 | 68 | 4.57 | 106 | 6.6 |
| 122 | 27 | 20.0 | 81 | 1.85 | 831 | 2.64 | 41 | 10.1 |
| 56 | 28 | 1.49 | 11 | 1.25 | 54 | 3.40 | 20 | 32.6 |
| 245 | 28 | 0.92 | 19 | 0.86 | 101 | 3.39 | 148 | 27.7 |
| 242 | 30 | 6.8 | 15 | 1.01 | 67 | 3.79 | 128 | 28.5 |
| 176 | 35 | 2.5 | 8 | 1.81 | 33 | 3.57 | 46 | 43.7 |

TABLE 2-continued

| 69 | 36 | 1.4 | 10 | 0.86 | 87 | 3.78 | 27 | 15.1 |
| 148 | 37 | 5.7 | 10 | 1.10 | 23 | 2.29 | 65 | 53.2 |

| inclusion number | Serum Nr. 8 xxxx-(Activin (Inhibin) | Serum Nr. 9 3810-TNF R2 | Serum Nr. 10 4704-PEDF | Serum Nr. 11 3906-Substance P | Serum Nr. 12 0301-cGMP | Serum Nr. 13 5204-Pregnenolon | Serum Nr. 14 3808-EGF | Serum Nr. 15 4402-GABA |
|---|---|---|---|---|---|---|---|---|
| 2 | Has to be | 34 | 289 | 53 | 1.1 | 7.3 | 11.6 | 316 |
| 25 | measured | 21.9 | 452 | 55 | 0.0 | 5.9 | 15.1 | 5 |
| 28 | (as per | 47 | 323 | 126 | 6.0 | 3.9 | x | 41 |
| 39 | 28 Jan. 2013) | 47 | 329 | 64 | 3.4 | 11.3 | 14.1 | 14 |
| 42 | | 40 | 232 | 68 | 11.3 | 0.6 | 6.3 | 25 |
| 85 | | 28 | 252 | 14 | 11.6 | 3.6 | 17.7 | 288 |
| 112 | | 30 | 285 | 21 | 4.6 | 14.5 | 31.0 | 38 |
| 151 | | 39 | 279 | 120 | 19.4 | 6.2 | 1.9 | 11 |
| 232 | | 52 | 282 | 18 | 7.6 | x | 14.1 | 7 |
| 246 | | 60.8 | 232 | 43 | 9.0 | 7.9 | 9.9 | 6 |
| 240 | | 32 | 310 | 61 | 2.7 | 6.3 | 31.0 | 409 |
| 228 | | 49 | 195 | 104 | 0.8 | 24.7 | 21.0 | 14 |
| 34 | | 75 | 1786 | 100 | 9.3 | 3.3 | 5.5 | 9 |
| 36 | | 32 | 1651 | 26 | 9.3 | x | 12.2 | 275 |
| 41 | | 81 | 226 | 51 | 5.9 | x | 8.8 | 50 |
| 209 | | 45 | 174 | 10 | 6.5 | 1.0 | 8.2 | 252 |
| 47 | | 58 | 209 | 9 | 10.2 | 16.1 | 29.9 | 30 |
| 122 | | 43 | 1686 | 34 | 9.1 | 6.1 | 11.2 | 33 |
| 56 | | 77 | 211 | 61 | 0.0 | 16.8 | 5.6 | 268 |
| 245 | | 36 | 239 | 37 | 6.9 | 3.1 | 13.3 | 46 |
| 242 | | 38 | 202 | 7 | 3.0 | 21.5 | 7.8 | 251 |
| 176 | | 35 | 261 | 31 | 9.3 | 14.7 | 5.4 | 22 |
| 69 | | 33 | 268 | 12 | 0.6 | 19.5 | x | 16 |
| 148 | | 33 | 293 | 67 | 2.7 | 20.7 | 6.5 | 45 |

| inclusion number | Serum Nr. 16 4702-Calreticulin | Serum Nr. 17 4009-Neuropeptide | Serum Nr. 18 4207-VILIP | Serum Nr. 19 4703-Myeloperoxidase | Serum Nr. 20 0304-AVP (Vasopressin) | Serum Nr. 21 3801-Leptin (pg/mL) | Serum Nr. 22 4109-Galectin-8 |
|---|---|---|---|---|---|---|---|
| 2 | 0 | 0.47 | 4 | 8 | 162 | 217 | 0.0 |
| 25 | 0 | 0.37 | 4 | 8 | 61 | 177 | 38.9 |
| 28 | 20 | 0.52 | 54 | 8 | 114 | 19 | 61.3 |
| 39 | 0 | 0.48 | 9 | 11 | 48 | 12 | 14.8 |
| 42 | 0 | 0.42 | 4424 | 5 | 162 | 158 | 33.5 |
| 85 | 2.4 | 0.59 | 0 | 12 | 74 | 85 | 55.9 |
| 112 | 0 | 0.38 | 0 | 12 | 46 | 66 | 52.5 |
| 151 | 0 | 0.48 | 0 | 4 | 77 | 11 | 3.6 |
| 232 | 0 | 0.44 | 0 | 10 | 53 | 15 | 39.5 |
| 246 | 0 | 0.54 | 11 | 14 | 40 | 15 | 42.3 |
| 240 | 0 | 0.39 | 0 | 8 | 51 | 16 | 9.3 |
| 228 | 1.8 | 0.43 | 11 | 6.9 | 62 | 22 | 3.8 |
| 34 | 0 | 0.58 | 45 | 11 | 11 | 74 | 33.8 |
| 36 | 0 | 0.38 | 3 | 12 | 65 | 10 | 60.8 |
| 41 | 1.6 | 7.21 | 13591 | 8.8 | 134 | 83 | 0.0 |
| 209 | 0 | 0.49 | 4 | 4 | 157 | 13 | 18.1 |
| 47 | 0 | 0.54 | 4 | 12 | 157 | 21 | 11.5 |
| 122 | 0 | 0.35 | 0 | 4 | 51 | 399 | 54.2 |
| 56 | 0 | 0.45 | 4 | 4 | 21 | 19 | 32.2 |
| 245 | 0 | 0.31 | 3 | 7 | 83 | 171 | 8.4 |
| 242 | 0 | 0.63 | 9 | 9 | 23 | 399 | 1.5 |
| 176 | 0.0 | 0.39 | 13 | 8.0 | 77 | 64 | 0.0 |
| 69 | 1.0 | 0.45 | 3 | 3.6 | 0 | 189 | 1.6 |
| 148 | 0 | 0.65 | 2127 | 8 | 61 | 4 | 9.8 |

| inclusion number | Serum Nr. 23 4206-Calprotectin | Serum Nr. 24 4303-bFGF | Serum Nr. 25 4601-Nitrotyrosine | Serum Nr. 26 3802-Lipocalin-2 | Serum Nr. 27 3803-Adiponectin | Serum Nr. 28 5201-LTB4 | Serum Nr. 29 3806-HVEM | Serum Nr. 30 3905-Prostaglandin |
|---|---|---|---|---|---|---|---|---|
| 2 | 7.8 | 1 | 7 | 223 | 4231 | 129 | 148 | 159 |
| 25 | 5.6 | 1 | 0 | 106 | 3540 | 196 | 215 | 398 |
| 28 | 6.4 | 2 | 19 | 120 | 7078 | 119 | x | 569 |
| 39 | 2.5 | 2 | 0 | 85 | 48928 | 57 | 320 | 176 |
| 42 | 8.1 | 1 | 0 | 68 | 15801 | 64 | 150 | 338 |
| 85 | 13.6 | 233 | 110 | 124 | 6109 | 278 | 346 | 173 |
| 112 | 5.7 | 166 | 0 | 168 | 2219 | 118 | 292 | 290 |
| 151 | 7.0 | 1 | 7 | 68 | 13889 | 53 | 76 | 109 |
| 232 | 13.4 | 1 | 0 | 84 | 2444 | 135 | 380 | 243 |
| 246 | 7.6 | 4 | 36 | 106 | 13889 | 23 | 266 | 459 |
| 240 | 5.6 | 1 | 0 | 96 | 48928 | 155 | 368 | 305 |
| 228 | 6.1 | 6 | 0 | 74 | 5809 | 92 | 272 | 220 |
| 34 | 18.6 | 98 | 0 | 166 | 2993 | 102 | 210 | 7 |

TABLE 2-continued

| 36 | 10.6 | 1 | 24 | 106 | 2514 | 118 | 274 | 29 |
|---|---|---|---|---|---|---|---|---|
| 41 | 9.3 | 9 | 6 | 124 | 14172 | 107 | 130 | 249 |
| 209 | 7.1 | 1 | 0 | 118 | 13853 | 75 | 318 | 340 |
| 47 | 7.8 | 1 | 6 | 75 | 9366 | 150 | 443 | 208 |
| 122 | 4.7 | 9 | 0 | 65 | 7019 | 361 | 171 | 959 |
| 56 | 9.2 | 2 | 0 | 102 | 14293 | 40 | 103 | 277 |
| 245 | 7.4 | 122 | 0 | 70 | 1819 | 104 | 457 | 229 |
| 242 | 12.9 | 397 | 16 | 75 | 5664 | 60 | 240 | 199 |
| 176 | 7.0 | 22 | 8 | 60 | 16831 | 35 | 184 | 201 |
| 69 | 5.7 | 1 | 0 | 151 | 5073 | 61 | 206 | 156 |
| 148 | 5.2 | 5 | 0 | 85 | 48928 | 50 | 371 | 337 |

| inclusion number | Serum Nr. 31 4003-Midkine | Serum Nr. 32 4302-BDNF | Serum Nr. 33 4005-Isoprostane | Serum Nr. 34 3809-MMP-1 | Serum Nr. 35 4404-Digoxin | Serum Nr. 36 5202-PLA2-PAF | Serum Nr. 37 5203-sVEGF | Serum Nr. 38 4602-BCl-2 |
|---|---|---|---|---|---|---|---|---|
| 2 | 126 | 534 | 0.00 | 3048 | 313 | 6.0 | 20.3 | 0.0 |
| 25 | 103 | 338 | 0.00 | 820 | 252 | 3.8 | 6.8 | 0.0 |
| 28 | 2718 | 555 | 0.00 | 5310 | 54 | 10.1 | 19.0 | 15.3 |
| 39 | 103 | 783 | 0.05 | 6614 | 25 | 5.3 | 57.2 | 0.0 |
| 42 | 154 | 655 | 0.00 | 4219 | 75 | 4.8 | 7.1 | 0.0 |
| 85 | 165 | 929 | 0.08 | 8532 | 282 | 8.6 | 16.4 | 1.1 |
| 112 | 110 | 835 | 0.05 | 4636 | 21 | 9.9 | 8.9 | 0.0 |
| 151 | 125 | 290 | 0.20 | 2081 | 53 | 5.5 | 4.6 | 0.0 |
| 232 | 161 | 525 | 0.00 | 2699 | 128 | 4.9 | 15.0 | 0.0 |
| 246 | 265 | 585 | 1.21 | 4440 | 84 | 4.2 | 6.9 | 0.6 |
| 240 | 133 | 737 | 0.00 | 4095 | 54 | 5.3 | 19.0 | 0.0 |
| 228 | 150 | 488 | 0.00 | 2981 | 66 | 6.8 | 9.3 | 0.0 |
| 34 | 69 | 642 | 0.00 | 3428 | 134 | 5.7 | 20.3 | 0.0 |
| 36 | 111 | 672 | 0.46 | 4342 | 114 | 8.9 | 18.2 | 0.0 |
| 41 | 245 | 443 | 0.00 | 1714 | 31 | 1.7 | 6.1 | 20.2 |
| 209 | 131 | 494 | 0.00 | 2989 | 49 | 6.7 | 21.2 | 0.0 |
| 47 | 168 | 756 | 3.23 | 3275 | 23 | 7.1 | 6.5 | 0.0 |
| 122 | 77 | 355 | 0.00 | 1145 | 613 | 13.6 | 17.1 | 0.0 |
| 56 | 280 | 577 | 0.00 | 2311 | 53 | 6.6 | 24.1 | 0.0 |
| 245 | 253 | 773 | 0.00 | 7970 | 20 | 5.5 | 9.5 | 1.2 |
| 242 | 74 | 493 | 0.00 | 2993 | 296 | 4.4 | 9.3 | 0.0 |
| 176 | 228 | 715 | 0.63 | 3927 | 74 | 3.6 | 14.7 | 0.0 |
| 69 | 89 | 326 | 0.00 | 5180 | 264 | 7.3 | 12.6 | 0.0 |
| 148 | 106 | 630 | 0.00 | 4214 | 67 | 5.4 | 37.1 | 0.0 |

TABLE 3

| inclusion number | Clin. Score hamilton D17 | Urine Nr. 1 4106-Thromboxan | Urine Nr. 2 5204-Pregnenolon | Urine Nr. 3 3806-HVEM | Urine Nr. 4 xxxx-Vit. D | Urine Nr. 5 4903-cGMP | Urine Nr. 6 3906-Substance P | Urine Nr. 7 xxxx-Activin (inhibin) |
|---|---|---|---|---|---|---|---|---|
| 2 | 2 | 0.132 | 0.24 | 24 | Has to be measured (as per 28 Jan. 2013) | 0.18 | 4.0 | Has to be measured (as per 28 Jan. 2013) |
| 25 | 2 | 0.15 | 0.34 | 29 | | 0.42 | 8.4 | |
| 28 | 2 | 0.115 | 0.7 | 23 | | 0.40 | 4.4 | |
| 39 | 2 | 0.14 | 0.6 | 38 | | 0.15 | 5.5 | |
| 42 | 2 | 0.26 | 3.7 | 40 | | 0.36 | 13.2 | |
| 85 | 2 | 0.17 | 0.4 | 30 | | 0.51 | 3.0 | |
| 112 | 2 | 0.19 | 0.4 | 37 | | 0.57 | 2.7 | |
| 151 | 2 | 0.35 | 0.4 | 24 | | 0.89 | 1.7 | |
| 232 | 2 | 0.08 | 1.0 | 24 | | 0.45 | 0.7 | |
| 246 | 2 | 0.14 | 0.20 | 27 | | 0.43 | 1.1 | |
| 240 | 3 | 0.16 | 1.0 | 37 | | 0.64 | 18.3 | |
| 228 | 6 | 0.26 | 0.27 | 24 | | 0.21 | 0.4 | |
| 34 | 20 | 0.49 | 1.0 | 28 | | 0.57 | 11.3 | |
| 36 | 21 | 0.21 | 0.4 | 37 | | 0.39 | 23.5 | |
| 41 | 22 | 0.28 | 0.8 | 46 | | 0.89 | 15.0 | |
| 209 | 25 | 0.23 | 1.6 | 21 | | 0.41 | 5.4 | |
| 47 | 27 | 0.46 | 0.6 | 61 | | 0.74 | 11.2 | |
| 122 | 27 | 0.30 | 1.2 | 29 | | 0.40 | 1.9 | |
| 56 | 28 | 0.14 | 1.9 | 40 | | 0.36 | 6.3 | |
| 245 | 28 | 0.25 | 0.9 | 45 | | 0.54 | 61.8 | |
| 242 | 30 | 0.27 | 4.7 | 53 | | 0.66 | 11.5 | |
| 176 | 35 | 0.24 | 1.0 | 35 | | 0.80 | 5.7 | |
| 69 | 36 | ND | 1.1 | ND | | ND | ND | |
| 148 | 37 | 0.25 | 1.1 | 40 | | 0.30 | 1.4 | |

TABLE 3-continued

| inclusion number | Urine Nr. 8 4501-cAMP | Urine Nr. 9 4502-Cortisol | Urine Nr. 10 4902-Aldosteron | Urine Nr. 11 3801-Leptin | Urine Nr. 12 4006-Isoprostane urine | Urine Nr. 13 0401-LOX-1 | Urine Nr. 14 4009-Neuropeptide Y | Urine Nr. 15 3803-Adiponectin |
|---|---|---|---|---|---|---|---|---|
| 2 | 4.3 | 0.31 | 4.2 | 0 | 0.04 | 81.6 | 4 | 362 |
| 25 | 7.9 | 0.25 | 4.9 | 0 | 0.02 | 98.5 | 4 | 454 |
| 28 | 4.0 | 0.30 | 3.5 | 19 | 0.03 | 76.9 | 4 | 317 |
| 39 | 5.7 | 0.41 | 4.4 | 1 | 0.05 | 26.0 | 3 | 1376 |
| 42 | 5.3 | 0.15 | 4.7 | 1 | 0.03 | 21.6 | 18 | 1091 |
| 85 | 7.8 | 0.58 | 6.9 | 5 | 0.04 | 81.1 | 15 | 704 |
| 112 | 4.9 | 0.20 | 3.6 | 3 | 0.05 | 75.8 | 8 | 6702 |
| 151 | 8.5 | 0.77 | 5.4 | 0 | 0.04 | 1.0 | 14 | 1811 |
| 232 | 7.9 | 0.26 | 5.1 | 1 | 0.05 | 109.5 | 2.01 | 2861 |
| 246 | 3.2 | 0.34 | 4.9 | 10 | 0.02 | 56.7 | 9 | 370 |
| 240 | 6.0 | 0.30 | 9.2 | 5 | 0.03 | 37.9 | 13 | 1735 |
| 228 | 5.5 | 0.46 | 4.3 | 1 | 0.05 | 80.8 | 6 | 625 |
| 34 | 10.2 | 0.26 | 4.1 | 11 | 0.07 | 90.4 | 23 | 341 |
| 36 | 6.2 | 0.15 | 7.2 | 7 | 0.04 | 194.2 | 3 | 454 |
| 41 | 8.4 | 0.12 | 11.8 | 6 | 0.07 | 81.1 | 45 | 1742 |
| 209 | 4.9 | 0.25 | 3.1 | 1 | 0.02 | 52.3 | 10 | 517 |
| 47 | 7.2 | 0.28 | 5.2 | 0 | 0.10 | 105.9 | 9 | 182 |
| 122 | 5.5 | 0.32 | 5.9 | 48 | 0.03 | 40.8 | 11 | 845 |
| 56 | 6.1 | 0.40 | 4.6 | 10 | 0.03 | 19.5 | 7 | 840 |
| 245 | 4.8 | 0.32 | 8.6 | 1 | 0.03 | 148.0 | 5 | 1100 |
| 242 | 9.3 | 0.11 | 9.6 | 2 | 0.04 | 128.0 | 11 | 1362 |
| 176 | 23.4 | 0.46 | 7.6 | 3 | 0.13 | 45.7 | 5 | 549 |
| 69 | ND | ND | ND | ND | ND | 27.0 | ND | ND |
| 148 | 7.9 | 0.34 | 4.1 | 40 | 0.03 | 65.3 | 13 | 721 |

| inclusion number | Urine Nr. 16 4601-Nitrotyrosine | Urine Nr. 17 5201-LTB4 | Urine Nr. 18 4402-GABA | Urine Nr. 19 4206-Calprotectin | Urine Nr. 20 3802-Lipocalin-2 | Urine Nr. 21 3905-PGE-2 | Urine Nr. 22 4003-Midkine | Urine Nr. 23 0304-Vasopressin (AVP) |
|---|---|---|---|---|---|---|---|---|
| 2 | 0.002 | 32 | 129 | 0.2 | 8 | 33 | 14.6 | 2.7 |
| 25 | 0.003 | 21 | 137 | 0.8 | 9 | 45 | 7.2 | 1.8 |
| 28 | 0.002 | 27 | 105 | 0.2 | 1.3 | 92 | 11.2 | 1.9 |
| 39 | 0.004 | 38 | 398 | 0.8 | 6 | 38 | 3.9 | 0.5 |
| 42 | 0.008 | 54 | 579 | 3.1 | 42 | 54 | 1.0 | 20.3 |
| 85 | 0.005 | 26 | 92 | 0.1 | 3 | 26 | 8.8 | 1.7 |
| 112 | 0.005 | 50 | 73 | 0.3 | 10 | 33 | 10.1 | 1.0 |
| 151 | 0.005 | 31 | 212 | 3.9 | 25 | 49 | 9.6 | 13.5 |
| 232 | 0.002 | 26 | 213 | 0.3 | 0.8 | 23 | 6.2 | 0.8 |
| 246 | 0.002 | 22 | 95 | 1.6 | 40 | 21 | 10.0 | 1.8 |
| 240 | 0.005 | 35 | 176 | 0.5 | 2.0 | 47 | 31.6 | 2.3 |
| 228 | 0.623 | 25 | 95 | 0.9 | 4 | 31 | 8.6 | 2.8 |
| 34 | 0.252 | 46 | 144 | 0.7 | 6 | 65 | 11.1 | 1.8 |
| 36 | 0.395 | 24 | 174 | 0.0 | 3 | 32 | 8.8 | 1.3 |
| 41 | 0.010 | 57 | 128 | 5.3 | 12 | 62 | 13.6 | 1.2 |
| 209 | 0.003 | 38 | 97 | 0.5 | 18 | 40 | 13.4 | 1.5 |
| 47 | 0.001 | 28 | 127 | 1.1 | 9 | 81 | 9.1 | 0.5 |
| 122 | 0.004 | 50 | 400 | 0.1 | 4 | 34 | 12.8 | 2.3 |
| 56 | 0.005 | 31 | 353 | 1.3 | 29 | 19 | 8.3 | 2.1 |
| 245 | 2.312 | 47 | 481 | 0.9 | 8 | 42 | 11.1 | 2.1 |
| 242 | 0.008 | 46 | 758 | 3.5 | 21 | 48 | 14.2 | 4.7 |
| 176 | 0.004 | 48 | 254 | 2.9 | 96 | 82 | 261.4 | 1.7 |
| 69 | ND | 43 | ND | ND | ND | ND | ND | 2.7 |
| 148 | 0.004 | 27 | 398 | 1.3 | 7 | 42 | 26.3 | 1.5 |

| inclusion number | Urine Nr. 24 3904-IGF1 | Urine Nr. 25 4010-cck | Urine Nr. 26 3810-TNF R2 | Urine Nr. 27 4303-Digoxin | Urine Nr. 28 4007-Endothelin | Urine Nr. 29 4403-Neopterin | Urine Nr. 30 4703-Myeloperoxidase | Urine Nr. 31 5203-sVSGF | Urine Nr. 32 3808-EGF |
|---|---|---|---|---|---|---|---|---|---|
| 2 | 0.6 | 13.4 | 5.1 | 0.08 | 0.00 | 1.3 | 0.1 | 0.2 | 29 |
| 25 | 0.5 | 43.8 | 1.7 | 0.26 | 0.02 | 1.8 | 0.3 | 0.2 | 4 |
| 28 | 0.2 | 15.4 | 3.4 | 0.05 | 0.02 | 1.6 | 0.1 | 0.2 | 0 |
| 39 | 0.8 | 132.4 | 2.5 | 0.10 | 0.00 | 1.3 | 0.2 | 0 | 9 |
| 42 | 0.8 | 29.1 | 2.8 | 0.04 | 0.00 | 1.6 | 2.6 | 69 | 11 |
| 85 | 1.1 | 20.8 | 12.4 | 0.04 | 0.00 | 1.4 | 0.4 | 3.4 | 1 |
| 112 | 0.2 | 50.8 | 5.1 | 0.03 | 0.00 | 1.9 | 0.5 | 6.0 | 1 |
| 151 | 1.3 | 9.6 | 3.9 | 0.21 | 0.11 | 1.9 | 1.2 | 22.5 | 0 |
| 232 | 0.2 | 30.2 | 4.5 | 0.09 | 0.00 | 2.8 | 0.1 | 0.1 | 6 |
| 246 | 0.2 | 4.2 | 2.0 | 0.01 | 0.07 | 3.2 | 0.6 | 0.3 | 3 |
| 240 | 0.9 | 12.1 | 6.1 | 0.03 | 0.00 | 0.9 | 0.4 | 0.8 | 1 |
| 228 | 0.2 | 15.6 | 4.8 | 0.06 | 0.05 | 1.5 | 0.6 | 0.3 | 11 |
| 34 | 0.4 | 1.6 | 3.9 | 0.03 | 0.01 | 1.9 | 0.2 | 0.3 | 0 |
| 36 | 0.3 | 50.8 | 11.3 | 0.09 | 0.00 | 2.6 | 0.1 | 0.1 | 0 |
| 41 | 0.5 | 22.2 | 7.6 | 0.03 | 0.02 | 4.3 | 0.7 | 0.5 | 16 |
| 209 | 0.3 | 12.9 | 1.2 | 0.04 | 0.02 | 1.7 | 0.2 | 0.4 | 5 |
| 47 | 0.5 | 0.9 | 7.8 | 0.03 | 0.01 | 1.5 | 0.1 | 0.2 | 1 |

TABLE 3-continued

| | | | | | | | | | |
|---|---|---|---|---|---|---|---|---|---|
| 122 | 0.4 | 19.7 | 3.6 | 0.05 | 0.00 | 1.8 | 0.8 | 34 | 7 |
| 56 | 1.6 | 63.6 | 3.0 | 0.03 | 0.00 | 2.2 | 0.4 | 21.8 | 72 |
| 245 | 0.5 | 923.5 | 7.9 | 0.10 | 0.00 | 2.3 | 0.4 | 0.7 | 10 |
| 242 | 1.5 | 82.4 | 5.9 | 0.26 | 0.00 | 1.7 | 0.8 | 5.5 | 12 |
| 176 | 0.7 | 18.9 | 16.9 | 0.09 | 0.22 | 0.8 | 9.7 | 0.6 | 0 |
| 69 | ND | ND | ND | ND | ND | ND | ND | 1.5 | ND |
| 148 | 1.2 | 24.4 | 3.4 | 0.06 | 0.00 | 1.8 | 0.5 | 0.2 | 17 |

All values are measured in morning-urine. The obtained concentrations are divided by the creatinine concentration in that sample. Also in the serum sample taken at the same time a potential kidney failure has been excluded by measuring the creatinine concentration.

TABLE 4

| | Condition 90%/95% | total # biomarkers | AUC | participating # Biomarkers | P | Significance at phenotype randomisation | Blood derived Biomarkers involved |
|---|---|---|---|---|---|---|---|
| Serum/Plasma | | | | | | | |
| 1st order biomarkers | 15/7.5 | 6 | 0.739 | 6 | 0.010 | significance at all conditions | TNF-R2, Cortisol, Thromboxane, Endothelin, Leptin, Vit. D |
| | 20/12.5 | 6 | 0.745 | 6 | 0.006 | | |
| | 25/12.5 | 6 | 0.744 | 6 | 0.005 | | |
| 2nd order biomarkers | 15/7.5 | 10 | 0.765 | 10 | 0.043 | significance at all conditions | 1st order plus: Calprotectin, cAMP, Zonulin, Substance P |
| | 20/12.5 | 10 | 0.750 | 10 | 0.049 | | |
| | 25/12.5 | 10 | 0.775 | 9 | 0.027 | | |
| 3rd order biomarkers | 15/7.5 | 17 | 0.776 | 17 | 0.180 | at 25%/12.5% | 2nd order plus: BDNF, Midkine, Nitrotyrosine, LTB4, NPY, Telomerase, Aldosteron |
| | 20/12.5 | 17 | 0.750 | 10 | 0.194 | | |
| | 25/12.5 | 17 | 0.775 | 9 | 0.043 | | |
| 4th order biomarkers | 7.5/7.5 | 21 | 0.793 | 21 | 0.030 | at 7.5%/7.5% only, see tekst | 3rd order plus: EGF, Lipocalin, HVEM, Isoprostane, |
| | 15/7.5 | 21 | 0.776 | 17 | 0.678 | | |
| | 20/12.5 | 21 | 0.750 | 10 | 0.300 | | |
| | 25/12.5 | 21 | 0.775 | 9 | 0.079 | | |
| Urine | | | | | | | |
| 1st order biomarkers | 15/7.5 | 7 | 0.778 | 7 | 0.0006 | all conditions highly significant | cGMP, Cortisol, Calprotectin, Thromboxane, Aldosteron, HVEM, Substance P |
| | 20/12.5 | 7 | 0.780 | 7 | <0.00001 | | |
| | 25/12.5 | 7 | 0.780 | 7 | <0.00001 | | |
| 2nd order biomarkers | 15/7.5 | 11 | 0.823 | 11 | <0.0001 | all conditions highly significant | 1st order plus: Leptin, LTB4, Isoprostane, Midkine |
| | 20/12.5 | 11 | 0.823 | 11 | <0.0001 | | |
| | 25/12.5 | 11 | 0.780 | 7 | 0.006 | | |
| 3rd order biomarkers | 15/7.5 | 15 | 0.815 | 15 | 0.007 | all conditions significant with highly significant optimum | 2nd order plus: cAMP, Endothelin, TNF-R2, NPY |
| | 20/12.5 | 15 | 0.825 | 11 | <0.0001 | | |
| | 25/12.5 | 15 | 0.780 | 7 | 0.02 | | |
| 4th order biomarkers | 15/7.5 | 19 | 0.816 | 18 | 0.03 | all conditions | 3rd order plus: Adiponectin, EGF, Lipocalin, Pregnenolon, |
| | 20/12.5 | 19 | 0.825 | 11 | 0.0028 | | |
| | 25/12.5 | 19 | 0.780 | 7 | 0.0369 | | |
| Serum + Urine | | | | | | | |
| 1st order biomarkers | 15/7.5 | 11 (5-S + 6-U) | 0.845 | 11 | <0.00001 | all conditions highly significant | TNF-R2-S, Cortisol-S, Thromboxane-S, Leptin-S, Endothelin-S, cGMP-U, Cortisol-U, Aldosteron-U, Thromboxane-U, HVEM-U, Substance P-U |
| | 20/12.5 | 11 (5-S + 6-U) | 0.856 | 11 | <0.00001 | | |
| | 25/12.5 | 11 (5-S + 6-U) | 0.858 | 11 | <0.00001 | | |

TABLE 4-continued

| Condition 90%/95% | total # biomarkers | AUC | participating # Biomarkers | P | Significance at phenotype randomisation | Blood derived Biomarkers involved |
|---|---|---|---|---|---|---|
| 2nd order biomarkers | | | | | | |
| 15/7.5 | 16 (9-S + 7-U) | 0.848 | 16 | 0.0009 | all conditions highly significant | 2nd order plus: Vit-D-S, cAmp-S, Zonulin-S, Substance-P-S, Calprotectin-U |
| 20/12.5 | 16 (9-S + 7-U) | 0.860 | 16 | 0.0009 | | |
| 25/12.5 | 16 (9-S + 7-U) | 0.860 | 16 | <0.0001 | | |
| 3rd order biomarkers | | | | | | |
| 15/7.5 | 21 (10-S + 11-U) | 0.874 | 21 | <0.0001 | all conditions highly significant | 2nd order plus: Calprotectin-S, Leptin-U, LTB4-U, Isoprostane-U, Midkine-U |
| 20/12.5 | 21 (10-S + 11-U) | 0.879 | 21 | <0.0001 | | |
| 25/12.5 | 21 (10-S + 11-U) | 0.860 | 16 | 0.002 | | |
| 4th order biomarkers | | | | | | |
| 7.5/7.5 | 40 (21-S + 19-U) | 0.855 | 40 | 0.045 | significance, except 15/7.5 | 3rd order plus: BDNF-S, Midkine-S, Nitrotyrosine-S, EGF-S, LTB4-S, Lipocalin-S, NPY-S, HVEM-S, Telomerase-S, Isoprostane-S, Aldosteron-S, cAMP-U, Endothelin-U, Adiponectin-U, EGF-U, TNF-R2-U, Lipocalin-U, Pregnenolon-U, NPY-U |
| 15/7.5 | 40 (21-S + 19-U) | 0.873 | 35 | 0.110 | | |
| 20/12.5 | 40 (21-S + 19-U) | 0.879 | 21 | 0.018 | | |
| 25/12.5 | 40 (21-S + 19-U) | 0.860 | 16 | 0.028 | | |

REFERENCES

Mineral Homeostatis Hypothesis
Groenestege W M, Thebault S van der Wijst J, van den Berg D, Janssen R, Tejpar S, van den Heuvel. L P, van Cutsem E, Hoenderop J G, Knoers N V, Bindels R J (2007)
cGMP
Function of cGMP-Dependent Protein Kinases as Revealed by Gene Deletion F. HOFMANN, R. FEIL, T. KLEPISCH, AND J. SCHLOSSMANN Institut fur Pharmakologie and Toxikologie, T U München, München, Germany. Physiol Rev 86: 1-23, 2006;
Affective Disorders and Nitric Oxide: A Role in Pathways to Relapse and Refractoriness? BRIAN H. HARVEY Human Psychopharmacology: Clinical and Experimental Volume 11, Issue 4, pages 309-319, July 1996
Cyclic nucleotides in mental disorder. Belmaker R H, Zohar J, Ebstein R P.
Adv Cyclic Nucleotide Res. 1980; 120:187-98.
Review Peptides in the cerebrospinal fluid of neuropsychiatric patients: an approach to central nervous system peptide function. Post R M, Gold P, Rubinow D R, Ballenger J C, Bunney W E Jr, Goodwin F K. Life Sci. 1982 Jul. 5; 31(1):1-15.
Plasma cortisol, catecholamine and cyclic AMP levels, response to dexamethasone suppression test and platelet MAO activity in manic-depressive patients. A longitudinal study. Maj M, Ariano M G, Arena F, Ketnali D. Neuropsychobiology. 1984; 11(3):168-73.
Aldosteron
Increased plasma aldosterone in patients with clinical depression.
Emanuele E, Geroldi D, Minoretti P, Coen E, Politi P. Molecular Medicine Laboratory, University of Pavia, Italy. Arch Med Res. 2005 September-October; 36(5):544-8.
Subchronic treatment with aldosterone induces depression-like behaviours and gene expression changes relevant to major depressive disorder. Hlavacova N, Wes D, Ondrejcakova M, Flynn M E, Poundstone P K, Babic S, Murck H, Jezova D. Laboratory of Pharmacological Neuroendocrinology, Institute of Experimental Endocrinology, Slovak Academy of Sciences, Vlarska, Bratislava, Slovakia.
Int J Neuropsychopharmacol. 2012 March; 15(2):247-65
The Renin-Angiotensin-Aldosterone system in patients with depression compared to controls—a sleep endocrine study Harald Murck,[2] Katja Held,[1] Marc Ziegenbein,[1] Heike Künzel,[1] Kathrin Koch,[1] and Axel Steiger
BMC Psychiatry. 2003; 3: 15
ACTH
Blunted aldosterone and ACTH release after human CRH administration in depressed patients. Am J Psychiatry 1987; 144:229-231.
Angiotensin II
Depression associated with valsartan, angiotensin II receptor antagonist; case report and review of the literature. Numan Konuk, Mustafa Aydin, Ömer Akay.
BCP. 2005; 15(4): 187-191
Angiotensin II-induced depression of Purkinje cell firing and possible modulatory action on GABA responses. Tongroach P, Sanguanrungsirikul S, Tantisira B, Kunluan P. Neurosci Res. 1984 October; 1(5):369-72.
AVP
van Londen L, Kerkhof G A, van den Berg F, Goekoop J G, Zwinderman K H, Frankhuijzen-Sierevogel A C, Wiegant V M, de Wied D. Plasma arginine vasopressin and motor activity in major depression. Biol Psychiatry. 1998 1; 43(3):196-204.
van Londen L, Goekoop J G, van Kempen G M, Frankhuijzen-Sierevogel A C, Wiegant V M, van der Velde E A, De Wied. Plasma levels of arginine vasopressin elevated in patients with major depression Neuropsychopharmacology. 1997; 17(4):284-92.

Bergquist J, Ekman R. Future aspects of psychoneuroimmunology—lymphocyte peptides reflecting psychiatric disorders studied by mass spectrometry. Arch Physiol Biochem. 2001; 109(4):369-71.

Ekman R, Gobom J, Persson R, Mecocci P, Nilsson C L. Arginine vasopressin in the cytoplasm and nuclear fraction of lymphocytes from healthy donors and patients with depression or schizophrenia. Peptides. 2001; 22(1): 67-72.

Penney M D, Levell M J, Hullin R P. Arginine vasopressin in manic-depressive psychosis. Psychol Med. 1987; 17(4):861-7.

SP

Skeletal and hormonal effects of magnesium deficiency.

Rude R K, Singer F R, Gruber H E. J Am Coll Nutr. 2009 April; 28(2):131-41.

Deuschle M, Sander P, Herpfer I, Fiebich B L, Heuser I, Lieb K. Substance P in serum and cerebrospinal fluid of depressed patients: no effect of antidepressant treatment. Psychiatry Res. 2005 Jul. 15; 136(1):1-6.

Lieb K, Walden J, Grunze H, Fiebich B L, Berger M, Normann C. Serum levels of substance P and response to antidepressant pharmacotherapy. Pharmacopsychiatry. 2004 September; 37(5):238-9.

Frisch P, Bilkei-Gorzó A, Rácz I, Zimmer A. Modulation of the CRH system by substance P/NKA in an animal model of depression. Behav Brain Res. 2010 Nov. 12; 213(1): 103-8.

Madaan V, Wilson D R. Neuropeptides: relevance in treatment of depression and anxiety disorders. Drug News Perspect. 2009 July-August; 22(6):319-24.

EGF

Impaired basolateral sorting of pro-EGF causes isolated recessive renal hypomagnesemia. *J Clin Invest* 117:2260-27.

Domenici E, Willé D R, Tozzi F, Prokopenko I, Miller S, McKeown A, Brittain C, Rujescu D, Giegling I, Turck C W, Holsboer F, Bullmore E T, Middleton L, Merlo-Pich E, Alexander R C, Muglia P. Plasma protein biomarkers for depression and schizophrenia by multi analyte profiling of case-control collections. PLoS One. 2010 Feb. 11; 5(2): e9166.

Koller M M, Cowman R A, Humphreys-Beher M G, Scarpace P J. An analysis of submandibular salivary gland function with desipramine and age in female NIA Fischer 344 rats. Mech Ageing Dev. 2000 Nov. 15; 119(3):131-47.

Skeletal and Hormonal Effects of Magnesium Deficiency.

Rude R K, Singer F R, Gruber H E.

J Am Coll Nutr. 2009 April; 28(2):131-41

REA/RACK-1

Regulation of the epithelial Mg2+ channel TRPM6 by estrogen and the associated repressor protein of estrogen receptor activity (REA).

Cao G, van der Wijst J, van der Kemp A, van Zeeland F, Bindels R J, Hoenderop J G. *J Biol Chem.* 2009 May 29; 284(22):14788-95.

Neurogenesis and Neuroplasticity

BDNF

Barde Y A, Edgar D, Thoenen H. Purification of a new neurotrophic factor from mammalian brain. EMBO J. 1982; 1:549-553.

Rosenfeld R D, Zeni L, Haniu M, Talvenheimo J, Radka S F, Bennett L, Miller J A, Welcher A A. Purification and identification of brain-derived neurotrophic factor from human serum. Protein Expr Purif. 1995 August; 6(4):465-71.

Lindsay R. M., Wiegrand S. J, Altar C. A. and Di Stefano S. Neurotrophic factors: from molecule to man. Trends in Neuroscience 17 (1994), pp. 182-189.

Lewin G. R. and Barde Y. A., Physiology of neurotrophins. Annual Review of Neuroscience 19 (1996), pp. 289-317.

Yamamoto and M. E. Gurney, Human platelets contain brain-derived neurotrophic factor. Journal of Neuroscience 10 (1990), pp. 3469-3478.

Mann J. J., P. A. McBride, G. M. Anderson and T. A. Mieczkowski, Platelet and whole blood serotonin content in depressed inpatients: correlations with acute and lifetime psychopathology. Biological Psychiatry 32 (1992), pp. 243-257

Radka S. F., P. A. Holst, M. Fristche and C. A. Altar, Presence of brain-derived neurotrophic factor in brain and human and rat but not mouse serum detected by a sensitive and specific immunoassay. Brain Research 709 (1996), pp. 122-130.

Pan W, W. A. Banks, M. B. Fasold, J. Blunth and A. J. Kasten, Transport of brain-derived neurotrophic factor across the blood-brain barrier. Neuropharmacology 37 (1998), pp. 1553-1561.

Karege F, Schwald M, Cisse M. Postnatal developmental profile of brain-derived neurotrophic factor in rat brain and platelets. Neurosci Lett. 2002 Aug. 16; 328(3):261-4.

Russo-Neustadt A., T. Ha, R. Ramirez and J. P. Kesslak, Physical activity-antidepressant combination: impact on brain derived neurotrophic factor and behavior in an animal model, Behav Brain Res 120 (2001), pp. 87-95.

Smith M. A, S. Makino, R. Kwetnansky and R. M. Post, Stress and glucocorticoids affects the expression of brain derived neurotrophic factor and neurotrophin-3 mRNAs in the hippocampus, J Neurosci 15 (1995), pp. 1768-1777.

Karege F., G. Perret, M. S. Bondolfi, G. Bertschy and J. M. Aubry, Decreased serum brain-derived neurotrophic factor levels in major depressed patients, Psychiatry Res 109 (2002), pp. 143-148. (a)

Karege F., M. Schwald and M. Cisse, Post natal profile of brain-derived neurotrophic factor in rat brain and platelets, Neurosci Lett 328 (2002), pp. 261-264. (b).

Shimuzu E., K. Hashimoto, K. Koike, N. Komatsu, C. Kumakiri and M. Nakazato et al., Alterations of serum levels of brain derived neurotrophic factor (BDNF) in depressed patients with or without antidepressants, Biol Psychiatry 54 (2003), pp. 70-75.

Gonul A. S., F. Akdeniz, F. Taneli, O. Donat, C. Eker and S. Vahip, Effect of treatment on serum brain-derived neurotrophic factor levels in depressed patients, Eur Arch Psychiatry Clin Neurosci 255 (2005), pp. 267-268.

Aydemir O., A. Deveci and F. Taneli, The effect of chronic antidepressant treatment on serum brain-derived neurotrophic factor levels in depressed patients: a preliminary study, Prog Neuropsychopharmacol Biol Psychiatry 29 (2005) (2), pp. 261-265.

Chen B, D. Dowlatshahi, G. M. MacQueen, J. F. Wang and L. T. Young, Increased hippocampal BDNF immunoreactivity in subjects treated with anti-depressant medication, Biol Psychiatry 50 (2001), pp. 260-265.

Aydemir C, Yalcin E S, Aksaray S, Kisa C, Yildirim S G, Uzbay T, Goka E. Brain-derived neurotrophic factor (BDNF) changes in the serum of depressed women.

Prog Neuropsychopharmacol Biol Psychiatry. 2006, 30; 30(7):1256-60.

Matrisciano F, Bonaccorso S, Ricciardi A, Scaccianoce S, Panaccione I, Wang L, Ruberto A, Tatarelli R, Nicoletti F, Girardi P, Shelton R C. Changes in BDNF serum levels in patients with major depression disorder (MDD) after 6 months treatment with sertraline, escitalopram, or venlafaxine. J Psychiatr Res. 2009, 43(3):247-54.

Lee H Y, Kim Y K. Plasma brain-derived neurotrophic factor as a peripheral marker for the action mechanism of antidepressants. Neuropsychobiology. 2008; 57(4):194-9.

Okamoto T, Yoshimura R, Ikenouchi-Sugita A, Hori H, Umene-Nakano W, Inoue Y, Ueda N, Nakamura J. Efficacy of electroconvulsive therapy is associated with changing blood levels of homovanillic acid and brain-derived neurotrophic factor (BDNF) in refractory depressed patients: a pilot study. Prog Neuropsychopharmacol Biol Psychiatry. 2008 1; 32(5):1185-90.

Dwivedi Y. Brain-derived neurotrophic factor: role in depression and suicide. Neuropsychiatr Dis Treat. 2009; 5:433-49.

Kim Y K, Lee H P, Won S D, Park E Y, Lee H Y, Lee B H, Lee S W, Yoon D, Han C, Kim D J, Choi S H. Low plasma BDNF is associated with suicidal behavior in major depression. Prog Neuropsychopharmacol Biol Psychiatry. 2007 Jan. 30; 31(1):78-85.

Castrén E, Rantamäki T. Neurotrophins in depression and antidepressant effects. Novartis Found Symp. 2008; 289: 43-52; discussion 53-9, 87-93.

HVEM

Murphy T L, Murphy K M. Slow down and survive: Enigmatic immunoregulation by BTLA and HVEM. Ann. Rev. Immunol. 2010; 28: 389-411.

De Trez C, Ware C F. The TNF receptor and Ig superfamily members form an integrated signalling circuit controlling dendritic cell homeostasis. Cytokine Growth Fact Rev. 2008; 19(3-4).

Uguz F, Akman C, Kucuksarca S, Tufekci O. Anti-tumor necrosis factor alpha therapy is associated with less frequent mood and anxiety disorders in patients with rheumatoid arthritis. Psych. Clin. Neurosci. 2009; 63(1): 50-5.

PEDF

Pigment epithelium-derived factor is a niche signal for neural stem cell renewal. Carmen Ramírez-Castillejo, Francisco Sánchez-Sánchez, Celia Andreu-Agulló, Sacri R Ferrón, J Daniel Aroca-Aguilar, Pilar Sánchez, Helena Mira, Julio Escribano & Isabel Fariñas. *Biol Psychiatry.* 2012 Oct. 1; 72(7):562-71. doi: 10.1016/j.biopsych.2012.04.024. Epub 2012 May 30. Maintenance and differentiation of neural stem cells Katlin B. Massirer, 1 Cassiano Carromeu, 1 Karim Griesi-Oliveira1, 2 and Alysson R. Muotri1. 2010, John Wiley & Sons, Inc. WIREs Syst Biol Med

IGF-1

Deuschle M, Blum W F, Strasburger C J, Schweiger U, Weber B, Körner A, Standhardt H, Gotthardt U, Schmider J, Pflaum C D, Heuser I. Insulin-like growth factor-I (IGF-I) plasma concentrations are increased in depressed patients. Psychoneuroendocrinology. 1997 October; 22(7):493-503.

Lesch K P, Rupprecht R, Müller U, Pfüller H, Beckmann H. Insulin-like growth factor 1 in depressed patients and controls. Acta Psychiatr Scand. 1988 December; 78(6): 684-8.

Franz B, Buysse D J, Cherry C R, Gray N S, Grochocinski V J, Frank E, Kupfer D J. Insulin-like growth factor 1 and growth hormone binding protein in depression: a preliminary communication. J Psychiatr Res. 1999 March-April; 33(2):121-7.

Michelson D, Amsterdam J, Apter J, Fava M, Londborg P, Tamura R, Pagh L. Hormonal markers of stress response following interruption of selective serotonin reuptake inhibitor treatment. Psychoneuroendocrinology. 2000 February; 25(2):169-77.

Midkine

Development. 2011 November; 138(21):4699-708. doi: 10.1242/dev.072157.

Midkine and Alk signaling in sympathetic neuron proliferation and neuroblastoma predisposition. Reiff T, Huber L, Kramer M, Delattre O, Janoueix-Lerosey I, Rohrer H. Research Group Developmental Neurobiology, Max Planck Institute for Brain Research, Deutschordenstr. 46, 60528, Frankfurt/M, Germany.

Curr Pharm Des. 2011; 17(5):410-23.

Midkine: a promising molecule for drug development to treat diseases of the central nervous system. Muramatsu T. Department of Health Science, Faculty of Psychological and Physical Science, Aichi Gakuin University, 12 Araike, Iwasaki-cho, Nisshin, Aichi 470-0195, Japan. tmurama@dpc.agu.ac.jp Curr Pharm Des. 2011; 17(5): 410-23.

Endothelian Dysfunction and Oxidative Stress

LOX-1

Renal vasoconstriction induced by oxidized LDL is inhibited by scavengers of reactive oxygen species and L-arginine. Rahman M M, Varghese Z, Fuller B J, Moorhead J F. Clin Nephrol. 1999 February; 51(2):98-107

Biomarkers of Vascular Disease Linking Inflammation to Endothelial Activation: Part II. Paul E. Szmitko, Chao-Hung Wang, Richard D. Weisel, Greg A. Jeffries, Todd J. Anderson Print ISSN: 0009-7322. Online ISSN: 1524-4539

Copyright© 2003 American Heart Association, Inc. All rights reserved.

Circulation is published by the American Heart Association, 7272 Greenville Avenue, Dallas, Tex. 75231 doi: 10.1161/01.CIR.0000089093.75585.98

Endothelin-1

Endothelin-1 Plasma Concentrations in Depressed Patients and Healthy Controls

Florian Lederbogen, Bettina Weber, Michael Colla, Isabella Heuser, Michael Deuschle. Central Institute of Mental Health, J5, Mannheim, Germany Neuropsychobiology 1999; 40:121-123 (DOI: 10.1159/000026607)

Depression predicts elevated endothelin-1 in patients with coronary artery disease. Burg M M, Martens E J, Collins D, Soufer R. Section of Cardiovascular Medicine, Yale University School of Medicine/VA Connecticut, 950 Campbell Avenue, West Haven, Conn. 06516, USA. Psychosom Med. 2011 January; 73(1):2-6. doi: 10.1097/PSY.0b013e3181fdfb25. Epub 2010 Oct. 14.

Tight Junction Hypothesis

Painsipp E, Köfer M J, Sinner F, Holzer P (2011) Prolonged Depression-Like Behavior Caused by Immune Challenge: Influence of Mouse Strain and Social Environment. PLoS ONE 6(6): e20719

Gliadin Induces an Increase in Intestinal Permeability and Zonulin Release by Binding to the Chemokine Receptor CXCR3. Karen M. Lammers, Ruliang Lu, Julie Brownley, Bao Lu, Craig Gerard, Karen Thomas Prasad Rallabhandi, Terez Shea-Donohue,* Amir Tamiz, Sefik Alkan, Sarah Netzel-Arnett, Toni Antalis, Stefanie N. Vogel, and Alessio Fasano. Gastroenterology. 2008 July; 135(1): 194-204.e3.

Zonulin

Human Zonulin, a Potential Modulator of Intestinal Tight Junctions

Wenle Wang1, Sergio Uzzau1, Simeon E. Goldblum2 and Alessio Fasano,

Division of Pediatric Gastroenterology and Nutrition and Gastrointestinal Pathophysiology Section, Center for Vaccine Development, 2 Division of Infectious Diseases, Department of Veterans Affairs Medical Center and 3 Department of Physiology, University of Maryland, School of Medicine, Baltimore, Md. 21201, USA; Journal of Cell Science 113, 4435-4440 (2000) 4435

Intestinal Zonulin: Open Sesame!

Dr A Fasano, Division of Pediatric Gastroenterology and Nutrition, University of Maryland School of Medicine, 685 W Baltimore St HSF Building, Room 465, Baltimore, Md. 21201, USA. Gut 2001; 49:159-162 doi:10.1136/gut.49.2.159

LIGHT Signals Directly to Intestinal Epithelia to Cause Barrier Dysfunction via Cytoskeletal and Endocytic Mechanisms Brad T. Schwarz, Fengjun Wang, Le Shen, Daniel R. Clayburgh, Liping Su, Yingmin Wang, Yang-Xin Fu, Jerrold R. Turner

*Gastroenterology*, Volume 132, Issue 7, June 2007, Pages 2383-2394

Immune-Inflammation

TNF-Alpha and IFN-Gamma

Gabbay V, Klein R G, Alonso C M, Babb J S, Nishawala M, De Jesus G, Hirsch G S, Hottinger-Blanc P M, Gonzalez C J. Immune system dysregulation in adolescent major depressive disorder. J Affect Disord. 2009; 115(1-2):177-82.

Michael R. Irwin and Andrew H. Miller Depressive disorders and immunity: 20 years of progress and discovery. Brain, Behavior, and Immunity Vol. 21, Issue 4, 2007, 374-383.

Teixeira A L, Reis H J, Coelho F M, Carneiro D S, Teixeira M M, Vieira L B, Mukhamedyarov M A, Zefirov A L, Janka Z, Palotás A. All-or-nothing type biphasic cytokine production of human lymphocytes after exposure to Alzheimer's beta-amyloid peptide. Biol Psychiatry. 2008; 15; 64(10):891-5.

Gladkevich A, Kauffman H F, Korf J. Lymphocytes as a neural probe: potential for studying psychiatric disorders. Prog Neuropsychopharmacol Biol Psychiatry. 2004 28(3):559-76.

Song C, Halbreich U, Han C, Leonard B E, Luo H. Imbalance between pro- and anti-inflammatory cytokines, and between Th1 and Th2 cytokines in depressed patients: the effect of electroacupuncture or fluoxetine treatment. Pharmacopsychiatry. 2009. 42(5):182-8.

Berthold-Losleben M, Himmerich H The TNF-alpha System: Functional Aspects in Depression, Narcolepsy and Psychopharmacology. Curr Neuropharmacol. 2008; 6(3): 193-202.

Himmerich H, Fulda S, Linseisen J, Seiler H, Wolfram G, Himmerich S, Gedrich K, Kloiber S, Lucae S, Ising M, Uhr M, Holsboer F, Pollmächer T. Depression, comorbidities and the TNF-alpha system. Eur Psychiatry. 2008; 23(6):421-9.

Schiepers O J, Wichers M C, Maes M. Cytokines and major depression. Prog Neuropsychopharmacol Biol Psychiatry. 2005; 29(2):201-17.

Kim Y K, Lee S W, Kim S H, Shim S H, Han S W, Choi S H, Lee B H. Differences in cytokines between non-suicidal patients and suicidal patients in major depression. Prog Neuropsychopharmacol Biol Psychiatry. 2008 Feb. 15; 32(2):356-61.

Simon N M, McNamara K, Chow C W, Maser R S, Papakostas G I, Pollack M H, Nierenberg A A, Fava M, Wong K K. A detailed examination of cytokine abnormalities in Major Depressive Disorder. Eur Neuropsychopharmacol. 2008 March; 18(3):230-3.

Hernández M E, Mendieta D, Martínez-Fong D, Loría F, Moreno J, Estrada I, Bojalil R, Pavón L. Variations in circulating cytokine levels during 52 week course of treatment with SSRI for major depressive disorder. Eur Neuropsychopharmacol. 2008; 18(12):917-24.

Irwin M R, Miller A H Depressive disorders and immunity: 20 years of progress and discovery. Brain Behav Immun 2007; 21(4):374-83

IL-Beta1

Anisman H. Cascading effects of stressors and inflammatory immune system activation: implications for major depressive disorder. J Psychiatry Neurosci. 2009 January; 34(1): 4-20.

Corwin E J, Johnston N, Pugh L. Symptoms of postpartum depression associated with elevated levels of interleukin-1 beta during the first month postpartum. Biol Res Nurs. 2008 October; 10(2):128-33.

Sutcigil L, Oktenli C, Musabak U, Bozkurt A, Cansever A, Uzun O, Sanisoglu S Y, Yesilova Z, Ozmenler N, Ozsahin A, Sengul A. Pro- and anti-inflammatory cytokine balance in major depression: effect of sertraline therapy. Clin Dev Immunol. 2007; 2007:76396.

Sutcigil L, Oktenli C, Musabak U, Bozkurt A, Cansever A, Uzun O, Sanisoglu S Y, Yesilova Z, Ozmenler N, Ozsahin A, Sengul A. Pro- and anti-inflammatory cytokine balance in major depression: effect of sertraline therapy. Clin Dev Immunol. 2007; 2007:76396.

Sadeghi M, Daniel V, Naujokat C, Weimer R, Opelz G. Strikingly higher interleukin (IL)-1alpha, IL-1beta and soluble interleukin-1 receptor antagonist (sIL-1RA) but similar IL-2, sIL-2R, IL-3, IL-4, IL-6, sIL-6R, IL-10, tumour necrosis factor (TNF)-alpha, transforming growth factor (TGF)-beta and interferon IFN-gamma urine levels in healthy females compared to healthy males: protection against urinary tract injury? Clin Exp Immunol. 2005 November; 142(2):312-7.

Pro Inflammatory Hypothesis

Fan, Yang-Yi and Robert S. Chapkin (9 Sep. 1998). "Importance of Dietary γ-Linolenic Acid in Human Health and Nutrition". Journal of Nutrition 128 (9): 1411-4. PMID 9732298. http://jn.nutrition.org/cgi/content/full/128/9/1411. Retrieved Oct. 16, 2007.

Belch, Jill J F and Alexander Hill (January 2000). "Evening primrose oil and borage oil in rheumatologic conditions". http://www.ajcn.org/cgi/content/full/71/1/3525. Retrieved Feb. 12, 2006.

PLA2 Inhibitors of Brain Phospholipase A2 Activity: Their Neuropharmacological Effects and Therapeutic Importance for the Treatment of Neurologic Disorders. AKHLAQ A. FAROOQUI, WEI-YI ONG, AND LLOYD A. HORROCKS Pharmacol Rev 58:591-620, 2006

Ho-Joo Lee, Richard P. Bazinet, Stanley I. Rapoport, and Abesh Kumar Bhattacharjee* Neurochem Res. Author manuscript; available in PMC 2010 Apr. 1.

Bipolar Disorders and Mechanisms of Action of Mood Stabilizers
Stanley I. Rapoport,* Mireille Basselin, Hyung-Wook Kim, and Jagadeesh S. Rao Brain Res Rev. 2009 October; 61(2): 185-209.
Su K P, Huang S Y, Peng C Y, Lai H C, Huang C L, Chen Y C, Aitchison K J, Pariante C M. Department of Psychiatry and Mind-Body Interface Laboratory, China Medical University, Hospital, Taichung, Taiwan.
Biol Psychiatry. 2010 Mar. 15; 67(6):550-7. doi: 10.1016/j.biopsych.2009.11.005. Epub 2009 Dec. 24. Phospholipase A2 and cyclooxygenase 2 genes influence the risk of interferon-alpha-induced depression by regulating polyunsaturated fatty acids levels.

Omega-3

Review Omega-3 Fatty Acids and Mood Disorders.
Parker G, Gibson N A, Brotchie H, Heruc G, Rees A M, Hadzi-Pavlovic D.
Am J Psychiatry. 2006 June; 163(6):969-78.
Dietary-Linolenic Acid Inhibits Proinflammatory Cytokine Production by Peripheral Blood Mononuclear Cells in Hypercholesterolemic Subjects 1-3
Guixiang Zhao, Terry D Etherton, Keith R Martin, Peter J Gillies, Sheila G West, and Penny M Kris-Etherton. Am J Clin Nutr 2007; 85:385-91. Printed in USA. © 2007 American Society for Nutrition
J Clin Psychiatry 68:7, July 2007. A Meta-Analytic Review of Double-Blind, lacebo-Controlled Trials of Antidepressant Efficacy of Omega-3 Fatty Acids Pao-Yen Lin, M.D., Ph.D., and Kuan-Pin Su, M.D.

PGE2

Muller N. COX-2 inhibitors as antidepressants and antipsychotics: clinical evidence. Curr Opin Investig Drugs. 2010 January; 11(1):31-42.
Müller N, Schwarz M J. COX-2 inhibition in schizophrenia and major depression. Curr Pharm Des. 2008; 14(14): 1452-65.

A (Change in) Energy State

Adiponectin

Taylor V H, Macqueen G M. The Role of Adipokines in Understanding the Associations between Obesity and Depression. J Obes. 2010; 2010. pii: 748048.
Cizza G, Nguyen V T, Eskandari F, Duan Z, Wright E C, Reynolds J C, Ahima R S, Blackman M R; POWER Study Group. Low 24-hour adiponectin and high nocturnal leptin concentrations in a case-control study of community-dwelling premenopausal women with major depressive disorder: the Premenopausal, Osteopenia/Osteoporosis, Women, Alendronate, Depression (POWER) study. J Clin Psychiatry. 2010 August; 71(8):1079-87.
Zeman M, Jirak R, Jachymova M, Vecka M, Tvrzicka E, Zak A. Leptin, adiponectin, leptin to adiponectin ratio and insulin resistance in depressive women. Neuro Endocrinol Lett. 2009; 30(3):387-95.
Lehto S M, Huotari A, Niskanen L, Tolmunen T, Koivumaa-Honkanen H, Honkalampi K, Ruotsalainen H, Herzig K H, Viinamaki H, Hintikka J. Serum adiponectin and resistin levels in major depressive disorder. Acta Psychiatr Scand. 2010 March; 121(3):209-15.

Others

Neuropeptide Y (NPY) shortens sleep latency but does not suppress ACTH and cortisol in depressed patients and normal controls. Psychoneuroendocrinology. 2006 January; 31(1):100-7.
Pohl A, Nordin C. Clinical and biochemical observations during treatment of depression with electroacupuncture: a pilot study. Hum Psychopharmacol. 2002 October; 17(7): 345-8.
Czermak C, Hauger R, Drevets W C, Luckenbaugh D A, Geraci M, Charney D S, NPYNeumeister A. Plasma NPY concentrations during tryptophan and sham depletion in medication-free patients with remitted depression. J Affect Disord. 2008 October; 110(3):277-81.
Westrin A, Ekman R, Traskman-Bendz L. Alterations of corticotropin releasing hormone (CRH) and neuropeptide Y (NPY) plasma levels in mood disorder patients with a recent suicide attempt. Eur Neuropsychopharmacol. 1999 March; 9(3):205-11.
Hashimoto H, Onishi H, Koide S, Kai T, Yamagami S. Plasma neuropeptide Y in patients with major depressive disorder. Neurosci Lett. 1996 Sep. 20; 216(1):57-60.
Redrobe J P, Dumont Y, Quirion R. Neuropeptide Y (NPY) and depression: from animal studies to the human condition. Life Sci. 2002 Nov. 8; 71(25):2921-37.
Morales-Medina J C, Dumont Y, Quirion R. A possible role of neuropeptide Y in depression and stress. Brain Res. 2009.

The invention claimed is:

1. A method for measuring concentration of biomarkers comprising
    measuring the concentration of at least two biomarkers in urine samples from an individual suspected of having a mood disorder,
    wherein the at least two biomarkers are Herpes Virus Entry Mediator (HVEM)(TNFRSF14)(UniProtKB/Swiss-Prot accession Q92956.3) (urine) and thromboxane (urine) and,
    further measuring the concentration of one or more biomarkers measured in urine or blood samples selected from the group consisting of aldosteron (urine), substance P (urine), endothelin (urine and/or serum), isoprostane (urine), cortisol (urine and/or serum), Leukotriene B4 (LTB4) (urine), calprotectin (urine and/or serum), cyclic guanosine monophosphate (cGMP) (urine), leptin (serum), thromboxane (serum), and tumor necrosis factor (TNF) alpha receptor 2 (serum), and
    wherein the measured concentration of urine biomarkers is normalized to the concentration of creatinine in the urine.

2. The method of claim 1, wherein the biomarkers comprises thromboxane (urine), HVEM (urine) and aldosteron (urine), and one or more biomarkers selected from the group consisting of substance P (urine), endothelin (urine and/or serum), isoprostane (urine), cortisol (urine and/or serum), Leukotriene B4 (LTB4) (urine), calprotectin (urine and/or serum), cyclic guanosine monophosphate (cGMP) (urine), leptin (serum), thromboxane (serum), and tumor necrosis factor (TNF) alpha receptor 2 (serum), and
    wherein the measured concentration of urine biomarkers is normalized to the concentration of creatinine in the urine.

3. The method of claim 1, wherein the biomarkers comprises thromboxane (urine), HVEM (urine), aldosteron (urine), and substance P (urine), and one or more biomarkers selected from the group consisting of endothelin (urine and/or serum), isoprostane (urine), cortisol (urine and/or serum), LTB4 (urine), calprotectin (urine and/or serum), cGMP (urine), leptin (serum), thromboxane (serum), and tumor necrosis factor (TNF) alpha receptor 2 (serum).

4. The method of claim 1, wherein the biomarkers comprises thromboxane (urine), aldosteron (urine), substance P (urine), and HVEM (urine), and one or more biomarkers selected from the group consisting of endothelin (urine and/or serum), isoprostane (urine), cortisol (urine and/or serum), LTB4 (urine), calprotectin (urine and/or serum), cGMP (urine), leptin (serum), thromboxane (serum), and tumor necrosis factor (TNF) alpha receptor 2 (serum).

5. The method of claim 1, wherein the biomarkers comprises thromboxane (urine), aldosteron (urine), substance P (urine), HVEM (urine), and endothelin (urine), and one or more biomarkers selected from the group consisting of endothelin (serum), isoprostane (urine), cortisol (urine and/or serum), LTB4 (urine), calprotectin (urine and/or serum), cGMP (urine), leptin (serum), thromboxane (serum), and tumor necrosis factor (TNF) alpha receptor 2 (serum).

6. The method of claim 1, wherein the biomarkers comprises thromboxane (urine), aldosteron (urine), substance P (urine), HVEM (urine), endothelin (urine), and isoprostane (urine), and one or more biomarkers selected from the group consisting of endothelin (serum), cortisol (urine and/or serum), LTB4 (urine), calprotectin (urine and/or serum), cGMP (urine), leptin (serum), thromboxane (serum), and tumor necrosis factor (TNF) alpha receptor 2 (serum).

7. The method of claim 1, wherein the biomarkers comprises thromboxane (urine), aldosterone (urine), substance P (urine), HVEM (urine), endothelin (urine), isoprostane (urine), and cortisol (urine), and one or more biomarkers selected from the group consisting of endothelin (serum), cortisol (serum), LTB4 (urine), calprotectin (urine and/or serum), cGMP (urine), leptin (serum), thromboxane (serum), and tumor necrosis factor (TNF) alpha receptor 2 (serum).

8. The method of claim 1, further including measuring the concentration of one or more biomarkers measured in urine selected from the group consisting of activin, cAMP, digoxin, lipocalin, neopterin, Leukotriene B4 (LTB4), tumor necrosis factor (TNF) alpha receptor 2, HVEM, prostaglandin E2 (PGE2), thromboxane B2, lectin-like oxidized LDL receptor-1 (LOX-1), nitrotyrosine, F2-isoprostane, midkine, insulin-like growth factor (IGF), endothelin-1, cGMP, gamma amino butyric acid (GABA), vitamin D, cortisol, pregnenolone, substance P, epidermal growth factor (EGF), calprotectin, leptin, myeloperoxidase, neuropeptide Y, cholesystokinin (CCK), soluble vascular endothelial growth factor receptor 1 (sVEGFR1), arginine vasopressin (AVP), and adiponectin, or measuring the concentration of one or more biomarkers measured in serum selected from the group consisting of activin, cAMP, aldosteron, lipocalin, tumor necrosis factor (TNF) alpha receptor 2, interleukin-6 (IL-6), galectin-8, PGE2, thromboxane B2, LOX-1, nitrotyrosine, F2-isoprostane, brain-derived neurotrophic factor (BDNF), pigment epithelium-derived factor (PEDF), midkine, endothelin-1, cAMP, cGMP, gamma amino butyric acid (GABA), vitamin D, pregnenolone, substance P, epidermal growth factor (EGF), zonulin, calprotectin, visinin-like protein (VILIP), leptin, AVP, neuropeptide Y, matrix metalloproteinase 1 (MMP-1), bovine fibroblast growth factor (bFGF), digoxin, B cell leukemia-2 (BCL-2), calreticulin, myeloperoxidase, LTB4, phospholipase A2 (PLAF), sVEGFR1 and adiponectin.

9. The method of claim 1, wherein the biomarkers include at least two biomarkers identified in FIG. 4 or FIG. 5.

10. The method of claim 1, wherein the urine is first morning urine.

11. The method of claim 1, wherein the mood disorder is depression.

12. The method of claim 1, wherein the mood disorder is dysthymia, endogenous depression, reactive depression, minor depression, major depression, psychotic depression, neurotic depression, postnatal depression, burn out, overstrain, unipolar depression or bipolar depression.

13. The method of claim 1, wherein the concentration of the biomarkers is measured by one or more methods selected from the group consisting of SELDI (-TOF), MALDI (-TOF), a 1-D gel-based analysis, a 2-D gel-based analysis, Mass spec (MS), LC, reverse phase (RP) LC, size permeation (gel filtration), ion exchange, affinity, HPLC, and UPLC, or wherein the detection of the biomarker is performed by an immunological method, or wherein the detection of the biomarker is performed by mRNA/DNA based methods including (RT)-PCR, hybridization and sequencing techniques, or wherein the detection of the biomarker is performed by determining the methylation status of the gene encoding said biomarker, or wherein the detection of the biomarker is performed using a biosensor or a microanalytical, micro-engineered, micro-separation or immunochromatography system.

14. The method of claim 1, wherein the blood or urine samples are contacted with an antibody.

* * * * *